(12) United States Patent
Godawat et al.

(10) Patent No.: US 9,630,165 B2
(45) Date of Patent: *Apr. 25, 2017

(54) STERILE CHROMATOGRAPHY RESIN AND USE THEREOF IN MANUFACTURING PROCESSES

(71) Applicant: Genzyme Corporation, Cambridge, MA (US)

(72) Inventors: Rahul Godawat, Bridgewater, NJ (US); Veena Warikoo, Bridgewater, NJ (US); Rohan Patil, Bridgewater, NJ (US); Konstantin Konstantinov, Bridgewater, NJ (US); Venkat Kishore Ryakala, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/629,315

(22) Filed: Feb. 23, 2015

(65) Prior Publication Data

US 2015/0203531 A1 Jul. 23, 2015

Related U.S. Application Data

(63) Continuation of application No. 14/598,401, filed on Jan. 16, 2015.

(60) Provisional application No. 61/928,929, filed on Jan. 17, 2014, provisional application No. 62/001,498, filed on May 21, 2014.

(51) Int. Cl.

| | | |
|---|---|---|
| *B01J 20/34* | (2006.01) |
| *B01D 15/36* | (2006.01) |
| *B01D 15/38* | (2006.01) |
| *B01J 20/26* | (2006.01) |
| *B01J 20/281* | (2006.01) |
| *B01J 41/12* | (2017.01) |
| *B01J 41/20* | (2006.01) |
| *C07K 1/16* | (2006.01) |
| *C07K 1/22* | (2006.01) |
| *A61L 2/08* | (2006.01) |
| *C07K 1/18* | (2006.01) |
| *B01D 15/18* | (2006.01) |
| *B01D 15/20* | (2006.01) |
| *B01D 15/32* | (2006.01) |
| *B01D 15/34* | (2006.01) |
| *B01J 39/26* | (2006.01) |

(52) U.S. Cl.
CPC .......... *B01J 20/3441* (2013.01); *A61L 2/081* (2013.01); *B01D 15/1864* (2013.01); *B01D 15/20* (2013.01); *B01D 15/327* (2013.01); *B01D 15/34* (2013.01); *B01D 15/362* (2013.01); *B01D 15/363* (2013.01); *B01D 15/3804* (2013.01); *B01J 20/265* (2013.01); *B01J 20/281* (2013.01); *B01J 39/26* (2013.01); *B01J 41/12* (2013.01); *B01J 41/20* (2013.01); *C07K 1/16* (2013.01); *C07K 1/18* (2013.01); *C07K 1/22* (2013.01); *Y10T 29/49826* (2015.01)

(58) Field of Classification Search
CPC ............................ B01D 15/363; A61L 2/081
USPC ........................................ 530/412; 422/222
See application file for complete search history.

(56) References Cited

U.S. PATENT DOCUMENTS

| | | |
|---|---|---|
| 533,575 A | 2/1895 | Wilkens |
| 4,401,108 A | 8/1983 | Galkin et al. |
| 4,599,175 A | 7/1986 | Paciorek et al. |
| 5,169,936 A | 12/1992 | Staples et al. |
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michnel |
| 5,423,982 A | 6/1995 | Jungbauer et al. |
| 5,480,387 A | 1/1996 | Gabriel et al. |

(Continued)

FOREIGN PATENT DOCUMENTS

| | | |
|---|---|---|
| CN | 102321316 | 1/2012 |
| EP | 0281368 | 9/1988 |

(Continued)

OTHER PUBLICATIONS

Anderson, "Practical use of continuous processing in developing and scaling up laboratory processes," *Org. Proc. Res. Dev.*, 5(6):613-621, 2001.

(Continued)

*Primary Examiner* — Edward Cain
(74) *Attorney, Agent, or Firm* — Fish & Richardson P.C.

(57) ABSTRACT

Provided herein are methods of reducing bioburden of (e.g., sterilizing) a chromatography resin that include exposing a container including a composition including a chromatography resin and at least one antioxidant agent and/or chelator to a dose of gamma-irradiation sufficient to reduce the bioburden of the container and the chromatography resin, where the at least one antioxidant agent and/or chelator are present in an amount sufficient to ameliorate the loss of binding capacity of the chromatography resin after/upon exposure to the dose of gamma-irradiation. Also provided are reduced bioburden chromatography columns including the reduced bioburden chromatography resin, compositions including a chromatography resin and at least one chelator and/or antioxidant agent, methods of performing reduced bioburden column chromatography using one of these reduced bioburden chromatography columns, and integrated, closed, and continuous processes for reduced bioburden manufacturing of a purified recombinant protein.

30 Claims, 11 Drawing Sheets

(56) References Cited

U.S. PATENT DOCUMENTS

| | | |
|---|---|---|
| 5,505,704 A | 4/1996 | Pawelka et al. |
| 5,571,720 A | 11/1996 | Grandics et al. |
| 5,582,598 A | 12/1996 | Chanoch |
| 5,606,033 A | 2/1997 | Cramer et al. |
| 5,610,285 A | 3/1997 | Lebing et al. |
| 5,626,566 A | 5/1997 | Petersen et al. |
| 5,674,204 A | 10/1997 | Chanoch |
| 5,688,251 A | 11/1997 | Chanoch |
| 5,856,179 A | 1/1999 | Chen et al. |
| 5,921,966 A | 7/1999 | Bendek |
| 5,961,495 A | 10/1999 | Walters et al. |
| 6,004,297 A | 12/1999 | Steenfeldt-Jensen et al. |
| 6,127,526 A | 10/2000 | Blank |
| 6,180,401 B1 | 1/2001 | Chen et al. |
| 6,193,698 B1 | 2/2001 | Kirchhofer |
| 6,221,046 B1 | 4/2001 | Burroughs et al. |
| 6,235,004 B1 | 5/2001 | Steenfeldt-Jensen |
| 6,248,095 B1 | 6/2001 | Giambattista et al. |
| 6,265,542 B1 | 7/2001 | Fahrner et al. |
| 6,307,028 B1 | 10/2001 | Lebing et al. |
| 6,333,398 B1 | 12/2001 | Blank |
| 6,359,114 B1 | 3/2002 | Grimes et al. |
| 6,410,270 B1 | 6/2002 | Strittmatter et al. |
| 6,417,335 B1 | 7/2002 | Basey et al. |
| 6,489,447 B1 | 12/2002 | Basey et al. |
| 6,551,512 B1 | 4/2003 | Britsch et al. |
| 6,660,172 B2 | 12/2003 | Koslow |
| 6,870,034 B2 | 3/2005 | Breece et al. |
| 6,899,698 B2 | 5/2005 | Sams |
| 6,902,909 B2 | 6/2005 | Navran, Jr. et al. |
| 6,936,032 B1 | 8/2005 | Bush et al. |
| 6,955,917 B2 | 10/2005 | Alred et al. |
| 7,220,356 B2 | 5/2007 | Thommes et al. |
| 7,241,278 B2 | 7/2007 | Moller |
| 7,323,553 B2 | 1/2008 | Fahrner et al. |
| 7,531,645 B2 | 5/2009 | Basey et al. |
| 7,544,784 B2 | 6/2009 | Sassenfeld et al. |
| 7,553,938 B2 | 6/2009 | Buchacher et al. |
| 7,662,930 B2 | 2/2010 | Zhou |
| 7,673,757 B2 | 3/2010 | Yavorsky |
| 7,714,112 B2 | 5/2010 | Engstrand et al. |
| 7,759,117 B2 | 7/2010 | Pham |
| 7,928,205 B2 | 4/2011 | Dillon et al. |
| 8,044,017 B2 | 10/2011 | Emery et al. |
| 8,117,924 B2 | 2/2012 | Joeris |
| RE43,655 E | 9/2012 | Lebing et al. |
| 8,580,554 B2 | 11/2013 | Grillberger et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2005/0272146 A1 | 12/2005 | Hodge et al. |
| 2006/0046261 A1 | 3/2006 | Porter |
| 2006/0153693 A1 | 7/2006 | Fiechter |
| 2006/0183198 A1 | 8/2006 | Buechler |
| 2007/0244307 A1 | 10/2007 | Engstrand et al. |
| 2008/0031877 A1 | 2/2008 | Covacci |
| 2009/0275916 A1 | 11/2009 | Harms |
| 2009/0298121 A1 | 12/2009 | Schwartz |
| 2010/0330627 A1 | 12/2010 | Shimada |
| 2012/0255642 A1 | 10/2012 | Gebauer |
| 2013/0061941 A1 | 3/2013 | Gebauer |
| 2013/0068671 A1 | 3/2013 | Gebauer et al. |
| 2014/0038264 A1 | 2/2014 | Grillberger et al. |
| 2014/0255994 A1 | 9/2014 | Konstantinov et al. |
| 2015/0183821 A1 | 7/2015 | Konstantinov et al. |
| 2015/0202595 A1 | 7/2015 | Godawat et al. |
| 2015/0203529 A1 | 7/2015 | Godawat et al. |
| 2015/0203532 A1 | 7/2015 | Godawat et al. |
| 2015/0232505 A1 | 8/2015 | Konstantinov et al. |
| 2016/0256633 A1 | 9/2016 | Veasey et al. |

FOREIGN PATENT DOCUMENTS

| | | |
|---|---|---|
| EP | 0621074 | 10/1994 |
| EP | 0937476 | 1/2005 |
| EP | 0937471 | 9/2005 |
| EP | 2020433 | 3/2013 |
| EP | 2682168 | 1/2014 |
| GB | 20030004822 | 3/2003 |
| GB | 20030004823 | 3/2003 |
| WO | WO9106008 | 5/1991 |
| WO | WO9217403 | 10/1992 |
| WO | WO9422490 | 10/1994 |
| WO | WO9938554 | 8/1999 |
| WO | WO0110484 | 2/2001 |
| WO | WO2002/41989 | 5/2002 |
| WO | 03/045546 | 6/2003 |
| WO | 2006/039588 | 4/2006 |
| WO | WO 2006/096116 | 9/2006 |
| WO | 2008/073620 | 6/2008 |
| WO | WO 2008/110291 | 9/2008 |
| WO | 2008/127087 | 10/2008 |
| WO | 2011/076386 | 6/2011 |
| WO | 2011/078772 | 6/2011 |
| WO | 2011/152788 | 12/2011 |
| WO | 2012/078677 | 6/2012 |
| WO | WO 2013/159858 | 10/2013 |
| WO | 2014/004103 | 1/2014 |
| WO | 2014/004281 | 1/2014 |
| WO | 2014/137903 | 9/2014 |
| WO | 2015/109246 | 7/2015 |
| WO | WO 15/109146 | 7/2015 |

OTHER PUBLICATIONS

Bisschops et al., "Single-Use, Continuous-Countercurrent, Multicolumn Chromatography," *BioProcess International*, Supplement, pp. 18-23, Jun. 1, 2009.

Grabski and Mierendorf, "Simulated moving bed chromatography," Genetic Engineering & Biotechnology News [online], Oct. 15, 2009 [retrieved on Jul. 16, 2014]. Retrieved from the Internet: < URL: http://www.genengnews.com/gen-articles/simulated-moving-bed-chromatography/3076/>, vol. 29, No. 18, 4 pages.

Holzer et al., "Multicolumn Chromatography: A new approach to relieving downstream processing efficiency," *BioProcess International*, Retrieved capacity bottlenecks for from the Internet: < URL: http://www.novasep.com/upload/news/PDF/3176Multicolumn_Chromatography-BioProcess-Internationa.pdf>, 6 pages, Sep. 2008.

International Search Report and Written Opinion for PCT/US2014/019909 mailed May 21, 2014, 10 pages.

Jayapal et al., "Recombinant protein therapeutics from CHO cells—20 years and counting, " *CHO Consortium* SBE Special Edition pp. 40-47, 2007.

Laird, "Continuous processes in small-scale manufacture," *Organic Process Research & Development*, 11(6):927, 2007.

Ohashi et al., "Perfusion cell culture in disposable bioreactors," presented at ESACT in 2001, Sweden, 6 pages.

Vogel et al, "Continuous annular chromatography: General characterization and application for the isolation of recombinant protein drugs," *Biotechnol Bioeng.*, 80(5):559-568, Dec. 5, 2002.

Warikoo et al., "Integrated continuous production of recombinant therapeutic proteins," *Biotechnol Bioeng.*, 109(12):3018-3029. Epub Aug. 6, 2012.

Brower, M., et al., "What Can Continuous Processing Do for You?" Biopharmaceutical Development & Production Week Conference, Huntington Beach, CA, Feb. 28, 2013, 27 pages.

Ransohoff, T.C., "The Potential for Continuous Chromatography and DSP in Clinical Manufacturing of Biopharmaceuticals," Biopharmaceutical Development & Production Week Conference, Huntington Beach, CA, Feb. 28, 2013, 29 pages.

Ferre et al., "Purification of correctly oxidized MHC class I heavy-chain molecules under denaturing conditions: A novel strategy exploiting disulfide assisted protein folding," *Protein Science* 12:551-559 (2003).

(56) References Cited

OTHER PUBLICATIONS

Office Action issued in U.S. Appl. No. 14/629,356 on Jul. 7, 2015 (16 pages).
U.S. Appl. No. 14/598,450, filed Jan.16, 2015, Godawat et al.
U.S. Appl. No. 14/598,401, filed Jan. 16, 2015, Godawat et al.
U.S. Appl. No. 14/629,356, filed Feb. 23, 2015, Godawat et al.
International Search Report and Written Opinion for PCT/US2015/011698 mailed Apr. 17, 2015, 13 pages.
Gagnon, P., "Dissection of the Separation Mechanisms and Enhancement of Aggregate Removal by Charged-Hydrophobic Mixed Mode Chromatography," $6^{th}$ International Symposium on HIC and RPC, Mar. 16-19, 2009, 30 pages.
GE Healthcare, "Use of sodium hydroxide for cleaning and sanitizing chromatography media and systems," Application Note 18/1124-57 AF Process Chromatography, Sep. 2006 pp. 1-8.
"Capto Adhere—Affinity Chromatography", Feb. 20, 2012, (39 pages).
GE Healthcare: "Ion Exchange Chromatography & Chromatofocusing Principles and Methods Ion Exchange Chromatography & Chromatofocusing—Principles and Methods imagination at work," Apr. 2010.
"Multimodal Chromatography—Handbook GE Healthcare Life Sciences imagination at work Multimodal Chromatography Handbook," Nov. 2013.
Ng et al., "Regeneration Studies of Anion-Exchange Chromatography Resins," Bioprocess International, 5(5):52-56 (May 2007).
"Guide to Irradiation and Sterilization Validation of Single-Use Bioprocess Systems," BioProcess International, May 2008, pp. 10S-22S.
"Method for radiation sterilization of sensitive chromatographic resins and membranes," IP.com No. IPCOM000188023D (Sep. 18, 2009).
Moore et al., "Protection of Protein A—Sepharose Columns Irradiated to Sterilization Doses," Radiat. Phys. Chem., 47(1):161-165 (1996).
International Search Report and Written Opinion issued in PCT/US2015/011705 on Apr. 30, 2015 (16 pages).
Degenhardt et al., "Separation and 42-45, Purification of Anthocyanins by High-Speed 49,51 Countercurrent Chromatography and Screening for Antioxidant Activity", Journal of Agricultural and Food Chemistry, 48(2):338-343 (Jan. 13, 2000).
Kostova et al., "Preparative 42,43, Chromatographic Separation of Amino Acid 46-49 Racemic Mixtures1. Adsorption Isotherms," Separation and Purification Technology, 54(3): 340-348 (2007).
Styskin et al., "Gas Chromatography of 42,45,51 Phenolic Antioxidants," Journal of Chromatography, 77(1):11-19 (1973).
Database WPI Thomson Scientific, London, GB; RU 2034853 Abstract; May 10, 1995.
First Third-Party Submission under 37 CFR 1.290 and Concise Description of Relevance filed in U.S. Appl. No. 14/598,401, filed Nov. 2, 2015 (16 pages).
Second Third-Party Submission under 37 CFR 1.290 and Concise Description of Relevance filed in U.S. Appl. No. 14/598,401, filed Nov. 2, 2015 (21 pages).
Third-Party Submission under 37 CFR 1.290 and Concise Description of Relevance filed in U.S. Appl. No. 14/598,401, filed Dec. 3, 2015 (16 pages).
Third-Party Submission under 37 CFR 1.290 and Concise Description of Relevance filed in U.S. Appl. No. 14/598,450, filed Nov. 5, 2015 (12 pages).
Third-Party Submission under 37 CFR 1.290 and Concise Description of Relevance filed in U.S. Appl. No. 14/598,450, filed Nov. 2, 2015 (21 pages).
Gil et al., "Challenging the Cleanroom Paradigm for Biopharmaceutical Manufacturing of Bulk Drug Substances," BioPharm Int., pp. 1-9, Aug. 1, 2011.
Mueller-Spath et al., "Two Step Capture and Purification of IgG2 Using Multicolumn Countercurrent Solvent Gradient Purification (MCSGP)" Biotechnol. Bioeng. 107(6): 974-984, Jul. 30, 2010.
Zbikowska et al., "Protein modification caused by a high dose of gamma irradiation in cryosterilized plasma: Protective effects of ascorbate," Free Radical Biology & Medicine 40:536-542, Oct. 14, 2005.
Final Office Action issued in U.S. Appl. No. 14/627,559, dated Feb. 18, 2016, 17 pages.
Final Office Action issued in U.S. Appl. No. 14/629,356, dated Aug. 29, 2016, 15 pages.
Final Office Action issued in U.S. Appl. No. 14/645,138, dated Feb. 18, 2016, 17 pages.
International Preliminary Report on Patentability in International Application No. PCT/US2014/019909, mailed Sep. 17, 2015, 7 pages.
International Preliminary Report on Patentability in International Application No. PCT/US2015/011705, issued Jul. 19, 2016, 11 pages.
International Preliminary Report on Patentability in International Application No. PCT/US2015/011698, mailed Jul. 28, 2016, 8 pages.
Non-final Office Action issued in U.S. Appl. No. 14/195,481, dated Sep. 22, 2015, 25 pages.
Supplemental Information from Mueller-Spath et al., "Two Step Capture and Purification Purification of IgG2 Using Multicolumn Countercurrent Solvent Gradient Purification (MCSGP)" Biotechnol. Bioeng. 107(6):974-984, Jul. 30, 2010, 15 pages.
Tricorn column last viewed Sep. 17, 2015, 1 page.
Written Opinion in Singapore Patent Application No. 11201506775V, dated Aug. 16, 2016, 6 pages.
U.S. Appl. No. 61/420,066, filed Dec. 6, 2010, Ransohoff et al.
U.S. Appl. No. 61/775,060, filed Mar. 8, 2013, Konstantinov et al.
U.S. Appl. No. 61/856,390, filed Jul. 19, 2013, Konstantinov et al.
U.S. Appl. No. 61/928,906, filed Jan. 17, 2014, Godawat et al.
U.S. Appl. No. 61/928,929, filed Jan. 17, 2014, Godawat et al.
U.S. Appl. No. 62/001,498, filed May 12, 2014, Godawat et al.
Berthod et al., Analytical Separation Science, First Edition, 2015, Wiley-VCH Verlag GmbH & Co., Edited by Jared L. Anderson, Alain Berthod, Veronica Pino Estevez, and Apryll M. Stalcup, pp. 1177-1206.
Blank et al., Self-Immobilizing Recombinant anitbody Fragments for Immunoaffinity Chromatography: Generic, Parallel, and Scalable Protein Purification, 2002, 24(2): 313-322.
Chisti et al., Large Scale Protein Separations: Engineering Aspects of Chromatography, Biotech. Adv. 1990,8: 699-708.
Guide to Irradiation and Sterilization Validation of Single-Use Bioprocess Systems, BioProcess International, May 2008: 10S-22S.
Holzer et al., "Multicolumn Chromatography: A new approach to relieving capacity bottlenecks for downstream processing efficiency," BioProcess International, Retrieved from the Internet: <URL: http://www.novasep.com/upload/news/PDF/3176Multicolumn_Chromatography-Bio-Process-International.pdf>, 6 pages, Sep. 2008.
Non-final Office Action issued in U.S. Appl. No. 14/598,401, dated Apr. 19, 2016, 7 pages.
Non-final Office Action issued in U.S. Appl. No. 14/627,559, dated Oct. 1, 2015, 17 pages.
Non-final Office Action issued in U.S. Appl. No. 14/645,138, dated Sep. 22, 2015, 14 pages.
Non-final Office Action issued in U.S. Appl. No. 14/195,481, dated Apr. 29, 2016, 50 pages.
Final Office Action issued in U.S. Appl. No. 14/629,356, dated Feb. 10, 2016, 13 pages.
Rosset, AJ, Neuzil, RW and Broughton DB. Industrial application of preparative chromatogmphy,in: Rodrigues AE, Tondeur D (eds.), Percolation Processes: Theory and Application, Rockville, MD, Sijthoff & Noordhoff Press, 1981.
Shinkazh et al., Countercurrent tangential chromatography for large-scale protein purification, Biotechnol Bioeng. Mar. 2011, 108(3): 582-591.

| Resin | $A_{280}$ |
|---|---|
| Mab Select SuRe (30 kGY) | 0.07 |
| JSR Amsphere (30 kGY) | 0.14 |

Lysosomal storage diseases and associated enzymatic defects

| Disease | Enzymatic Defect |
| --- | --- |
| Pompe disease | acid α-glucosidase (e.g., Myozyme®, Lumizyme®) |
| MPSI* (Hurler disease) | α-L-iduronidase (e.g., Aldurazyme®) |
| MPSII (Hunter disease) | iduronate sulfatase |
| MPSIII (Sanfilippo) | heparan N-sulfatase |
| MPS IV (Morquio A) | galactose-6-sulfatase |
| MPS IV (Morquio B) | acid β-galactosidase |
| MPS VII (Sly disease) | β-glucoronidase |
| I-cell disease | N-acetylglucosamine-1-phosphotransferase |
| Schindler disease | α-N-acetylgalactosaminidase (α-galactosidase B) |
| Wolman disease | acid lipase |
| Cholestrol ester storage disease | acid lipase |
| Farber disease | lysosomal acid ceramidase |
| Niemann-Pick disease | acid sphingomyelinase |
| Gaucher disease | β-glucosidase (e.g. Cerezyme®, Ceredase®) |
| Krabbe disease | galactosylceramidase |
| Fabry disease | α-galactosidase A |
| GM1 gangliosidosis | acid β-galactosidase |
| Galactosialidosis | β-galactosidase and neuraminidase |
| Tay-Sach's disease | hexosaminidase A |
| Sandhoff disease | hexosaminidase A and B |

*MPS = mucopolysaccaridosis

FIG. 10

STERILE CHROMATOGRAPHY RESIN AND USE THEREOF IN MANUFACTURING PROCESSES

CROSS REFERENCE TO RELATED APPLICATIONS

This application is a continuation application of U.S. patent application Ser. No. 14/598,401, filed on Jan. 16, 2015, which claims priority to U.S. Provisional Patent Application Ser. No. 61/928,929, filed on Jan. 17, 2014, and U.S. Provisional Patent Application Ser. No. 62/001,498, filed on May 21, 2014, which are incorporated by reference in their entirety.

TECHNICAL FIELD

This invention relates to methods of biotechnology and the biomanufacturing of recombinant proteins.

BACKGROUND

Mammalian cells including a nucleic acid that encodes a recombinant protein are often used to produce therapeutically or commercially important proteins. In the current environment of diverse product pipelines, biotechnology companies are increasingly driven to develop innovative solutions for highly flexible and cost-effective manufacturing of therapeutic protein drug substances. One of the strategies for efficiently isolating recombinant proteins is through processes that include continuous chromatography (e.g., using a closed system). One known limitation of continuous chromatography is the presence of contaminating agents in the system (e.g., increased bioburden), which results in a contaminated product, a reduction in the production yield, and a decrease in the flow-rate (or increase in the pressure) in the system. For example, the increased bioburden within a system can result in the complete shut down of the system.

SUMMARY

The present invention is based, at least in part, on the discovery that gamma-irradiation of chromatography resin reduces the binding capacity of the chromatography resin. In view of this discovery, provided herein are methods of reducing bioburden of a chromatography resin that include exposing a container including a composition including a chromatography resin and at least one antioxidant agent and/or chelator to a dose of gamma-irradiation sufficient to reduce the bioburden of the container and the chromatography resin, where the at least one antioxidant agent and/or chelator are present in an amount sufficient to ameliorate the loss of binding capacity of the chromatography resin after/upon exposure to the dose of gamma-irradiation. Also provided are methods of reducing bioburden of a chromatography resin that include exposing a container including a composition including a chromatography resin (and optionally at least one antioxidant agent and/or chelator in an amount sufficient to ameliorate loss of binding capacity of the chromatography resin after/upon exposure to gamma-irradiation) to gamma-irradiation at a rate of between about 0.1 kGy/hour to about 6 kGy hour and/or at a temperature between about 4° C. to about 25° C., for a dose of gamma-irradiation sufficient to reduce the bioburden of the container and the chromatography resin. Also provided are reduced bioburden chromatography columns containing a reduced bioburden chromatography resin prepared by any of the methods described herein, compositions including a chromatography resin and at least one chelator and/or antioxidant agent, methods of performing reduced bioburden column chromatography using at least one of these reduced bioburden chromatography columns, and integrated, closed or substantially closed, and continuous processes for reduced bioburden manufacturing of a purified recombinant protein that include the use of at least one of these reduced bioburden chromatography columns. Any of the chromatography resins produced by any of the methods described herein, any of the packed chromatography columns produced by any of the methods described herein, any of the methods of performing column chromatography, and any of the processes described herein can be sterile, absolutely sterile, aseptic, or reduced bioburden. Any of the chromatography resins produced by any of the methods described herein, any of the chromatography columns produced by any of the methods described herein, and any of the processes described herein can be aseptic and sterile, absolutely sterile, aseptic, or reduced bioburden.

Provided herein are methods of reducing bioburden of a chromatography resin that include: exposing a container including a composition including a chromatography resin and at least one antioxidant agent and/or chelator to a dose of gamma-irradiation sufficient to reduce the bioburden of the container and the chromatography resin, where the at least one antioxidant agent and/or chelator is present in an amount sufficient to ameliorate the loss of binding capacity of the chromatography resin after exposure to the dose of gamma-irradiation. Some embodiments of these methods further include, prior to exposing, disposing the composition into the container. In some examples, the irradiation is performed at a rate of between about 0.1 kGy/hour to about 6 kGy hour and/or at a temperature between about 4° C. to about 25° C. In some examples of any of these methods, the container is a storage vessel, a chromatography column, or a packed chromatography column. In some examples of any of the methods described herein, the composition is a slurry of sedimented chromatography resin in a liquid including the at least one antioxidant agent and/or chelator. In some examples, the liquid comprises: (i) between 75 mM and about 125 mM (e.g., between 80 mM and about 120 mM, between about 85 mM and about 115 mM, between about 90 mM and about 110 mM, or between about 95 mM and about 105 mM) mannitol; (ii) between 75 mM and about 125 mM (e.g., between about 80 mM and about 120 mM, between about 85 mM and about 115 mM, between about 90 mM and about 110 mM, or between about 95 mM and about 105 mM) methionine (or alternatively cysteine or glutathione); (iii) between 75 mM and about 125 mM (e.g., between about 80 mM and about 120 mM, between about 85 mM and about 115 mM, between about 90 mM and about 110 mM, or between about 95 mM and about 105 mM) sodium ascorbate; (iv) between 75 mM and about 125 mM (e.g., between about 80 mM and about 120 mM, between about 85 mM and about 115 mM, between about 90 mM and about 110 mM, or between about 95 mM and about 105 mM) histidine; (v) between 30 mM and about 70 mM (e.g., between about 35 mM and about 65 mM, between about 40 mM and about 60 mM, or between about 45 mM and about 55 mM) methionine (or alternatively cysteine or glutathione) and between about 30 mM and about 70 mM (e.g., between about 35 mM and about 65 mM, between about 40 mM and about 60 mM, or between about 45 mM and about 55 mM) histidine; (vi) between about 10 mM and about 50 mM (e.g., between about 15 mM and about 45 mM, between about 20 mM and about 40 mM, or between about 25 mM and about 35 mM) methionine (or alternatively cysteine or glutathione), between about 10 mM and about 50 mM (e.g., between about 15 mM and about 45 mM, between about 20 mM and about 40 mM, or between about 25 mM and about 35 mM) histidine, and between about 10 mM and about 50 mM (e.g., between about 15 mM and about 45 mM, between about 20 mM and about 40 mM, or between about 25 mM and about 35 mM) sodium ascorbate; or (vii) between about 5 mM to about 45 mM (e.g., between about 10 mM and about 40 mM, between about 15 mM and about 35 mM, or between about 20 mM and about 30 mM) sodium ascorbate, between about 5 mM and about 45 mM (e.g., between about 10 mM and about 40 mM, between about 15 mM and about 35 mM, or between about 20 mM and about 30 mM) methionine (or alternatively cysteine or glutathione), between about 5 mM and about 45 mM (e.g., between about 10 mM and about 40 mM, between about 15 mM and about 35 mM, or between about 20 mM and about 30 mM) mannitol, and between about 5 mM and about 45 mM (e.g., between about 10 mM and about 40 mM, between about 15 mM and about 35 mM, or between about 20 mM and about 30 mM) histidine. In some examples, the liquid is a buffered solution (e.g., a phosphate buffered solution, e.g., a sodium phosphate buffered solution, such as 50 mM sodium phosphate, pH 6.0).

In some examples of any of the methods described herein, the composition is a solid mixture. In some embodiments of any of the methods described herein, the composition includes at least one antioxidant agent selected from the group of: reduced glutathione, reduced thioredoxin, reduced cysteine, a carotenoid, melatonin, lycopene, tocopherol, reduced ubiquinone, ascorbate, bilirubin, uric acid, lipoic acid, a flavonoid, a phenolpropanoid acid, lidocaine, naringenin, fullerene, glucose, mannitol, 4-hydroxy-2,2,6,6-tetramethylpiperidin-1-oxyl, and dimethylmethoxy chromanol. In some embodiments of any of the methods described herein, the composition includes at least one (one, two, three, or four) antioxidant agent selected from mannitol, sodium ascorbate, methionine (or alternatively cysteine or glutathione), and histidine. In some embodiments, the composition includes mannitol, sodium ascorbate, methionine (or alternatively cysteine or glutathione), and histidine. In some embodiments of any of the methods described herein, the composition includes at least one chelator selected from the group of: ethylenediaminetetraacetic acid (EDTA), 2,3-dimercapto-1-propanesulfonic acid sodium (DMPS), dimercaptosuccinic acid (DMSA), metallothionin, and desferroxamine.

In some examples of any of the methods described herein, the composition includes at least one chromatography resin selected from the group of: anionic exchange chromatography resin, cationic exchange chromatography resin, affinity or pseudo-affinity chromatography resin, hydrophobic interaction chromatography resin, and size exclusion chromatography resin (or any combination thereof). In some examples of any of the methods described herein, the chromatography resin can be multi-modal (e.g., bi-modal) chromatography resin (e.g., a chromatography resin that has anionic exchange and hydrophobic interaction groups, or a chromatography resin that has both cation exchange and hydrophobic interaction groups). In some examples of any of the methods described herein, the composition includes affinity chromatography resin including a protein ligand (e.g., protein A or protein G). In some examples of any of the methods described herein, the composition includes an anionic exchange chromatography resin (e.g., an anionic exchange chromatography resin including N-benzyl-N-methyl-ethanolamine groups).

In some examples of any of the methods described herein, the dose is between about 2 kGy to about 45 kGy (e.g., between about 20 kGy to about 30 kGy, between about 23 kGy and about 27 kGy, between about 2 kGy to about 40 kGy, between about 2 kGy and about 35 kGy, between about 2 kGy and about 30 kGy, between about 2 kGy and about 25 kGy, between about 10 kGy and about 45 kGy, between about 10 kGy and about 40 kGy, between about 10 kGy and about 35 kGy, between about 10 kGy and about 30 kGy, or between about 10 kGy and about 25 kGy). In some embodiments of any of the methods described herein, the exposing is performed at a temperature between about $-25°$ C. and about $0°$ C., inclusive, or between about $0°$ C. and about $25°$ C., inclusive (e.g., between about $4°$ C. and about $25°$ C.).

Also provided is a reduced bioburden chromatography resin produced by any of the methods described herein. In some examples of any of the reduced bioburden bioburden chromatography resins provided herein have a sterility assurance level (SAL) of between about $1\times10^{-8}$ to about $1\times10^{-5}$ (e.g., between about $1\times10^{-7}$ to about $1\times10^{-6}$). For example, a chromagraphy resin produced by any of the methods described herein can have reduced bioburden, is sterile, is aseptic, or is absolutely sterile. In some embodiments, a chromatography resin produced by any of the methods described herein can be aseptic and have reduced bioburden, be sterile, or be absolutely sterile. Some examples of any of the reduced bioburden chromatography resins provided herein include at least one resin selected from the group of: anionic exchange chromatography resin, cationic exchange chromatography resin, affinity or pseudo-affinity chromatography resin, hydrophobic interaction chromatography resin, and size exclusion chromatography resin. In some embodiments, the reduced bioburden chromatography resin provided herein includes affinity chromatography resin including a protein ligand (e.g., protein A or protein G). In some embodiments, the reduced bioburden chromatography resin provided herein includes anionic exchange chromatography resin (e.g., an anionic exchange chromatography resin including N-benzyl-N-methyl-ethanolamine groups). In some embodiments, the reduced bioburden chromatography resin provided herein is multi-modal chromatography resin (e.g., a bimodal chromatography resin).

Also provided are methods of making a reduced bioburden packed chromatography column that include: providing any of the reduced bioburden chromatography resins produced by any of the methods described herein; and packing the chromatography resin into a reduced bioburden column in an aseptic environment. Also provided are reduced bioburden packed chromatography columns that are produced by gamma-irradiating a composition including a packed chromatography resin and at least one antioxidant agent and/or chelator (e.g., any of the exemplary compositions provided herein) included within a chromatography column. Any of the reduced bioburden packed chromatography columns provided herein can have a sterility assurance level (SAL) of between about $1\times10^{-8}$ to about $1\times10^{-5}$ (e.g., between about $1\times10^{-7}$ to about $1\times10^{-6}$). Any of the chromatography columns produced by any of the methods described herein can have reduced bioburden, be sterile, be absolutely sterile, or be aseptic. For example, any of the chromatography columns produced by any of the methods described herein can be aseptic and can have reduced bioburden, be sterile, or be absolutely sterile.

In some embodiments of any of the reduced packed chromatography columns provided herein, the resin in the packed column includes at least one resin selected from the group of: anionic exchange chromatography resin, cationic exchange chromatography resin, affinity chromatography resin, hydrophobic interaction chromatography resin, and size exclusion chromatography resin. In some embodiments of any of the reduced bioburden packed chromatography columns provided herein, the resin includes affinity chromatography resin including a protein ligand (e.g., protein A or protein G). In some examples of any of the reduced bioburden packed chromatography columns provided herein, the resin includes anionic exchange chromatography resin (e.g., an anionic exchange chromatography resin includes N-benzyl-N-methyl-ethanolamine groups).

Also provided are compositions including a chromatography resin and at least one antioxidant agent and/or chelator, where the at least one antioxidant agent and/or chelator is present in an amount sufficient to ameliorate the loss of binding capacity of the chromatography resin upon treatment with a dose of gamma-irradiation sufficient to reduce bioburden of the composition. In some examples of any of the compositions provided herein, the composition is a slurry of sedimented chromatography resin in a liquid including the at least one antioxidant agent and/or chelator. In some examples, the liquid comprises: (i) between 75 mM and about 125 mM (e.g., between 80 mM and about 120 mM, between about 85 mM and about 115 mM, between about 90 mM and about 110 mM, or between about 95 mM and about 105 mM) mannitol; (ii) between 75 mM and about 125 mM (e.g., between about 80 mM and about 120 mM, between about 85 mM and about 115 mM, between about 90 mM and about 110 mM, or between about 95 mM and about 105 mM) methionine (or alternatively cysteine or glutathione); (iii) between 75 mM and about 125 mM (e.g., between about 80 mM and about 120 mM, between about 85 mM and about 115 mM, between about 90 mM and about 110 mM, or between about 95 mM and about 105 mM) sodium ascorbate; (iv) between 75 mM and about 125 mM (e.g., between about 80 mM and about 120 mM, between about 85 mM and about 115 mM, between about 90 mM and about 110 mM, or between about 95 mM and about 105 mM) histidine; (v) between 30 mM and about 70 mM (e.g., between about 35 mM and about 65 mM, between about 40 mM and about 60 mM, or between about 45 mM and about 55 mM) methionine (or alternatively cysteine or glutathione) and between about 30 mM and about 70 mM (e.g., between about 35 mM and about 65 mM, between about 40 mM and about 60 mM, or between about 45 mM and about 55 mM) histidine; (vi) between about 10 mM and about 50 mM (e.g., between about 15 mM and about 45 mM, between about 20 mM and about 40 mM, or between about 25 mM and about 35 mM) methionine (or alternatively cysteine or glutathione), between about 10 mM and about 50 mM (e.g., between about 15 mM and about 45 mM, between about 20 mM and about 40 mM, or between about 25 mM and about 35 mM) histidine, and between about 10 mM and about 50 mM (e.g., between about 15 mM and about 45 mM, between about 20 mM and about 40 mM, or between about 25 mM and about 35 mM) sodium ascorbate; or (vii) between about 5 mM to about 45 mM (e.g., between about 10 mM and about 40 mM, between about 15 mM and about 35 mM, or between about 20 mM and about 30 mM) sodium ascorbate, between about 5 mM and about 45 mM (e.g., between about 10 mM and about 40 mM, between about 15 mM and about 35 mM, or between about 20 mM and about 30 mM) methionine (or alternatively cysteine or glutathione), between about 5 mM and about 45 mM (e.g., between about 10 mM and about 40 mM, between about 15 mM and about 35 mM, or between about 20 mM and about 30 mM) mannitol, and between about 5 mM and about 45 mM (e.g., between about 10 mM and about 40 mM, between about 15 mM and about 35 mM, or between about 20 mM and about 30 mM) histidine. In some examples, the liquid is a buffered solution (e.g., a phosphate buffered solution, e.g., a sodium phosphate buffered solution, such as 50 mM sodium phosphate, pH 6.0).

In some examples of any of the compositions provided herein, the composition is a solid mixture.

Some embodiments of any of the compositions provided herein can include at least one antioxidant agent selected from the group of: reduced glutathione, reduced thioredoxin, reduced cysteine, a carotenoid, melatonin, lycopene, tocopherol, reduced ubiquinone, ascorbate, bilirubin, uric acid, lipoic acid, a flavonoid, a phenolpropanoid acid, lidocaine, naringenin, fullerene, glucose, mannitol, 4-hydroxy-2,2,6,6-tetramethylpiperidin-1-oxyl, and dimethylmethoxy chromanol. Some embodiments of any of the compositions provided herein can include at least one (one, two, three, or four) antioxidant agents selected from mannitol, sodium ascorbate, methionine (or alternatively cysteine or glutathione), and histidine. Some examples of any of the compositions provided herein include mannitol, sodium ascorbate, methionine (or alternatively cysteine or glutathione), and histidine. Some examples of any of the compositions provided herein can include at least one chelator selected from the group of: ethylenediaminetetraacetic acid (EDTA), 2,3-dimercapto-1-propanesulfonic acid sodium (DMPS), dimercaptosuccinic acid (DMSA), metallothionin, and desferroxamine. In some examples of any of the compositions provided herein, the chromatography resin can include at least one resin selected from the group of: anionic exchange chromatography resin, cationic exchange chromatography resin, affinity chromatography resin, hydrophobic interaction chromatography resin, and size exclusion chromatography resin. In some examples of any of the compositions provided herein, the resin includes affinity chromatography resin including a protein ligand (e.g., protein A or protein G).

Also provided are methods of performing reduced bioburden column chromatography that includes: (a) providing any of the reduced bioburden packed chromatography columns produced by any of the methods described herein; and (b) performing column chromatography using the reduced bioburden packed chromatography column and reduced bioburden buffer in a closed system. In some examples of any of the methods described herein, reduced bioburden column chromatography using the reduced bioburden packed chromatography column is performed continuously for a period of at least 4 days (e.g., at least 5 days, at least 7 days, at least 14 days, at least 28 days, or at least 60 days). In some embodiments of any of the methods described herein, the resin in the reduced bioburden packed chromatography column in (a) has a percentage binding capacity of between about 65% and about 100% (e.g., between about 75% and about 100%) as compared to the same resin not treated with gamma-irradiation. In some embodiments of any of the methods described herein, the resin in the reduced bioburden packed chromatography column includes at least one resin selected from the group of: anionic exchange chromatography resin, cationic exchange chromatography resin, affinity or pseudo-affinity chromatography resin, hydrophobic interaction chromatography resin, and size exclusion chromatography resin. In some examples of any of the methods described herein, the resin includes affinity chromatography resin including a protein ligand (e.g., protein A or protein G). In some embodiments of any of the methods described herein, the resin includes anionic exchange chromatography resin.

Also provided are integrated, closed or substantially closed, and continuous processes for reduced bioburden manufacturing of a purified recombinant protein that include: (a) providing a liquid culture medium including a recombinant protein that is substantially free of cells; and (b) continuously feeding the liquid culture medium into a multi-column chromatography system (MCCS) including at least one of any of the reduced bioburden packed chromatography columns produced any of the methods described herein; where the process utilizes reduced bioburden buffer, is integrated, and runs continuously from the liquid culture medium to an eluate from the MCCS that is the purified recombinant protein. In some embodiments of any of the processes described herein, the MCCS performs at least two different unit operations. In some embodiments of any of the processes described herein, the process includes column switching. In some examples of any of the processes described herein, the MCCS performs the unit operations of capturing the recombinant protein and inactivating viruses, or performs the unit operations of capturing and purifying the recombinant protein.

In some embodiments of any of the processes described herein, the MCCS includes at least two reduced bioburden packed chromatography columns. In some examples of any of the processes described herein, the MCCS is a periodic counter current chromatography system. In some examples of any of the processes described herein, the MCCS includes a plurality of columns for affinity chromatography, cation exchange chromatography, anion exchange chromatography, or size exclusion chromatography, or any combination thereof. In some embodiments of any of the methods described herein, the MCCS includes a column for affinity chromatography, and affinity chromatography is performed in the process with a capture mechanism selected from the group of: protein A-binding capture mechanism, substrate-binding capture mechanism, antibody- or antibody fragment-binding capture mechanism, aptamer-binding capture mechanism, and cofactor-binding capture mechanism. In some examples of any of the processes described herein, the affinity chromatography is performed in the process with a protein A-binding capture mechanism, and the recombinant protein is an antibody or an antibody fragment.

Also provided are integrated, closed or substantially closed, and continuous processes for reduced bioburden manufacturing of a purified recombinant protein that include: (a) providing a liquid culture medium including a recombinant protein that is substantially free of cells; (b) continuously feeding the liquid culture medium into a first multi-column chromatography system (MCCS1); (c) capturing the recombinant protein in the liquid culture medium using the MCCS1; (d) producing an eluate from the MCCS1 that includes the recombinant protein and continuously feeding the eluate into a second multi-column chromatography system (MCCS2); (e) continuously feeding the recombinant protein from the eluate into the MCCS2 and subsequently eluting the recombinant protein to thereby produce the purified recombinant protein, where: the process utilizes reduced bioburden buffer, is integrated, and runs continuously from the liquid culture medium to the purified recombinant protein, and at least one column in the MCCS1 and/or MCCS2 contains at least one of any of the reduced bioburden packed chromatography columns produced by any of the methods described herein. In some embodiments of any of the processes described herein, the MCCS1 and/or the MCCS2 performs at least two different unit operations. Some examples of any of the processes described herein involve column switching. In some examples of any of the processes described herein, the MCCS1 performs the unit operations of capturing the recombinant therapeutic protein and inactivating viruses. In some embodiments of any of the processes provided herein, the MCCS2 performs the unit operations of purifying and polishing the recombinant protein. In some embodiments of any of the processes provided herein, the MCCS1 and/or MCCS2 includes at least two chromatography columns. In some examples of any of the processes described herein, the MCCS1 is a first periodic counter current chromatography system (PCCS1). In some examples of any of the processes described herein, the capturing is performed using affinity chromatography, cation exchange chromatography, anion exchange chromatography, or size exclusion chromatography, or any combination thereof. In some examples of any of the processes described herein, the affinity chromatography is performed with a capture mechanism selected from the group of: protein A-binding capture mechanism, substrate-binding capture mechanism, antibody- or antibody fragment-binding capture mechanism, aptamer-binding capture mechanism, and cofactor-binding capture mechanism. In some embodiments of any of the processes described herein, the affinity chromatography is performed with a protein-A binding capture mechanism, and the recombinant protein is an antibody or an antibody fragment.

In some embodiments of any of the processes described herein, the MCCS2 is a second periodic counter current (PCCS2) chromatography system. In any of the processes described herein, the recombinant protein is a therapeutic recombinant protein. Some embodiments of any of the processes described herein further include formulating the purified therapeutic recombinant protein into a pharmaceutical composition. Some embodiments of any of the processes described herein can be performed continuously for a period of at least 4 days (e.g., at least 5 days, at least 7 days, at least 14 days, or at least 28 days).

Also provided are methods of reducing bioburden of a chromatography comprising (a) exposing a container comprising a substantially dry chromatography resin to a dose of gamma-irradiation sufficient to reduce the bioburden of the container and the chromatography resin. Some embodiments of these methods further comprise prior to step (a) drying a chromatography resin to remove liquid from the chromatography resin. In some embodiments, the substantially dry chromatography resin does not contain a significant amount of an antioxidant agent or a significant amount of a chelator. In some embodiments, the container is a storage vessel. In some embodiments, the chromatography resin is covalently attached to a surface of an article (e.g., a chip, membrane, or cassette). In some embodiments, the chromatography resin comprises a protein ligand (e.g., protein A or protein G). In some embodiments, the chromatography resin is an anionic exchange chromatography resin (e.g., a chromatography resin comprising N-benzyl-N-methyl-ethanolamine groups). In some embodiments, the dose is between about 15 kGy to about 45 kGy (e.g., between about 20 kGy to about 30 kGy). Also provided are reduced bioburden chromatography resins produced by any of the methods described herein. In some embodiments, the reduced bioburden chromatography resin produced has a sterility assurance level (SAL) of between about $1\times10^{-8}$ to about $1\times10^{-5}$ (e.g., a SAL of between about $1\times10^{-7}$ to about $1\times10^{-6}$). In some embodiments, the reduced chromatography resin comprises at least one resin selected from the group of: anionic exchange chromatography resin, cationic exchange chromatography resin, affinity chromatography resin, hydrophobic interaction chromatography resin, and size exclusion chromatography resin. In some embodiments, the reduced chromatography resin comprises an affinity chromatography resin comprising a protein ligand (e.g., protein A). In some embodiments, the reduced chromatography resin comprises an anionic exchange chromatography resin (e.g., an anionic exchange chromatography resin comprising N-benzyl-N-methyl-ethanolamine groups). Also provided are methods of making a reduced bioburden packed chromatography column that comprise providing the reduced bioburden chromatography resin produced by any of the methods described herein; and packing the chromatography resin into a reduced bioburden column in an aseptic environment. Also provided are reduced bioburden packed chromatography columns produced by any of the methods described herein.

Also provided are integrated, closed, and continuous processes for reduced bioburden manufacturing of a purified recombinant protein comprising: (a) providing a liquid culture medium comprising a recombinant protein that is substantially free of cells; and (b) continuously feeding the liquid culture medium into a multi-column chromatography system (MCCS) comprising at least one reduced bioburden packed chromatography column produced by any of the methods provided herein; where the process utilizes reduced bioburden buffer, is integrated, and runs continuously from the liquid culture medium to an eluate from the MCCS that is the purified recombinant protein. Also provided are integrated, closed, and continuous processes for reduced bioburden manufacturing of a purified recombinant protein comprising: (a) providing a liquid culture medium comprising a recombinant protein that is substantially free of cells; (b) continuously feeding the liquid culture medium into a first multi-column chromatography system (MCCS1); (c) capturing the recombinant protein in the liquid culture medium using the MCCS1; (d) producing an eluate from the MCCS1 that comprises the recombinant protein and continuously feeding the eluate into a second multi-column chromatography system (MCCS2); (e) continuously feeding the recombinant protein from the eluate into the MCCS2 and subsequently eluting the recombinant protein to thereby produce the purified recombinant protein, wherein: the process utilizes reduced bioburden buffer, is integrated, and runs continuously from the liquid culture medium to the purified recombinant protein, and at least one column in the MCCS1 and/or MCCS2 contains a reduced bioburden packed chromatography column produced by any of the methods provided herein.

As used herein, the word "a" before a noun represents one or more of the particular noun. For example, the phrase "a reduced bioburden chromatography column" represents "one or more reduced bioburden chromatography columns."

The term "bioburden" is art known and refers to the level of self-replicating biological contaminants present in a composition (e.g., solid or liquid) and/or on the surface (e.g., exterior and/or interior surface) of an article(s). For example, bioburden can refer to self-replicating biological contaminants present in a composition containing a chromatography resin or a packed chromatography resin (e.g., self-replicating biological contaminants present in a packed chromatography resin in a packed chromatography column). In other examples, bioburden can refer to self-replicating biological contaminants on the inner surface of a chromatography column and/or within the chromatography resin within the chromatography column (e.g., biological contaminants on the inner surface of a chromatography column and biological contaminants in the packed chromatography resin within the chromatography column). Bioburden can also refer to the self-replicating biological contaminants present within a liquid (e.g., a buffer used in any of the methods or processes described herein). Non-limiting examples of self-replicating biological contaminants can be bacteria (e.g., Gram-positive or Gram-negative bacteria, or a bacterial spore), mycobacteria, viruses (e.g., a vesivirus, a Cache Valley virus, a parvovirus, a herpes virus, and a bunyavirus), parasites, fungi, yeast, and protozoa. Exemplary methods for determining bioburden are described herein. Additional methods for determining bioburden are known in the art.

The term "reducing bioburden" is art known and refers to a decrease (e.g., a detectable decrease) in the level of self-replicating biological contaminants present in a composition (e.g., solid or liquid) and/or on the surface (e.g., exterior and/or interior surface) of an article(s). Non-limiting examples of methods for reducing bioburden of a chromatography resin (e.g., packed chromatography resin), buffer, and/or a chromatography column (e.g., a packed chromatography column) are described herein. Additional methods for reducing bioburden of any of the compositions described herein are known in the art.

The term "reduced bioburden chromatography resin" means a chromatography resin that has been treated to decrease the level of self-replicating biological contaminants present in the chromatography resin (e.g., a detectable decrease in the level of self-replicating biological contaminants present in a composition containing a chromatography resin, e.g., a slurry). For example, reduced bioburden chromatography resin can be a resin exposed to gamma-irradiation in a dose sufficient to decrease the level of self-replicating biological contaminants in the chromatography resin (e.g., a composition containing a chromatography resin exposed to gamma-irradiation in a dose sufficient to decrease the level of self-replicating biological contaminants in the chromatography resin). For example, a reduced bioburden chromatography resin can be a resin that has been exposed to a dose of between about 1 kGy to about 15 kGy, between about 1 kGy and about 20 kGy gamma-irradiation, between about 1 kGy and about 25 kGy gamma-irradiation, between about 1 kGy and about 30 kGy gamma-irradiation, or between about 1 kGy and about 35 kGy gamma-irradiation. Exemplary methods for reducing bioburden of a chromatography resin are described herein. Additional methods for reducing the bioburden of a chromatography resin are known in the art.

The term "reduced bioburden chromatography column" means a chromatography column (e.g., a packed chromatography column) that includes a treated chromatography resin (e.g., gamma-irradiated chromatography resin), that has a level of self-replicating biological contaminants that is less than the level of self-replicating biological contaminants present in an identical chromatography column that includes an untreated chromatography resin. For example, a reduced bioburden chromatography column can include a treated chromatography resin having a sterility assurance level of at least or about $1\times10^{-6}$, $1\times10^{-7}$, $1\times10^{-8}$, $1\times10^{-9}$, or $1\times10^{-10}$.

The term "reduced bioburden buffer" is art known and means a treated (e.g., filtered, autoclaved, and/or gamma-irradiated) liquid (e.g., a treated buffered solution) that has a level of self-replicating contaminating agent(s) that is less than the level of self-replicating contaminating agent(s) found in an identical untreated liquid. For example, a reduced bioburden buffer can have a sterility assurance level of at least or about $1 \times 10^{-6}$, $1 \times 10^{-7}$, $1 \times 10^{-8}$, $1 \times 10^{-9}$, or $1 \times 10^{-10}$.

"Absolute sterility" or "absolutely sterile" are terms used to describe a composition or process that is/are completely free of self-replicating biological contaminants. For example, the term can apply to a gamma-irradiated chromatography resin, the interior surface and contents (e.g., chromatography resin) of a chromatography column, and/or a buffer. An absolutely sterile composition or process can be clean (as that term is known in the art).

"Sterile" or "sterility" are terms used to describe a composition or process that have a sterility assurance level of about or less than $1.0 \times 10^{-6}$ (e.g., about or less than $1.0 \times 10^{-7}$, about or less than $1.0 \times 10^{-8}$, about or less than $1.0 \times 10^{-9}$, or $1 \times 10^{-10}$). The determination of whether a composition or process is sterile can be tested using a number of validated production processes known in the art. For example, a sterile composition or process can be completely free of viable self-replicating biological contaminants (e.g., any of the self-replicating biological contaminants described herein). A sterile composition or process can also be clean (as that term is known in the art).

The term "sterilization" means a validated process used to render a composition sterile (as defined herein). The inactivation rate of resistant indicator self-replicating biological contaminants (e.g., bacteria) during a treatment process can be measured in order to determine whether sterility (as defined herein) has been achieved for a composition.

The term "sterility assurance level" or "SAL" is art-known and means a level of confidence of achieving absolute sterility within a batch of treated units. The probability is usually calculated based on the results of inactivation studies performed during validation and expressed in the form of $1 \times 10^{-n}$.

The term "aseptic" is used to describe a composition or process that is free of disease-causing or symptom-causing self-replicating biological contaminants (e.g., any of the self-replicating biological contaminants described herein). An aseptic composition or process can also be clean (as that term is known in the art).

The term "unit operation" is a term of art and means a functional step that can be performed in a process of purifying a recombinant protein from a liquid culture medium. For example, a unit of operation can be filtering (e.g., removal of contaminant bacteria, yeast, viruses, and/or mycobacteria, and/or particulate matter from a fluid including a recombinant protein), capturing, epitope tag removal, purifying, holding or storing, polishing, virus inactivating, adjusting the ionic concentration and/or pH of a fluid including the recombinant protein, and removing unwanted salts.

The term "capturing" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight) and concentrate a recombinant protein (e.g., a recombinant therapeutic protein) from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a chromatography resin that binds a recombinant protein (e.g., through the use of affinity chromatography). Non-limiting methods for capturing a recombinant protein from a liquid culture medium or diluted liquid culture medium are described herein and others are known in the art. A recombinant protein can be captured from a liquid culture medium using at least one chromatography column and/or chromatographic membrane (e.g., any of the chromatography columns and/or chromatographic membranes described herein).

The term "purifying" means a step performed to isolate a recombinant protein (e.g., a recombinant therapeutic protein) from one or more other impurities (e.g., bulk impurities) or components present in a fluid including a recombinant protein (e.g., liquid culture medium proteins or one or more other components (e.g., DNA, RNA, other proteins, endotoxins, viruses, etc.) present in or secreted from a mammalian cell). For example, purifying can be performed during or after an initial capturing step. Purification can be performed using a chromatography resin, membrane, or any other solid support that binds either a recombinant protein or contaminants (e.g., through the use of affinity chromatography, hydrophobic interaction chromatography, anion or cation exchange chromatography, or molecular sieve chromatography). A recombinant protein can be purified from a fluid including the recombinant protein using at least one chromatography column and/or chromatographic membrane (e.g., any of the chromatography columns or chromatographic membranes described herein).

The term "polishing" is a term of art and means a step performed to remove remaining trace or small amounts of contaminants or impurities from a fluid including a recombinant protein (e.g., a recombinant therapeutic protein) that is close to a final desired purity. For example, polishing can be performed by passing a fluid including the recombinant protein through a chromatographic column(s) or membrane absorber(s) that selectively binds to either the target recombinant protein or small amounts of contaminants or impurities present in a fluid including a recombinant protein. In such an example, the eluate/filtrate of the chromatographic column(s) or membrane absorber(s) includes the recombinant protein.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the processes described herein).

The term "eluate/filtrate" is a term of art and means a fluid that is emitted from a chromatography column or chromatographic membrane that includes a detectable amount of a recombinant protein (e.g., a recombinant therapeutic protein).

The term "integrated process" means a process which is performed using structural elements that function cooperatively to achieve a specific result (e.g., the purification of a recombinant protein from a liquid culture medium).

The term "continuous process" means a process which continuously feeds fluid through at least a part of the system. For example, a continuous process is a process which continuously feeds a liquid culture medium including a recombinant protein from a bioreactor through a MCCS. Another example of a continuous process is a process which continuously feeds a liquid culture medium including a recombinant protein from a bioreactor through a first and second MCCS (MCCS1 and MCCS2). Additional examples include a process which continuously feeds a liquid culture medium including a recombinant protein through a MCCS, a process that continuously feeds a liquid culture medium including a recombinant protein through a MCCS1 and a MCCS2, or a process that continuously feeds a fluid including a recombinant protein through a MCCS2.

The term "closed process" is a term of art and means a process that is performed such that components of the process (e.g., chromatography resins and/or buffers) that come into contact with the recombinant protein or liquids including the recombinant protein are not intentionally exposed to contaminating agents for a significant period of time (e.g., not intentionally air-exposed for a significant period of time).

The term "therapeutic protein drug substance" means a recombinant protein (e.g., an immunoglobulin, protein fragment, engineered protein, or enzyme) that has been sufficiently purified or isolated from contaminating proteins, lipids, and nucleic acids (e.g., contaminating proteins, lipids, and nucleic acids present in a liquid culture medium or from a host cell (e.g., from a mammalian, yeast, or bacterial host cell)) and biological contaminants (e.g., viral and bacterial contaminants), and can be formulated into a pharmaceutical agent without any further substantial purification and/or decontamination step(s).

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) including a total of two or more interconnected or switching chromatography columns and/or chromatographic membranes. Additional examples of multi-column chromatography systems are described herein and are known in the art.

The term "substantially free" means a composition (e.g., a liquid culture medium) that is at least or about 90% free (e.g., at least or about 95%, 96%, 97%, 98%, or at least or about 99% free, or about 100% free) of a specified substance (e.g., a mammalian cell or a contaminating protein, nucleic acid, carbohydrate, or lipid form a mammalian cell).

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. Additional examples of mammalian cells are known in the art.

The term "culturing" or "cell culturing" means the maintenance or proliferation of a mammalian cell under a controlled set of physical conditions.

The term "culture of mammalian cells" means a liquid culture medium including a plurality of mammalian cells that is maintained or proliferated under a controlled set of physical conditions.

The term "liquid culture medium" means a fluid that includes sufficient nutrients to allow a cell (e.g., a mammalian cell) to grow or proliferate in vitro. For example, a liquid culture medium can include one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can include serum from a mammal. In some embodiments, a liquid culture medium does not include serum or another extract from a mammal (a defined liquid culture medium). In some embodiments, a liquid culture medium can include trace metals, a mammalian growth hormone, and/or a mammalian growth factor. Another example of liquid culture medium is minimal medium (e.g., a medium including only inorganic salts, a carbon source, and water). Non-limiting examples of liquid culture medium are described herein. Additional examples of liquid culture medium are known in the art and are commercially available. A liquid culture medium can include any density of mammalian cells. For example, as used herein, a volume of liquid culture medium removed from a bioreactor can be substantially free of mammalian cells.

The term "animal-derived component free liquid culture medium" means a liquid culture medium that does not include any components (e.g., proteins or serum) derived from a mammal.

The term "serum-free liquid culture medium" means a liquid culture medium that does not include a mammalian serum.

The term "serum-containing liquid culture medium" means a liquid culture medium that includes a mammalian serum.

The term "chemically-defined liquid culture medium" is a term of art and means a liquid culture medium in which all of the chemical components are known. For example, a chemically-defined liquid culture medium does not include fetal bovine serum, bovine serum albumin, or human serum albumin, as these preparations typically include a complex mix of albumins and lipids.

The term "protein-free liquid culture medium" means a liquid culture medium that does not include any protein (e.g., any detectable protein).

The term "immunoglobulin" means a polypeptide including an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, and/or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM), e.g., a subclass of IgG (e.g., IgG1, IgG2, IgG3, or IgG4). The immunoglobulin may be an antibody fragment, e.g., a Fab fragment, a F(ab')$_2$ fragment, or an scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein including at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that include at least one recombinant scaffolding sequence.

The term "secreted protein" or "secreted recombinant protein" means a protein (e.g., a recombinant protein) that originally included at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein.

The term "perfusion bioreactor" means a bioreactor including a plurality of cells (e.g., mammalian cells) in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch bioreactor" is a term of art and means a bioreactor including a plurality of cells (e.g., mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

The term "clarified liquid culture medium" means a liquid culture medium obtained from a bacterial or yeast cell culture that is substantially free (e.g., at least 80%, 85%, 90%, 92%, 94%, 96%, 98%, or 99% free) of bacteria or yeast cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 10 is a list of exemplary recombinant proteins that are enzymes that can be used to treat specific disorders in humans.

DETAILED DESCRIPTION

Figures 1, 2:
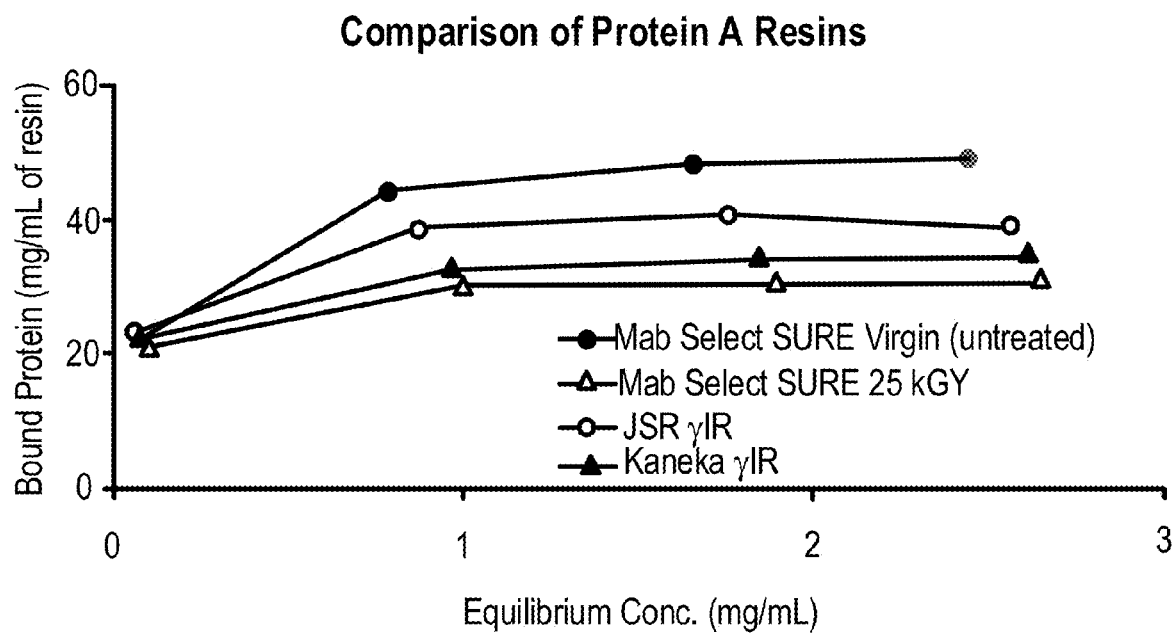
FIG. 1 is a graph showing the static binding curve of resin (mg/mL protein) for untreated GE Mab Select SuRe™ resin, 25 kGy gamma-irradiated GE Mab Select SuRe™ resin, 15 kGy gamma-irradiated JSR LifeSciences Amsphere ProA JWT203 resin, and 15 kGy gamma-irradiated Kaneka Kan-Cap A resin.
FIG. 2 is a table showing the 280 nm absorbance (protein A absorbance) of supernatant from GE Mab Select SuRe™ resin following 30 kGy gamma-irradiation and from JSR LifeSciences Amsphere ProA JWT203 resin following 30 kGy gamma-irradiation.

Provided herein are methods of reducing bioburden of a chromatography resin that include exposing a container including a composition including a chromatography resin and at least one antioxidant agent and/or chelator to a dose of gamma-irradiation sufficient to reduce the bioburden of the container and the chromatography resin, where the at least one antioxidant agent and/or chelator are present in an amount sufficient to ameliorate the loss of binding capacity of the chromatography resin after/upon exposure to the dose of gamma-irradiation. Also provided are reduced bioburden chromatography columns containing a reduced bioburden chromatography resin prepared by any of the methods described herein, compositions including a chromatography resin and at least one chelator and/or antioxidant agent, methods of performing reduced bioburden column chromatography using at least one of these reduced bioburden chromatography columns, and integrated, closed or substantially closed, and continuous processes for reduced bioburden manufacturing of a purified recombinant protein that include the use of at least one of these reduced bioburden chromatography columns. Non-limiting aspects of these methods and processes are described below. As can be appreciated in the art, the various aspects described below can be used in any combination without limitation.

Compositions Containing Chromatography Resin and an Antioxidant and/or Chelator

Provided herein are compositions including a chromatography resin (e.g., any of the chromatography resins described herein or known in the art) and at least one antioxidant agent and/or chelator (e.g., any of the antioxidant agents and/or chelators described herein or known in the art), wherein the at least one antioxidant agent and/or chelator is present in an amount sufficient to ameliorate the loss of binding capacity of the chromatography resin upon treatment with a dose of gamma-irradiation sufficient to reduce bioburden of the composition. For example, the chromatography resin can be at least one of anionic exchange chromatography resin, cationic exchange chromatography resin, affinity or pseudo-affinity chromatography resin, hydrophobic interaction chromatography resin, and size exclusion chromatography resin, or any combination thereof. In some examples, the chromatography resin is a resin including a protein or peptide ligand (e.g., an affinity chromatography resin with a protein or peptide ligand, e.g., a protein A or protein G chromatography resin).

The composition, e.g., can be a slurry of sedimented chromatography resin in a liquid including the at least one antioxidant agent and/or chelator. For example, the liquid can contain at least one (e.g., one, two, three, or four) of methionine (or alternatively cysteine or glutathione), sodium ascorbate, histidine, and mannitol. In some examples, the liquid contains methionine (or alternatively cysteine or glutathione), sodium ascorbate, histidine, and mannitol. In some examples, the liquid comprises: (i) between 75 mM and about 125 mM (e.g., between 80 mM and about 120 mM, between about 85 mM and about 115 mM, between about 90 mM and about 110 mM, or between about 95 mM and about 105 mM) mannitol; (ii) between 75 mM and about 125 mM (e.g., between about 80 mM and about 120 mM, between about 85 mM and about 115 mM, between about 90 mM and about 110 mM, or between about 95 mM and about 105 mM) methionine (or alternatively cysteine or glutathione); (iii) between 75 mM and about 125 mM (e.g., between about 80 mM and about 120 mM, between about 85 mM and about 115 mM, between about 90 mM and about 110 mM, or between about 95 mM and about 105 mM) sodium ascorbate; (iv) between 75 mM and about 125 mM (e.g., between about 80 mM and about 120 mM, between about 85 mM and about 115 mM, between about 90 mM and about 110 mM, or between about 95 mM and about 105 mM) histidine; (v) between about 30 mM and about 70 mM (e.g., between about 35 mM and about 65 mM, between about 40 mM and about 60 mM, or between about 45 mM and about 55 mM) methionine (or alternatively cysteine or glutathione) and between about 30 mM and about 70 mM (e.g., between about 35 mM and about 65 mM, between about 40 mM and about 60 mM, or between about 45 mM and about 55 mM) histidine; (vi) between about 10 mM and about 50 mM (e.g., between about 15 mM and about 45 mM, between about 20 mM and about 40 mM, or between about 25 mM and about 35 mM) methionine (or alternatively cysteine or glutathione), between about 10 mM and about 50 mM (e.g., between about 15 mM and about 45 mM, between about 20 mM and about 40 mM, or between about 25 mM and about 35 mM) histidine, and between about 10 mM and about 50 mM (e.g., between about 15 mM and about 45 mM, between about 20 mM and about 40 mM, or between about 25 mM and about 35 mM) sodium ascorbate; or (vii) between about 5 mM to about 45 mM (e.g., between about 10 mM and about 40 mM, between about 15 mM and about 35 mM, or between about 20 mM and about 30 mM) sodium ascorbate, between about 5 mM and about 45 mM (e.g., between about 10 mM and about 40 mM, between about 15 mM and about 35 mM, or between about 20 mM and about 30 mM) methionine (or alternatively cysteine or glutathione), between about 5 mM and about 45 mM (e.g., between about 10 mM and about 40 mM, between about 15 mM and about 35 mM, or between about 20 mM and about 30 mM) mannitol, and between about 5 mM and about 45 mM (e.g., between about 10 mM and about 40 mM, between about 15 mM and about 35 mM, or between about 20 mM and about 30 mM) histidine. In some examples, the liquid is a buffered solution (e.g., a phosphate buffered solution, e.g., a sodium phosphate buffered solution, such as 50 mM sodium phosphate, pH 6.0). In some examples, the liquid is a buffered solution (e.g., a phosphate buffered solution, such as a sodium phosphate buffered solution (e.g., 50 mM sodium phosphate, pH 6.0).

In some examples, the composition can be a solid mixture (e.g., a dry solid mixture or a wetted or moist solid mixture). The solid mixture can include at least one (e.g., one, two, three, or four) of methionine (or alternatively cysteine or glutathione), sodium ascorbate, histidine, and mannitol. In some examples, the solid mixture contains methionine (or alternatively cysteine or glutathione), sodium ascorbate, histidine, and mannitol. In some examples, the composition is a chromatography resin packed in liquid including the at least one antioxidant agent and/or chelator. Non-limiting examples of such liquids are described herein.

Also provided herein is a container (e.g., a plastic container or a chromatography column) including a chromatography resin (e.g., any of the chromatography resins described herein or known in the art) and at least one antioxidant agent and/or chelator (e.g., any of the antioxidant agents and/or chelators described herein or known in the art), wherein the at least one antioxidant agent and/or chelator is present in an amount sufficient to ameliorate the loss of binding capacity of the chromatography resin upon treatment with a dose of gamma-irradiation sufficient to reduce bioburden of the composition. For example, the container (e.g., a plastic container or a chromatography column) can have an internal volume of, e.g., at least about 1 mL, 5 mL, at least about 10 mL, at least about 20 mL, at least about 30 mL, at least about 40 mL, at least about 50 mL, at least about 60 mL, at least about 70 mL, at least about 80 mL, at least about 90 mL, at least about 100 mL, at least about 110 mL, at least about 120 mL, at least about 130 mL, at least about 140 mL, at least about 150 mL, at least about 160 mL, at least about 170 mL, at least about 180 mL, at least about 190 mL, at least about 200 mL, at least about 210 mL, at least about 220 mL, at least about 230 mL, at least about 240 mL, at least about 250 mL, at least about 300 mL, at least 350 mL, at least about 400 mL, or at least about 500 mL. For example, a container can have an internal volume of, e.g., between about 1 mL and about 500 mL, between about 1 mL and about 50 mL, between about 5 mL and about 500 mL, between about 5 mL and about 400 mL, between about 5 mL and about 350 mL, between about 5 mL and about 300 mL, between about 5 mL and about 250 mL, between about 5 mL and about 200 mL, between about 5 mL and about 150 mL, between about 5 mL and about 100 mL, or between about 5 mL and about 50 mL. In some examples, the chromatography resin in the container is a slurry of sedimented chromatography resin in a liquid including the at least one antioxidant agent and/or chelator. In some examples, the container includes a packed chromatography resin (e.g., packed in a liquid including the at least one antioxidant agent and/or chelator).

Any of the compositions provided herein can contain at least one (e.g., 2, 3, 4, 5, 6, 7, 8, 9, or 10) antioxidant agent and/or at least one (e.g., 2, 3, 4, 5, 6, 7, 8, 9, or 10) chelator. Any of the antioxidant agent(s) included in any of the compositions provided herein can have the ability to quench one or more of the following reactive oxygen and/or nitrogen species: hydroxyl radical, carbonate radical, superoxide anion, peroxyl radical, peroxynitrite, nitrogen dioxide, and nitric oxide. Non-limiting examples of antioxidant agents that can be included in any of the compositions provided herein include: reduced glutathione, reduced thioredoxin, reduced cysteine, a carotenoid, melatonin, lycopene, tocopherol, reduced ubiquinone, ascorbate, bilirubin, uric acid, lipoic acid, a flavonoid, a phenolpropanoid acid, lidocaine, naringenin, fullerene, glucose, mannitol, 4-hydroxy-2,2,6,6-tetramethylpiperidin-1-oxyl, and dimethylmethoxy chromanol. Additional non-limiting examples of antioxidant agents include antioxidant enzymes (e.g., superoxide dismutase, glutathione peroxidase, glutathione reductase, catalase, and thioredoxin reductase). Additional examples of antioxidant agents that can be included in any of the compositions provided herein include mannitol, sodium ascorbate, methionine, and histidine. Further examples of antioxidant agents include cysteine, taurine, mercaptopropionylglycine, N-acetylcysteine, garlic oil, diallylsulfide, dihydrolipoic acid, and diallyltrisulfide. Some embodiments that include an antioxidant enzyme as an antioxidant agent can further include one or more substrate(s) for the enzyme. An antioxidant agent can be identified using a number of methods known in the art including, for example, spin trapping, redox sensitive dyes, and chemiluminescence assays.

Any of the chelator(s) included in any of the compositions provided herein can have the ability to bind a redox active metal (e.g., $Cu^{2+}$ and $Fe^{2+}$) with high affinity (e.g., about or less than 1 μM, about or less than 800 nM, about or less than 700 nM, about or less than 600 nM, about or less than 500 nM, about or less than 400 nM, about or less than 300 nM, about or less than 250 nM, about or less than 200 nM, about or less than 150 nM, about or less than 100 nM, about or less than 80 nM, about or less than 60 nM, about or less than 40 nM, about or less than 20 nM, or about or less than 1 nm). Non-limiting examples of chelator(s) that can be included in any of the compositions provided herein include ethylenediaminetetraacetic acid (EDTA), 2,3-dimercapto-1-propanesulfonic acid sodium (DMPS), dimercaptosuccinic acid (DMSA), metallothionin, and desferroxamine.

The concentration of each of the chelator(s) and/or antioxidant(s) in any of the compositions provided herein can be between about 0.1 mM and about 150 mM (e.g., between about 0.1 mM and about 150 mM, between about 0.1 mM and about 125 mM, between about 0.1 mM and about 100 mM, between about 0.1 mM and about 80 mM, between about 0.1 mM and about 60 mM, between about 0.1 mM and about 50 mM, between about 0.1 mM and about 40 mM, between about 0.1 mM and about 30 mM, between about 0.1 mM and about 25 mM, between about 0.1 mM and about 20 mM, between about 0.1 mM and about 10 mM, between about 0.1 mM and about 5.0 mM, between about 0.5 mM and about 150 mM, between about 0.5 mM and about 100 mM, between about 0.5 mM and about 50 mM, between about 0.5 mM and about 25 mM, between about 0.5 mM and about 15 mM, between about 0.5 mM and about 10 mM, between about 0.5 mM and about 5 mM, between about 1 mM and about 125 mM, between about 1 mM and about 120 mM, between about 1 mM and about 100 mM, between about 1 mM and about 80 mM, between about 1 mM and about 60 mM, between about 1 mM and about 50 mM, between about 1 mM and about 40 mM, between about 1 mM and about 30 mM, between about 1 mM and about 25 mM, between about 5 mM and about 150 mM, between about 5 mM and about 125 mM, between about 5 mM and about 100 mM, between about 5 mM and about 80 mM, between about 5 mM and about 60 mM, between about 5 mM and about 50 mM, between about 5 mM and about 40 mM, between about 5 mM and about 30 mM, between about 5 mM and about 25 mM, between about 10 mM and about 150 mM, between about 10 mM and about 125 mM, between about 1 mM and about 100 mM, between about 10 mM and about 80 mM, between about 10 mM and about 60 mM, between about 10 mM and about 50 mM, between about 10 mM and about 40 mM, between about 10 mM and about 30 mM, between about 10 mM and about 25 mM, between about 20 mM and about 150 mM, between about 20 mM and about 125 mM, between about 20 mM and about 100 mM, between about 20 mM and about 80 mM, between about 20 mM and about 60 mM, between about 20 mM and about 50 mM, between about 20 mM and about 40 mM, between about 20 mM and about 30 mM, between about 30 mM and about 150 mM, between about 30 mM and about 125 mM, between about 30 mM and about 100 mM, between about 30 mM and about 80 mM, between about 30 mM and about 60 mM, between about 30 mM and about 50 mM, between about 30 mM and about 40 mM, between about 40 mM and about 150 mM, between about 40 mM and about 125 mM, between about 40 mM and about 100 mM, between about 40 mM and about 90 mM, between about 40 mM and about 80 mM, between about 40 mM and about 70 mM, between about 40 mM and about 60 mM, between about 50 mM and about 150 mM, between about 50 mM and about 125 mM, between about 50 mM and about 100 mM, between about 50 mM and about 80 mM, between about 50 mM and about 60 mM, between about 80 mM and about 150 mM, between about 80 mM and about 125 mM, between about 80 mM and about 100 mM, between about 100 mM and about 150 mM, or between about 100 mM and about 125 mM).

In some examples, the compositions provided herein contain one or more of 5 mM to about 150 mM mannitol (e.g., between about 10 mM and about 150 mM, between about 20 mM and about 150 mM, between about 30 mM and about 150 mM, between about 40 mM and about 150 mM, between about 50 mM and about 150 mM, between about 60 mM and about 140 mM, between about 70 mM and about 130 mM, between about 80 mM and about 120 mM, between about 90 mM and about 110 mM, between about 95 mM and about 105 mM, between about 5 mM and about 50 mM, between about 5 mM and about 45 mM, between about 5 mM and about 40 mM, between about 5 mM and about 35 mM, between about 10 mM and about 35 mM, between about 15 mM and about 35 mM, or between about 20 mM and about 30 mM mannitol); 5 mM to about 150 mM (e.g., between about 10 mM and about 150 mM, between about 20 mM and about 150 mM, between about 30 mM and about 150 mM, between about 40 mM and about 150 mM, between about 50 mM and about 150 mM, between about 60 mM and about 140 mM, between about 70 mM and about 130 mM, between about 80 mM and about 120 mM, between about 90 mM and about 110 mM, between about 95 mM and about 105 mM, between about 30 mM and about 70 mM, between about 35 mM and about 65 mM, between about 40 mM and about 60 mM, between about 45 mM and about 55 mM, between about 20 mM and about 50 mM, between about 25 mM and about 45 mM, between about 30 mM and about 40 mM, between about 30 mM and about 35 mM, between about 5 mM and about 45 mM, between about 10 mM and about 40 mM, between about 15 mM and about 35 mM, between about 20 mM and about 30 mM, or between about 20 mM and about 25 mM) methionine (or alternatively cysteine or glutathione); 5 mM to 150 mM sodium ascorbate (e.g., between about 10 mM and about 150 mM, between about 20 mM and about 150 mM, between about 30 mM and about 150 mM, between about 40 mM and about 150 mM, between about 50 mM and about 150 mM, between about 60 mM and about 140 mM, between about 70 mM and about 130 mM, between about 80 mM and about 120 mM, between about 90 mM and about 110 mM, between about 95 mM and about 105 mM, between about 10 mM and about 50 mM, between about 15 mM and about 45 mM, between about 20 mM and about 40 mM, between about 25 mM and about 35 mM, between about 30 mM and about 35 mM, between about 5 mM and about 45 mM, between about 10 mM and about 40 mM, between about 15 mM and about 35 mM, between about 20 mM and about 30 mM, between about 20 mM and about 25 mM sodium ascorbate); and 5 mM to about 150 mM (e.g., between about 10 mM and about 150 mM, between about 20 mM and about 150 mM, between about 30 mM and about 150 mM, between about 40 mM and about 150 mM, between about 50 mM and about 150 mM, between about 60 mM and about 140 mM, between about 70 mM and about 130 mM, between about 80 mM and about 120 mM, between about 90 mM and about 110 mM, between about 95 mM and about 105 mM, between about 30 mM and about 70 mM, between about 35 mM and about 65 mM, between about 40 mM and about 60 mM, between about 45 mM and about 55 mM, between about 20 mM and about 50 mM, between about 25 mM and about 45 mM, between about 30 mM and about 40 mM, between about 30 mM and about 35 mM, between about 5 mM and about 45 mM, between about 10 mM and about 40 mM, between about 15 mM and about 35 mM, between about 20 mM and about 30 mM, or between about 20 mM and about 25 mM) histidine.

Non-limiting examples of any of the compositions contain (i) between about 75 mM and about 125 mM (e.g., between about 80 mM and about 120 mM, between about 85 mM and about 115 mM, between about 90 mM and about 110 mM, or between about 95 mM and about 105 mM) mannitol (e.g., in a buffered solution, e.g., a phosphate buffer, such as 50 mM sodium phosphate, pH 6.0); (ii) between about 75 mM and about 125 mM (e.g., between about 80 mM and about 120 mM, between about 85 mM and about 115 mM, between about 90 mM and about 110 mM, or between about 95 mM and about 105 mM) methionine (or alternatively cysteine or glutathione) (e.g., in a buffered solution, e.g., a phosphate buffer, such as 50 mM sodium phosphate, pH 6.0); (iii) between about 75 mM and about 125 mM (e.g., between about 80 mM and about 120 mM, between about 85 mM and about 115 mM, between about 90 mM and about 110 mM, or between about 95 mM and about 105 mM) sodium ascorbate (e.g., in a buffered solution, e.g., a phosphate buffer, such as 50 mM sodium phosphate, pH 6.0); (iv) between about 75 mM and about 125 mM (e.g., between about 80 mM and about 120 mM, between about 85 mM and about 115 mM, between about 90 mM and about 110 mM, or between about 95 mM and about 105 mM) histidine (e.g., in a buffered solution, e.g., a phosphate buffer, such as 50 mM sodium phosphate, pH 6.0); (v) between about 30 mM and about 70 mM (e.g., between about 35 mM and about 65 mM, between about 40 mM and about 60 mM, or between about 45 mM and about 55 mM) methionine (or alternatively cysteine or glutathione) and between about 30 mM and about 70 mM (e.g., between about 35 mM and about 65 mM, between about 40 mM and about 60 mM, or between about 45 mM and about 55 mM) histidine (e.g., in a buffered solution, e.g., a phosphate buffer, such as 50 mM sodium phosphate, pH 6.0); (vi) between about 10 mM and about 50 mM (e.g., between about 15 mM and about 45 mM, between about 20 mM and about 40 mM, between about 25 mM to about 35 mM, or between about 30 mM and about 35 mM) methionine (or alternatively cysteine or glutathione), between about 10 mM and about 50 mM (e.g., between about 15 mM and about 45 mM, between about 20 mM and about 40 mM, between about 25 mM to about 35 mM, or between about 30 mM and about 35 mM) histidine, and between about 10 mM and about 50 mM (e.g., between about 15 mM and about 45 mM, between about 20 mM and about 40 mM, between about 25 mM to about 35 mM, or between about 30 mM to about 35 mM) sodium ascorbate (e.g., in a buffered solution, e.g., a phosphate buffer, such as 50 mM sodium phosphate, pH 6.0); or (vii) between about 5 mM and about 45 mM (e.g., between about 10 mM and about 40 mM, between about 15 mM and about 35 mM, between about 20 mM and about 30 mM, or between about 23 mM and about 27 mM) sodium ascorbate, between about 5 mM and about 45 mM (e.g., between about 10 mM and about 40 mM, between about 15 mM and about 35 mM, between about 20 mM and about 30 mM, or between about 23 mM and about 27 mM) methionine (or alternatively cysteine or glutathione), between about 5 mM and about 45 mM (e.g., between about 10 mM and about 40 mM, between about 15 mM and about 35 mM, between about 20 mM and about 30 mM, or between about 23 mM and about 27 mM) mannitol, and between about 5 mM and about 45 mM (e.g., between about 10 mM and about 40 mM, between about 15 mM and about 35 mM, between about 20 mM and about 30 mM, or between about 23 mM and about 27 mM) histidine (e.g., in a buffered solution, e.g., a phosphate buffer, such as 50 mM sodium phosphate, pH 6.0).

Non-limiting doses of gamma-irradiation sufficient to reduce bioburden of any of the compositions provided herein are described below. Additional doses of gamma-irradiation sufficient to reduce bioburden of any of the compositions provided herein are known in the art. For example, any of the compositions described herein can be gamma-irradiated at any of the doses, at any of the rates of gamma-irradiation, and/or at any of the temperatures for performing gamma-irradiation described herein (in any combination). The bioburden of a composition can be determined, e.g., by taking a sample from the composition that would contain self-replicating biological contaminant(s) present in the composition, e.g., by stomaching, ultrasonicating, shaking, vortex mixing, flushing, blending, or swabbing, and qualitating or quantifying the level of self-replicating biological contaminant(s) present in the sample (e.g., by placing the sample in a growth medium that would allow the biological contaminant to self-replicate, e.g., plating the sample on a petri dish, or running the sample through a membrane).

The amount of the at least one antioxidant agent and/or chelator sufficient to ameliorate the loss of binding capacity of the chromatography resin upon treatment with a dose of gamma-irradiation sufficient to reduce bioburden of the composition can be determined, e.g., using methods described in the Examples. For example, the level of reduction in the binding capacity of a chromatography resin treated with gamma-irradiation in the presence of an amount of the at least one antioxidant agent and/or chelator can be compared to the level of reduction in the binding capacity of the chromatography resin treated with the same dose of gamma-irradiation in the absence of the at least one antioxidant agent and/or chelator, where a decrease in the level of reduction in the binding capacity of the chromatography resin gamma-irradiated in the presence of the at least one antioxidant agent and/or chelator as compared to the chromatography resin gamma-irradiated in the absence of the at least one antioxidant agent and/or chelator, indicates that the at least one antioxidant agent and/or chelator was present in an amount sufficient to ameliorate the loss of binding capacity of the chromatography resin upon treatment with gamma-irradiation. Exemplary methods for determining the binding capacity of a chromatography resin are described in the Examples. Additional examples of methods for determining the binding capacity of a chromatography resin are known in the art.

Methods of Reducing Bioburden of a Chromatography Resin

Provided herein are methods of reducing bioburden of a chromatography resin. These methods include a step of exposing a container including a composition including a chromatography resin and at least one antioxidant agent and/or chelator to a dose of gamma-irradiation sufficient to reduce the bioburden of the container and the chromatography resin, where the at least one antioxidant agent and/or chelator are present in an amount sufficient to ameliorate the loss of binding capacity of the chromatography resin after (or upon) exposure to the dose of gamma-irradiation.

Also provided are methods of reducing bioburden of a chromatography resin that include exposing a container including a composition including a chromatography resin (and optionally at least one antioxidant agent and/or chelator in an amount sufficient to ameliorate loss of binding capacity of the chromatography resin after/upon exposure to gamma-irradiation) to gamma-irradiation at a rate of between about 0.1 kGy/hour to about 6 kGy/hour (e.g., between about 0.1 kGy/hour to about 5.5 kGy/hour, between about 0.1 kGy/hour to about 5.0 kGy/hour, between about 0.1 kGy/hour to about 4.5 kGy/hour, between about 0.1 kGy/hour to about 4.0 kGy/hour, between about 0.1 kGy/hour to about 3.5 kGy/hour, between about 0.1 kGy/hour to about 3.0 kGy/hour, between about 0.1 kGy/hour to about 2.5 kGy/hour, between about 0.1 kGy/hour to about 2.0 kGy/hour, between about 0.1 kGy/hour to about 1.5 kGy/hour, between about 0.1 kGy/hour to about 1.0 kGy/hour, between about 0.5 kGy/hour to about 6 kGy/hour, between about 0.5 kGy/hour to about 5.5 kGy/hour, between about 0.5 kGy/hour to about 5.0 kGy/hour, between about 0.5 kGy/hour to about 4.5 kGy/hour, between about 0.5 kGy/hour to about 4.0 kGy/hour, between about 0.5 kGy/hour to about 3.5 kGy/hour, between about 0.5 kGy/hour to about 3.0 kGy/hour, between about 0.5 kGy/hour to about 2.5 kGy/hour, between about 0.5 kGy/hour to about 2.0 kGy/hour) and/or at a temperature between about 4° C. to about 25° C. (e.g., between about 4° C. to about 20° C., between about 4° C. to about 15° C., between about 4° C. to about 10° C., between about 10° C. to about 25° C., between about 10° C. to about 20° C., between about 10° C. to about 15° C., or between about 15° C. to about 25° C.) for a dose of gamma-irradiation sufficient to reduce the bioburden of the container and the chromatography resin. In the methods described in this paragraph, the level of binding capacity of the gamma-irradiated chromagraphy resin produced by these methods is greater than the level of binding capacity of a gamma-irradiated chromagraphy resin gamma-irradiated at one or both of a rate of greater than 6.1 kGy/hour and/or at a temperature greater than 25° C.

A chromatography resin can be exposed to gamma-irradiation using methods known in the art. For example, an isotope such as Cobalt-60 or Caesium-137 can be used as the source of gamma-rays. The chromatography resin can be exposed to gamma-irradiation at a temperature of about between about −25° C. and about 0° C., inclusive, or between about 0° C. and about 25° C., inclusive. The chromagraphy resin can be exposed to a dose of gamma-irradiation of between about 0.1 kGy to about 100 kGy, between about 1 kGy to about 100 kGy, between about 1 kGy to about 90 kGy, between about 1 kGy to about 80 kGy, between about 1 kGy to about 70 kGy, between about 1 kGy to about 65 kGy, between about 5 kGy to about 65 kGy, between about 10 kGy to about 60 kGy, between about 10 kGy to about 55 kGy, between about 10 kGy to about 50 kGy, between about 10 kGy to about 45 kGy, between about 10 kGy to about 40 kGy, between about 10 kGy to about 35 kGy, between about 10 kGy to about 30 kGy, between about 15 kGy to about 50 kGy, between about 15 kGy to about 45 kGy, between about 15 kGy to about 40 kGy, between about 15 kGy to about 35 kGy, between about 20 kGy to about 30 kGy, or between about 23 kGy to about 27 kGy. The chromatography resin can be exposed to gamma-irradiation in a dose sufficient to result in a sterility assurance level of the chromatography resin of about or less than $1\times10^{-6}$, about or less than $1\times10^{-7}$, about or less than $10\times10^{-8}$, about or less than $1\times10^{-11}$, or about or less than $1\times10^{-12}$, or between about $1\times10^{-6}$ and about $1\times10^{-12}$, between about $1\times10^{-6}$ and about $1\times10^{-11}$, between about $1\times10^{-6}$ and about $1\times10^{-10}$, between about $1\times10^{-6}$ and about $1\times10^{-9}$, between about $1\times10^{-6}$ and about $1\times10^{-8}$, between $1\times10^{-6}$ and about $1\times10^{-7}$ between about $1\times10^{-7}$ and about $1\times10^{-12}$, between about $1\times10^{-7}$ and about $1\times10^{-11}$, between about $1\times10^{-7}$ and about $1\times10^{-10}$, between about $1\times10^{-7}$ and about $1\times10^{-9}$, between about $1\times10^{-7}$ and about $1\times10^{-8}$, between about $1\times10^{-8}$ and about $1\times10^{-12}$, between about $1\times10^{-8}$ and about $1\times10^{-11}$, between about $1\times10^{-8}$ and about $1\times10^{-10}$, or between about $1\times10^{-8}$ and about $1\times10^{-9}$.

A dose of gamma-irradiation sufficient to reduce the bioburden of a chromatography resin can be determined using methods known in the art. For example, the bioburden level of a chromatography resin treated with a dose of gamma-irradiation can be compared to the bioburden level of an untreated (e.g., a control, non-gamma-irradiated) chromatography resin, and a decrease in the level of bioburden in the gamma-irradiated chromatography resin as compared to the untreated chromatography resin indicates that the dose of gamma-irradiation is sufficient to reduce the bioburden of a chromatography resin. Exemplary methods for determining the level of bioburden in a composition (e.g., a chromatography resin) are described herein. Additional methods for determining the level of bioburden in a composition (e.g., a chromatography resin) are known in the art.

The chromatography resin in any of these methods can be an anionic exchange chromatography resin, cationic exchange chromatography resin, size exclusion chromatography resin, hydrophobic interaction chromatography resin, or an affinity chromatography resin, or any combination thereof. Non-limiting examples of an affinity chromatography resin can include a protein or peptide ligand (e.g., between about 5 amino acids to about 100 amino acids, between about 5 amino acids to about 90 amino acids, between about 5 amino acids and about 80 amino acids, between about 5 amino acids and about 70 amino acids, between about 5 amino acids and about 60 amino acids, between about 5 amino acids and about 50 amino acids, between about 5 amino acids and about 40 amino acids, between about 5 amino acids and about 30 amino acids, between about 5 amino acids and about 25 amino acids, or between about 5 amino acids and about 20 amino acids), a small molecule substrate or cofactor of an enzyme, an aptamer, an inhibitor (e.g., competitive protein inhibitor) or a metal. In some embodiments, the affinity chromatography resin includes a protein ligand (e.g., protein A). Additional examples of affinity chromatography resin include a cofactor ligand, a substrate ligand, a metal ligand, a product ligand, or an aptamer ligand. In some examples, the chromatography resin is a biomodal chromatography resin (e.g., anionic exchange chromatography resin and hydrophobic interaction chromatography resin). The chromatography resin can be an anionic exchange chromatography resin (e.g., an anionic exchange chromatography resin including N-benzyl-N-methyl-ethanolamine groups).

The container that includes a chromatography resin can be a plastic container (e.g., a cylindrical tube, a sealed or clamped box, or a sealed bag). Non-limiting examples of containers used in these methods include a storage vessel or a chromatography column. For example, the composition including the chromatography resin and the at least one antioxidant agent and/or chelator can be present in a sealed container (e.g., a slurry in a sealed container or a packed chromatography resin in a sealed container (e.g., chromatography column)) A container used in the methods described herein can be a disposable chromatography column. In some embodiments, the container used in the methods described herein is a disposable chromatography column placed in a blister pack. The container (e.g., storage vessel or chromatography column) can have an internal total volume of between about 1 mL to about 1 L (e.g., between about 1 mL and about 900 mL, between about 1 mL and about 800 mL, between about 1 mL and about 700 mL, between about 1 mL and about 600 mL, between about 1 mL and about 500 mL, between about 1 mL and about 450 mL, between about 1 mL and about 400 mL, between about 1 mL and about 350 mL, between about 1 mL and about 300 mL, between about 1 mL and about 250 mL, between about 1 mL and about 200 mL, between about 1 mL and about 150 mL, between about 1 mL and about 100 mL, between about 1 mL and about 75 mL, between about 1 mL and about 50 mL, between about 1 mL and about 40 mL, between about 1 mL and about 30 mL, or between about 1 mL and about 20 mL).

The composition containing a chromatography resin and the at least one antioxidant agent and/or chelator included in the container can be present in a solid mixture (e.g., a dry or wetted solid mixture). For example, the container can include a slurry of a sedimented chromatography resin in a liquid (e.g., buffered solution) containing the at least one antioxidant agent and/or chelator. In some embodiments, the container can include a packed chromatography resin. For example, the container including the composition including the chromatography resin and at least one antioxidant agent and/or chromatography resin is a packed chromatography column (e.g., where the resin is packed in a liquid (e.g., a buffered solution) containing the at least one antioxidant agent and/or chromatography resin). Some embodiments include, prior to exposing, disposing the composition containing the chromatography resin and the at least one antioxidant agent and/or chelator into the container.

Any of the antioxidant agents and/or chelators described herein can be used in any combination, using any combination of the exemplary concentrations described herein. For example, the composition can include at least one antioxidant agent selected from: reduced glutathione, reduced thioredoxin, reduced cysteine, a carotenoid, melatonin, lycopene, tocopherol, reduced ubiquinone, ascorbate, bilirubin, uric acid, lipoic acid, a flavonoid, a phenolpropanoid acid, lidocaine, naringenin, fullerene, glucose, mannitol, 4-hydroxy-2,2,6,6-tetramethylpiperidin-1-oxyl, and dimethylmethoxy chromanol, and/or at least one chelator selected from: EDTA, DMPS, DMSA, metallothionin, and desferroxamine.

Exemplary methods for determining/identifying amount(s) of the at least one antioxidant agent and/or chelator sufficient to ameliorate the loss of binding capacity of the chromatography resin upon treatment with a dose of gamma-irradiation sufficient to reduce bioburden of the composition are described herein. Additional methods for determining/identifying amount(s) of the at least one antioxidant agent and/or chelator sufficient to ameliorate the loss of binding capacity of the chromatography resin upon treatment with a dose of gamma-irradiation sufficient to reduce bioburden of the composition are known in the art.

Also provided herein are a reduced bioburden chromatography resin produced by any of the methods described herein (e.g., a reduced bioburden chromatography resin provided in a storage container, e.g., a sealed storage container). The reduced bioburden chromatography resin generated using any of the methods described herein can have a sterility assurance level of about or less than $1\times10^{-6}$, about or less than $1\times10^{-7}$, about or less than $10\times10^{-8}$, about or less than $1\times10^{-11}$, or about or less than $1\times10^{-12}$, or between about $1\times10^{-6}$ and about $1\times10^{-12}$, between about $1\times10^{-6}$ and about $1\times10^{-11}$, between about $1\times10^{-6}$ and about $1\times10^{-10}$, between about $1\times10^{-6}$ and about $1\times10^{-9}$, between about $1\times10^{-6}$ and about $1\times10^{-8}$, between $1\times10^{-6}$ and about $1\times10^{-7}$, between about $1\times10^{-7}$ and about $1\times10^{-12}$, between about $1\times10^{-7}$ and about $1\times10^{-11}$, between about $1\times10^{-7}$ and about $1\times10^{-10}$, between about $1\times10^{-7}$ and about $1\times10^{-9}$, between about $1\times10^{-7}$ and about $1\times10^{-8}$, between about $1\times10^{-8}$ and about $1\times10^{-12}$, between about $1\times10^{-8}$ and about $1\times10^{-11}$, between about $1\times10^{-8}$ and about $1\times10^{-10}$, or between about $1\times10^{-8}$ and about $1\times10^{-9}$. A reduced bioburden chromatography resin produced by any of the methods described herein can have a binding capacity that is at least 74% (e.g., at least 76%, at least 78%, at least 80%, at least 82%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%) or between about 74% and 95%, between about 74% and about 95%, between about 76% and about 95%, at least about 78% and about 95%, between about 80% and about 95%, or between about 74% and about 90%, between about 76% and about 90%, between about 78% and about 90%, or between about 80% and about 90% of the binding capacity of the same chromatography resin that has not been treated to reduce its bioburden (e.g., has not been gamma-irradiated), when the same protein is used to test the binding capacity of both the chromatography resin produced by the methods described herein and the control, untreated chromatography resin.

Methods of Making a Reduced Bioburden Packed Chromatography Column

Also provided herein are methods of making a reduced packed chromatography column that includes providing a reduced bioburden chromatography resin produced by any of the methods described herein and packing the chromatography resin into a reduced bioburden column in an aseptic or reduced bioburden environment. In some embodiments, a reduced bioburden packed chromatography column can be produced by exposing a column including a packed chromatography resin and at least one antioxidant agent and/or chelator to a dose of gamma-irradiation sufficient to reduce the bioburden of the column and the packed chromatography resin, where the at least one antioxidant agent and/or chelator is present in an amount sufficient to ameliorate the loss of binding capacity of the packed chromatography resin after exposure to the dose of gamma-irradiation.

Also provided are reduced bioburden packed chromatography column(s) produced by the methods described herein. Any of the reduced bioburden packed chromatography column(s) produced by the methods described herein can have a sterility assurance level of about or less than $1\times10^{-6}$, about or less than $1\times10^{-7}$, about or less than $10\times10^{-8}$, about or less than $1\times10^{-11}$, or about or less than $1\times10^{-12}$, or between about $1\times10^{-6}$ and about $1\times10^{-12}$, between about $1\times10^{-6}$ and about $1\times10^{-11}$, between about $1\times10^{-6}$ and about $1\times10^{-10}$, between about $1\times10^{-6}$ and about $1\times10^{-9}$, between about $1\times10^{-6}$ and about $1\times10^{-8}$, between $1\times10^{-6}$ and about $1\times10^{-7}$, between about $1\times10^{-7}$ and about $1\times10^{-12}$, between about $1\times10^{-7}$ and about $1\times10^{-11}$, between about $1\times10^{-7}$ and about $1\times10^{-10}$, between about $1\times10^{-7}$ and about $1\times10^{-9}$, between about $1\times10^{-7}$ and about $1\times10^{-8}$, between about $1\times10^{-8}$ and about $1\times10^{-12}$, between about $1\times10^{-8}$ and about $1\times10^{-11}$, between about $1\times10^{-8}$ and about $1\times10^{-10}$, or between about $1\times10^{-8}$ and about $1\times10^{-9}$. Any of the reduced bioburden packed chromatography column(s) produced by the methods described herein can contain at least one chromatography resin selected from the group of: anionic exchange chromatography resin, cationic exchange chromatography resin, affinity chromatography resin (e.g., any of the affinity chromatography resins described herein or known in the art), hydrophilic interaction chromatography resin, and size exclusion chromatography resin. For example, any of the reduced bioburden packed chromatography columns described herein can include an affinity chromatography resin including a protein ligand (e.g., protein A). A reduced bioburden packed chromatography column described herein can include an anionic exchange chromatography resin (e.g., an anionic exchange chromatography resin including N-benzyl-N-methyl-ethanolamine groups).

Methods of Performing Reduced Bioburden Chromatography

The methods described herein include the use of a reduced bioburden packed chromatography column provided herein and the processes described herein include the use of one or two MCCSs that include at least one reduced bioburden packed chromatography column provided herein. The gamma-irradiated chromatography resin can be any type of resin described herein (or any type of chromatography resin known in the art).

The reduced bioburden packed chromatography column can be prepared using any of the methods described herein. For example, the reduced bioburden packed chromatography column can be produced by packing a chromatography column with a composition including a chromatography resin(s) and at least one antioxidant and/or chelator (e.g., any of such compositions described herein), and exposing the packed column to gamma-irradiation (e.g., using any of the exposures and conditions described herein). In other examples, the reduced bioburden packed chromatography column can be produced by exposing a container including a chromatography resin and at least one antioxidant agent and/or chelator to a dose of gamma-irradiation and packing a chromatography column with resulting reduced bioburden chromatography resin. In such methods, the chromatography resin (present in the container during exposure to gamma-irradiation) can be present as a slurry in the container, and the chromatography column is packed in a reduced bioburden hood. In other methods, the chromatography resin present in the container with the at least one antioxidant agent and/or chelator can be exposed to gamma-irradiation as a solid mixture in the container, and a slurry of the resulting reduced bioburden chromatography resin can be prepared using a reduced bioburden buffer (e.g., prepared in a reduced bioburden hood), and the resulting slurry used to pack a chromatography column in a reduced bioburden hood. In some of these examples, the chromatography column, prior to packing, can be treated to reduce the bioburden (e.g., autoclaved, gamma-irradiated, or exposure to ethylene oxide).

The reduced bioburden packed chromatography column used in any of the methods described herein can have a sterility assurance level (SAL) of between about $1 \times 10^{-3}$ and about $1 \times 10^{-12}$, between about $1 \times 10^{-4}$ and about $1 \times 10^{-12}$, between $1 \times 10^{-5}$ and about $1 \times 10^{-11}$, between about $1 \times 10^{-5}$ and about $1 \times 10^{-10}$, between about $1 \times 10^{-5}$ and about $1 \times 10^{-9}$, between about $1 \times 10^{-6}$ and about $1 \times 10^{-9}$, or between about $1 \times 10^{-6}$ and about $1 \times 10^{-8}$, inclusive.

Reduced Bioburden Buffers

The methods and processes described herein can be performed using one or more reduced bioburden buffers. As can be appreciated in the art, a reduced bioburden buffer can be any type of buffer used in a cycle of chromatography (e.g., a buffer used in any of the steps in a cycle of chromatography or in any of the unit operations described herein). Exemplary methods for reducing the bioburden of a buffer include filtration (0.2 μm-pore size filtration), autoclaving, and gamma-irradiation. Additional methods for reducing the bioburden of a buffer are known in the art. A reduced bioburden buffer can have a sterility assurance level of between about $1 \times 10^{-3}$ and about $1 \times 10^{-12}$, between about $1 \times 10^{-4}$ and about $1 \times 10^{-12}$, between $1 \times 10^{-5}$ and about $1 \times 10^{-11}$, between about $1 \times 10^{-5}$ and about $1 \times 10^{-10}$, between about $1 \times 10^{-5}$ and about $1 \times 10^{-9}$, between about $1 \times 10^{-6}$ and about $1 \times 10^{-9}$, or between about $1 \times 10^{-6}$ and about $1 \times 10^{-8}$, inclusive.

Recombinant Therapeutic Proteins

A recombinant protein as described herein can be a recombinant therapeutic protein. Non-limiting examples of recombinant therapeutic proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme®, or Cerezyme®), proteins (e.g., human erythropoietin, tumor necrosis factor (TNF), or an interferon alpha or beta), or immunogenic or antigenic proteins or protein fragments (e.g., proteins for use in a vaccine). Non-limiting examples of recombinant therapeutic enzymes that can be used to treat a variety of lysosomal storage diseases are shown in FIG. 10. The recombinant therapeutic protein can be an engineered antigen-binding polypeptide that includes at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant therapeutic proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, golimumab, infliximab, natalizumab, palivizumab, panitumumab, pertuzumab, ranibizumab, rituximab, tocilizumab, and trastuzumab. Additional examples of recombinant therapeutic antibodies that can be produced by the methods described herein are known in the art. Additional non-limiting examples of recombinant therapeutic proteins that can be produced/purified by the present methods include: alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, and alteplase.

A secreted, soluble recombinant therapeutic protein can be recovered from the liquid culture medium (e.g., a first and/or second liquid culture medium) by removing or otherwise physically separating the liquid culture medium from the cells (e.g., mammalian cells). A variety of different methods for removing liquid culture medium from cells (e.g., mammalian cells) are known in the art, including, for example, centrifugation, filtration, pipetting, and/or aspiration. The secreted recombinant therapeutic protein can then be recovered and further purified from the liquid culture medium using a variety of biochemical techniques including various types of chromatography (e.g., affinity chromatography, molecular sieve chromatography, cation exchange chromatography, anion exchange chromatography, or hydrophobic interaction chromatography, or any combination thereof) and/or filtration (e.g., molecular weight cut-off filtration).

Cycle of Chromatography

As is well-known in the art, the steps in a cycle of chromatography can differ depending on the chromatography resin, the buffers used to perform each step in the cycle, and the biophysical characteristics of the target recombinant protein (e.g., recombinant therapeutic protein). For example, an affinity chromatography column can include the steps of loading an affinity chromatography column with a fluid including the target recombinant protein, washing the column to remove unwanted biological material (e.g., contaminating proteins and/or small molecules), eluting the target recombinant protein bound to the column, and re-equilibrating the column. A cycle of chromatography using a cationic and/or anionic exchange chromatography column, where the target recombinant protein binds to the chromatography resin in the loading step, can include the steps of loading the column with a fluid including the target protein, washing the column to remove unwanted biological material, eluting the target recombinant protein bound to the column, and re-equilibrating the column. In other examples, a cycle of chromatography using a cationic and/or anionic exchange chromatography column, where unwanted biological material binds to the chromatography resin during the loading step, while the target recombinant protein does not, can include the steps of loading the column with a fluid including the target protein, collecting the target recombinant protein in the flow-through, and reequilibrating the column. As is well-known in the art, any of the single steps in a chromatography cycle can include a single buffer or multiple buffers (e.g., two or more buffers), and one or more of any of the single steps in a chromatography cycle can include a buffer gradient. Any of the combination of various well-known aspects of a single cycle of chromatography can be used in these methods in any combination, e.g., different chromatography resin(s), flow-rate(s), buffer(s), void volume(s) of the column, bed volume(s) of the column, volume(s) of buffer used in each step, volume(s) of the fluid including the target protein, and the number and types of buffer(s) used in each step.

Methods of Performing Reduced Bioburden Column Chromatography

Provided herein are methods of performing reduced bioburden chromatography. These methods include providing a reduced bioburden packed chromatography column produced using any of the methods described herein, and performing a column chromatography using the reduced bioburden packed chromatography column. The reduced bioburden packed chromatography column can include at least one of any of the chromatography resins described herein, in any combination. For example, the chromatography resin present in the reduced bioburden packed chromatography column can be an affinity resin including a protein ligand (e.g., protein A) or can include an anionic exchange chromatography resin. The reduced bioburden packed chromatography column can have any of the exemplary internal volumes described herein. The reduced bioburden packed chromatography column can have any shape (e.g., a cylinder, near cylindrical shape, or ellipsoidal shape) described herein or known in the art. The column chromatography performed in these methods can be used to purify or isolate a recombinant protein (e.g., any of the recombinant therapeutic proteins described herein or known in the art). In some examples, the reduced bioburden packed chromatography column is part of a multi-column chromatography system (MCCS), e.g., can be part of a periodic counter current chromatography system (PCCS).

The column chromatography performed can include at least one cycle of chromatography described herein or known in the art. For example, the at least one cycle of chromatography can include the steps of: capturing the recombinant protein by exposing the chromatography resin with a liquid including a recombinant protein; washing the chromatography resin by exposing the chromatography resin with a wash buffer, eluting the recombinant protein by exposing the chromatography resin with an elution buffer; and regenerating the chromatography resin by exposing the chromatography resin to a regeneration buffer. In some examples, the liquid including the recombinant protein is a liquid culture medium (e.g., a liquid culture medium collected from a perfusion or batch culture) or a diluted liquid culture medium (e.g., a culture medium diluted in buffer).

The column chromatography can be performed using a closed and integrated system (e.g., any of the exemplary closed and integrated systems described herein or known in the art). For example, the column chromatography can be performed using a closed and integrated system, where the buffer is reduced bioburden buffer. As is well-known in the art, reduced bioburden buffer can be produced using a variety of different methods (e.g., prepared by filtration, by autoclaving, or heat treatment).

The column chromatography can include two or more (e.g., 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, or 100 or more) cycles of chromatography. In some examples, the column chromatography is performed continuously over a period of at least 3 days (e.g., at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days, at least 50 days, at least 55 days, at least 60 days, at least 65 days, at least 70 days, at least 75 days, at least 80 days, at least 85 days, at least 90 days, at least 95 days, or at least 100 days).

In some embodiments, the chromatography resin in the reduced bioburden packed chromatography column has a percentage binding capacity of between about 75% to about 100% (e.g., between about 76% and about 98%, between about 76% and about 96%, between about 76% and about 94%, between about 76% and about 92%, between about 76% and about 90%, between about 78% and about 100%, between about 78% and about 98%, between about 78% and about 96%, between about 78% and about 94%, between about 78% and about 92%, between about 78% and about 90%, between about 80% and about 100%, between about 80% and about 98%, between about 80% and about 96%, between about 80% and about 94%, between about 80% and about 92%, between about 80% and about 90%, between about 82% and about 100%, between about 82% and about 98%, between about 82% and about 96%, between about 82% and about 94%, between about 82% and about 92%, between about 82% and about 90%, between about 84% and about 100%, between about 84% and about 98%, between about 84% and about 96%, between about 84% and about 94%, between about 84% and about 92%, between about 84% and about 90%, between about 86% and about 100%, between about 86% and about 98%, between about 86% and about 96%, between about 86% and about 94%, between about 86% and about 92%, between about 88% and about 100%, between about 88% and about 98%, between about 88% and about 96%, between about 88% and about 94%, between about 90% and about 100%, between about 90% and about 98%, between about 90% and about 96%, between about 92% and about 100%, or between about 92% and about 98%) as compared to the same resin not treated with gamma-irradiation (when the same protein is used to test the binding capacity of both resins) (e.g., assessed immediately after exposure to gamma-irradiation).

Integrated, Closed or Substantially Closed, and Continuous Processes for Manufacturing of a Recombinant Protein Provided herein are integrated, closed or substantially closed, and continuous processes for manufacturing a purified recombinant protein (e.g., a recombinant therapeutic protein). These processes include providing a liquid culture medium including a recombinant protein (e.g., a recombinant therapeutic protein) that is substantially free of cells.

Some processes include continuously feeding the liquid culture medium into a multi-column chromatography system (MCCS) that includes at least one reduced bioburden packed chromatography column provided herein, where these processes utilize reduced bioburden buffer, are integrated, and run continuously from the liquid culture medium to an eluate from the MCCS that is the purified recombinant protein (e.g., a therapeutic protein drug substance).

Some processes include continuously feeding the liquid culture medium into a first MCCS (MCCS1), capturing the recombinant protein from the liquid culture medium using the MCCS1, producing an eluate from the MCCS1 that includes the recombinant protein and continuously feeding the eluate into a second MCCS (MCCS2), and continuously feeding the recombinant protein from the eluate into the MCCS2 and subsequently eluting the recombinant protein to thereby produce the purified recombinant protein, where at least one column in the MCCS1 and/or the MCCS2 is a reduced bioburden packed chromatography column provided herein, the processes utilize reduced bioburden buffer, are integrated, and run continuously from the liquid culture medium to the purified recombinant protein.

In some examples, each of the chromatography columns used in the MCCS, MCCS1, and/or MCCS2 is a reduced bioburden packed chromatography column provided herein. Some embodiments further include a step of formulating the purified recombinant protein into a pharmaceutical composition.

The processes described herein provide continuous and time-efficient production of a purified recombinant protein from a liquid culture medium including the recombinant protein. For example, the elapsed time between feeding a liquid culture medium including a therapeutic protein into the MCCS or MCCS1 and eluting the recombinant protein from the MCCS or MCCS2, respectively, can be, e.g., between about 4 hours and about 48 hours, inclusive, e.g., between about 4 hours and about 40 hours, between about 4 hours and about 35 hours, between about 4 hours and about 30 hours, between about 4 hours and about 28 hours, between about 4 hours and about 26 hours, between about 4 hours and about 24 hours, between about 4 hours and about 22 hours, between about 4 hours and about 20 hours, between about 4 hours and about 18 hours, between about 4 hours and about 16 hours, between about 4 hours and about 14 hours, between about 4 hours and about 12 hours, between about 6 hours and about 12 hours, between about 8 hours and about 12 hours, between about 6 hours and about 20 hours, between about 6 hours and about 18 hours, between about 6 hours and about 14 hours, between about 8 hours and about 16 hours, between about 8 hours and about 14 hours, between about 8 hours and about 12 hours, between about 10 hours and 20 hours, between about 10 hours and 18 hours, between about 10 hours and 16 hours, between about 10 hours and 14 hours, between about 12 hours and about 14 hours, between about 10 hours and about 40 hours, between about 10 hours and about 35 hours, between about 10 hours and about 30 hours, between about 10 hours and about 25 hours, between about 15 hours and about 40 hours, between about 15 hours and about 35 hours, between about 15 hours and about 30 hours, between about 20 hours and about 40 hours, between about 20 hours and about 35 hours, or between about 20 hours and about 30 hours, inclusive. In other examples, the elapsed time between feeding the liquid culture medium including the recombinant protein into the MCCS or MCCS1 and eluting the recombinant protein from the MCCS or MCCS2, respectively, is, e.g., greater than about 4 hours and less than about 40 hours, inclusive, e.g., greater than about 4 hours and less than about 39 hours, about 38 hours, about 37 hours, about 36 hours, about 35 hours, about 34 hours, about 33 hours, about 32 hours, about 31 hours, about 30 hours, about 29 hours, about 28 hours, about 27 hours, about 26 hours, about 25 hours, about 24 hours, about 23 hours, about 22 hours, about 21 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, or about 4.5 hours, inclusive.

Non-limiting aspects of the MCCSs that can be used in any of these processes (MCCS, MCCS1, and/or MCCS2) are described in U.S. Provisional Patent Application Ser. Nos. 61/775,060 and 61/856,390 (each incorporated herein by reference).

Some exemplary processes do not utilize a holding step (e.g., do not use a reservoir (e.g., break tank) in the entire process). Others may use a maximum of 1, 2, 3, 4, or 5 reservoir(s) (e.g., break tank(s)) in the entire process. Any of the processes described herein can utilize a maximum of 1, 2, 3, 4, or 5 reservoir(s) (e.g., break tank(s)) in the entire process, where each break tank only holds a recombinant protein for a total time period of, e.g., between about 5 minutes and less than about 6 hours, inclusive, e.g., between about 5 minutes and about 5 hours, about 4 hours, about 3 hours, about 2 hours, about 1 hour, or about 30 minutes, inclusive.

Some processes utilize one, two, three, four, five, or six reservoir(s) (e.g., break tank(s)) and can have a capacity that is, e.g., between 1 mL and about 300 mL, inclusive, e.g., between 1 mL and about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL (inclusive). Any reservoir(s) (e.g., break tank(s)) used (in any of the processes described herein) to hold fluid before it is fed into the MCCS or MCCS1 can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the MCCS or MCCS1. A reservoir(s) (e.g., break tanks(s)) can be used to hold eluate from MCCS1 before it enters into the MCCS2 and can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the MCCS2.

Various additional aspects of these processes are described in detail below and can be used in any combination in the processes provided herein without limitation. Exemplary aspects of the provided processes are described below; however, one skilled in the art will appreciate that additional steps can be added to the processes described herein and other materials can be used to perform any of the steps of the processes described herein.

Liquid Culture Medium

Liquid culture medium that includes a recombinant protein (e.g., recombinant therapeutic protein) that is substantially free of cells can be derived from any source. For example, the liquid culture medium can be obtained from a recombinant cell culture (e.g., a recombinant bacterial, yeast, or mammalian cell culture). The liquid culture medium can be obtained from a fed-batch cell (e.g., mammalian cell) culture (e.g., a fed-batch bioreactor including a culture of mammalian cells that secrete the recombinant protein) or a perfusion cell (e.g., mammalian cell) culture (e.g., a perfusion bioreactor including a culture of mammalian cells that secrete the recombinant protein). The liquid culture medium can also be a clarified liquid culture medium from a culture of bacterial or yeast cells that secrete the recombinant protein.

Liquid culture medium obtained from a recombinant cell culture can be filtered or clarified to obtain a liquid culture medium that is substantially free of cells and/or viruses. Methods for filtering or clarifying a liquid culture medium in order to remove cells are known in the art (e.g., 0.2-μm filtration and filtration using an Alternating Tangential Flow (ATF™) system). Recombinant cells can also be removed from liquid culture medium using centrifugation and removing the supernatant that is liquid culture medium that is substantially free of cells, or by allowing the cells to settle to the gravitational bottom of a container (e.g., bioreactor) including the liquid culture medium, and removing the liquid culture medium (the liquid culture medium that is substantially free of cells) that is distant from the settled recombinant cells.

The liquid culture medium can be obtained from a culture of recombinant cells (e.g., recombinant bacteria, yeast, or mammalian cells) producing any of the recombinant proteins (e.g., recombinant therapeutic proteins) described herein or known in the art. Some examples of any of the processes described herein can further include a step of culturing recombinant cells (e.g., recombinant bacteria, yeast, or mammalian cells) that produce the recombinant protein (e.g., recombinant therapeutic protein).

The liquid culture medium can be any of the types of liquid culture medium described herein or known in the art. For example, the liquid culture medium can be selected from the group of: animal-derived component-free liquid culture medium, serum-free liquid culture medium, serum-containing liquid culture medium, chemically-defined liquid culture medium, and protein-free liquid culture medium. In any of the processes described herein, a liquid culture medium obtained from a culture can be diluted by addition of a second fluid (e.g., a buffer) before it is fed into the MCCS or MCCS1.

The liquid culture medium including a recombinant protein that is substantially free of cells can be stored (e.g., at a temperature below about 15° C. (e.g., below about 10° C., below about 4° C., below about 0° C., below about −20° C., below about −50° C., below about −70 C.°, or below about −80° C.) for at least 1 day (e.g., at least about 2 days, at least about 5 days, at least about 10 days, at least about 15 days, at least about 20 days, or at least about 30 days) prior to feeding the liquid culture medium into the MCCS or MCCS1. Alternatively, in some examples the liquid culture medium is fed into the MCCS or MCCS1 directly from a bioreactor (e.g., fed into the MCCS or MCCS1 directly from the bioreactor after a filtering or clarification step).

Multi-Column Chromatography Systems

The processes described herein include the use of a MCCS or two or more (e.g., two, three, four, five, or six) multi-column chromatography systems (MCCSs) (e.g., an MCCS1 and MCCS2). A MCCS can include two or more chromatography columns, two or more chromatographic membranes, or a combination of at least one chromatography column and at least one chromatographic membrane. In non-limiting examples, a MCCS (e.g., MCCS, MCCS1, and/or MCCS2 in any of the processes herein) can include four chromatographic columns, three chromatographic columns and a chromatographic membrane, three chromatographic columns, two chromatographic columns, two chromatographic membranes, and two chromatographic columns and one chromatographic membrane. Additional examples of combinations of chromatography columns and/or chromatographic membranes can be envisioned for use in an MCCS (e.g., MCCS, MCCS1, and/or MCCS2 in any of the processes described herein) by one skilled in the art without limitation. The individual chromatography columns and/or chromatographic membranes present in a MCCS can be identical (e.g., have the same shape, volume, resin, capture mechanism, and unit operation), or can be different (e.g., have one or more of a different shape, volume, resin, capture mechanism, and/or unit operation). The individual chromatography column(s) and/or chromatographic membrane(s) present in a MCCS (e.g., MCCS, MCCS1, and/or MCCS2 in any of the processes described herein) can perform the same unit operation (e.g., the unit operation of capturing, purifying, or polishing) or different unit operations (e.g., different unit operations selected from, e.g., the group of capturing, purifying, polishing, inactivating viruses, adjusting the ionic concentration and/or pH of a fluid including the recombinant protein, and filtering). For example, in examples of the processes described herein, at least one chromatography column and/or chromatographic membrane in the MCCS or MCCS1 performs the unit operation of capturing the recombinant protein.

The one or more chromatography column(s) that can be present in an MCCS (e.g., present in the MCCS, MCCS1, and/or MCCS2) can have a resin volume of, e.g., between about 1 mL and about 2 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, or about 100 mL, inclusive. The one or more chromatography column(s) that can be present in an MCCS (e.g., present in the MCCS, MCCS1, and/or MCCS2) can have a resin volume of between about 2 mL to about 100 mL, between about 2 mL and about 90 mL, between about 2 mL and about 80 mL, between about 2 mL and about 70 mL, between about 2 mL and about 60 mL, between about 2 mL and about 50 mL, between about 5 mL and about 50 mL, between about 2 mL and about 45 mL, between about 5 mL and about 45 mL, between about 2 mL and about 40 mL, between about 5 mL and about 40 mL, between about 2 mL and about 35 mL, between about 5 mL and about 35 mL, between about 2 mL and about 30 mL, between about 5 mL and about 30 mL, between about 2 mL and about 25 mL, between about 5 mL and about 25 mL, between about 15 mL and about 60 mL, between about 10 mL and about 60 mL, between about 10 mL and about 50 mL, and between about 15 mL and about 50 mL. The one or more chromatography column(s) in an MCCS (e.g., the MCCS, MCCS1, and/or MCCS2) used in any of the processes described herein can have the substantially the same resin volume or can have different resin volumes. The flow rate used for the one or more chromatography column(s) in an MCCS (e.g., the MCCS, MCCS1, and/or MCCS2) can be, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, or between about 1.0 mL/minute and about 15.0 mL/minute).

The one or more chromatography column (s) in an MCCS (e.g., MCCS, MCCS1, and/or MCCS2) can have substantially the same shape or can have substantially different shapes. For example, the one or more chromatography column(s) in an MCCS (e.g., in the MCCS, MCCS1, and/or MCCS2) can have substantially the shape of a circular cylinder or can have substantially the same shape of an oval cylinder.

The one or more chromatographic membrane(s) that can be present in an MCCS (e.g., present in the MCCS, MCCS1, and/or MCCS2) can have a bed volume of, e.g., between about 1 mL to about 500 mL (e.g., between about 1 mL to about 475 mL, between about 1 mL to about 450 mL, between about 1 mL to about 425 mL, between about 1 mL to about 400 mL, between about 1 mL to about 375 mL, between about 1 mL to about 350 mL, between about 1 mL to about 325 mL, between about 1 mL to about 300 mL, between about 1 mL to about 275 mL, between about 1 mL to about 250 mL, between about 1 mL to about 225 mL, between about 1 mL to about 200 mL, between about 1 mL to about 175 mL, between about 1 mL to about 150 mL, between about 1 mL to about 125 mL, between about 1 mL to about 100 mL, between about 2 mL to about 100 mL, between about 5 mL to about 100 mL, between about 1 mL to about 80 mL, between about 2 mL to about 80 mL, between about 5 mL to about 80 mL, between about 1 mL to about 60 mL, between about 2 mL to about 60 mL, between about 5 mL to about 60 mL, between about 1 mL to about 40 mL, between about 2 mL to about 40 mL, between about 5 mL to about 40 mL, between about 1 mL to about 30 mL, between about 2 mL to about 30 mL, between about 5 mL to about 30 mL, between about 1 mL and about 25 mL, between about 2 mL and about 25 mL, between about 1 mL and about 20 mL, between about 2 mL and about 20 mL, between about 1 mL and about 15 mL, between about 2 mL and about 15 mL, between about 1 mL and about 10 mL, or between about 2 mL and about 10 mL).

One or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of reduced bioburden buffer can be employed during the use of the MCCS, MCCS1, and/or MCCS2 in any of the processes described herein. As is known in the art, the one or more types of reduced bioburden buffer used in the MCCS, MCCS1, and/or MCCS2 in the processes described herein will depend on the resin present in the chromatography column(s) and/or the chromatographic membrane(s) of the MCCS, MCCS1, and/or MCCS2, the biophysical properties of the recombinant protein, and unit operation (e.g., any of the exemplary unit operations described herein) performed by the specific chromatography column(s) and/or chromatography membranes of the MCCS, MCCS1, and/or MCCS2. The volume and type of buffer employed during the use of the MCCS, MCCS1, and/or MCCS2 in any of the processes described herein can also be determined by one skilled in the art (e.g., discussed in more detail below). For example, the volume and type(s) of buffer employed during the use of the MCCS, MCCS1, and/or MCCS2 in any of the processes described herein can be chosen in order to optimize one or more of the following in the purified recombinant protein (e.g., recombinant protein drug product): the overall yield of recombinant protein, the activity of the recombinant protein, the level of purity of the recombinant protein, and the removal of biological contaminants from a fluid including the recombinant protein (e.g., liquid culture medium) (e.g., absence of active viruses, mycobacteria, yeast, bacteria, or mammalian cells).

The MCCS, MCCS1, and/or MCCS2 can be a periodic counter current chromatography system (PCCS). A PCCS can, e.g., include two or more chromatography columns (e.g., three columns or four columns) that are switched in order to allow for the continuous elution of recombinant protein from the two or more chromatography columns. A PCCS can include two or more chromatography columns, two or more chromatographic membranes, or at least one chromatographic column and at least one chromatographic membrane. A column operation (cycle) generally consists of the load, wash, eluate, and regeneration steps. In PCCSs, multiple columns are used to run the same steps discretely and continuously in a cyclic fashion. Since the columns are operated in series, the flow through and wash from one column is captured by another column. This unique feature of PCCSs allows for loading of the resin close to its static binding capacity instead of to the dynamic binding capacity, as is typical during batch mode chromatography. As a result of the continuous cycling and elution, fluid entering a PCCS is processed continuously, and the eluate including recombinant protein is continuously produced.

Column-switching strategy is employed to advance from one step to another in a PCCS cycle. Examples of column switching that can be used in a PCCS are described in U.S. Provisional Patent Application Ser. Nos. 61/775,060 and 61/856,390. For example, a column switching method can employ two automated switching operations per column: the first of which is related to the initial product breakthrough, while the second coincides with column saturation. The determination of when the column switching operations should take place can be determined by monitoring the recombinant protein concentration (e.g., monitoring performed by UV monitoring) in the eluate from each chromatography column present in a PCCS. For example, column switching can be determined by any PAT tool capable of in-line measurement of recombinant protein concentration with feedback control. The PAT tool is capable of real-time in-line measurement of recombinant protein concentration with feedback control. As in known in the art, column switches can also be designed based on time or the amount of fluid (e.g., buffer) passed through the one or more chromatography column(s) and/or chromatographic membranes in the MCCS, MCCS1, and/or MCCS2.

In PCCSs, the residence time (RT) of the recombinant protein on the each chromatography column and/or chromatographic membrane present in the PCCS can be decreased without increasing the column/membrane size because the breakthrough from the first column/membrane can be captured on another column/membrane in the PCCS. A continuous process system can be designed to process liquid culture medium at any perfusion rate (D) by varying the column/membrane volume (V) and RT using the equation of: $V = D \ast RT$.

The one or more unit operations that can be performed by the MCCS or the MCC1 and/or MCCS2 used in the presently described processes include, for example, capturing the recombinant protein, inactivating viruses present in a fluid including the recombinant protein, purifying the recombinant protein, polishing the recombinant protein, holding a fluid including the recombinant protein (e.g., using any of the exemplary break tank(s) described herein), filtering or removing particulate material and/or cells from a fluid including the recombinant protein, and adjusting the ionic concentration and/or pH of a fluid including the recombinant protein.

In some embodiments, the MCCS or the MCCS1 includes at least one chromatographic column and/or chromatographic membrane that performs the unit operation of capturing the recombinant protein. The unit operation of capturing can be performed using at least one chromatography column and/or chromatography resin, e.g., that utilizes a capture mechanism. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Capturing can also be performed using a resin that can be used to perform cation exchange or anion exchange chromatography, molecular sieve chromatography, or hydrophobic interaction chromatography. Non-limiting resins that can be used to capture a recombinant protein are described herein. Additional examples of resins that can be used to capture a recombinant protein are known in the art.

The unit operation of inactivating viruses present in a fluid including the recombinant protein can be performed using a MCCS, MCCS1, and/or MCCS2 (e.g., that include(s), e.g., a chromatography column, a chromatography membrane, or a holding tank that is capable of incubating a fluid including the recombinant protein at a pH of between about 3.0 to 5.0 (e.g., between about 3.5 to about 4.5, between about 3.5 to about 4.25, between about 3.5 to about 4.0, between about 3.5 to about 3.8, or about 3.75) for a period of at least 30 minutes (e.g., a period of between about 30 minutes to 1.5 hours, a period of between about 30 minutes to 1.25 hours, a period of between about 0.75 hours to 1.25 hours, or a period of about 1 hour)).

The unit operation of purifying a recombinant protein can be performed using one or more MCCSs (e.g., a MCCS, MCCS1, and/or MCCS2) that include(s), e.g., a chromatography column or chromatographic membrane that includes a resin, e.g., that utilizes a capture system. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Purifying can also be performed using a resin that can be used to perform cation exchange or anion exchange chromatography, molecular sieve chromatography, or hydrophobic interaction chromatography. Non-limiting resins that can be used to purify a recombinant protein are described herein. Additional examples of resins that can be used to purify a recombinant protein are known in the art.

The unit operation of polishing a recombinant protein can be performed using one or more MCCSs (e.g., a MCCS, MCCS1, and/or MCCS) that include(s), e.g., a chromatography column or chromatographic membrane that includes a resin, e.g., that can be used to perform cation exchange, anion exchange, molecular sieve chromatography, or hydrophobic interaction chromatography. Non-limiting resins that can be used to polish a recombinant protein are described herein. Additional examples of resins that can be used to polish a recombinant protein are known in the art.

The unit operation of holding a fluid including the recombinant protein can be performed using an MCCS (e.g., a MCCS, MCCS1, and/or MCCS2) that includes at least one reservoir (e.g., a break tank) or a maximum of 1, 2, 3, 4, or 5 reservoir(s) (e.g., break tank(s)) in the MCCS or the MCCS1 and MCCS2 combined. For example, the reservoir(s) (e.g., break tank(s)) that can be used to achieve this unit operation can each have a volume of between about 1 mL to about 1 L (e.g., between about 1 mL to about 800 mL, between about 1 mL to about 600 mL, between about 1 mL to about 500 mL, between about 1 mL to about 400 mL, between about 1 mL to about 350 mL, between about 1 mL to about 300 mL, between about 10 mL and about 250 mL, between about 10 mL and about 200 mL, between about 10 mL and about 150 mL, or between about 10 mL to about 100 mL). The reservoir(s) (e.g., break tank(s)) used in the processes described herein can have a capacity that is, e.g., between 1 mL and about 300 mL, inclusive, e.g., between 1 mL and about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL, inclusive. Any of the reservoir(s) (e.g., break tank(s)) used (in any of the processes described herein) to hold fluid before it enters into the MCCS or MCCS1 can have a capacity that is, e.g., between 1 mL and about 100%, inclusive, between about 1 mL and about 90%, about 80%, about 70%, about 60%, about 50%, about 40%, about 30%, about 20%, about 10%, or about 5%, inclusive, of the loading volume of the first column of the MCCS or MCCS1. Any of the reservoir(s) (e.g., break tanks(s)) used to hold a eluate from MCCS1 (including the recombinant protein) before it enters the MCCS2 can have a capacity that is, e.g., between 1 mL and about 100%, inclusive, e.g., between about 1 mL and about 90%, about 80%, about 70%, about 60%, about 50%, about 40%, about 30%, about 20%, about 10%, or about 5%, inclusive, of the loading volume of the first column of the MCCS2.

The reservoir(s) (e.g., break tank(s)) can each hold the fluid including the recombinant protein for at least 10 minutes (e.g., at least 20 minutes, at least 30 minutes, at least 1 hour, at least 2 hours, at least 4 hours, or at least 6 hours). In other examples, the reservoir(s) (e.g., break tank(s)) only holds a recombinant protein for a total time period of, e.g., between about 5 minutes and less than about 6 hours, inclusive, e.g., between about 5 minutes and about 5 hours, about 4 hours, about 3 hours, about 2 hours, about 1 hour, or about 30 minutes, inclusive. The reservoir(s) (e.g., break tank(s)) can be used to both hold and refrigerate (e.g., at a temperature of less than 25° C., less than 15° C., or less than 10° C.) the fluid including the recombinant protein. The reservoir can have any shape, including a circular cylinder, an oval cylinder, or an approximately rectangular sealed and nonpermeable bag.

The unit operations of filtering a fluid including the recombinant protein can be performed using an MCCS (e.g., the MCCS, MCCS1, and/or MCCS2) that includes, e.g., a filter, or a chromatography column or chromatographic membrane that includes a molecular sieve resin. As is known in the art, a wide variety of submicron filters (e.g., a filter with a pore size of less than 1 μm, less than 0.5 μm, less than 0.3 μm, about 0.2 μm, less than 0.2 μm, less than 100 nm, less than 80 nm, less than 60 nm, less than 40 nm, less than 20 nm, or less than 10 nm) are available in the art that are capable of removing any precipitated material and/or cells (e.g., precipitated, unfolded protein; precipitated, unwanted host cell proteins; precipitated lipids; bacteria; yeast cells; fungal cells; mycobacteria; and/or mammalian cells). Filters having a pore size of about 0.2 μm or less than 0.2 μm are known to effectively remove bacteria from the fluid including the recombinant protein. As is known in the art, a chromatography column or a chromatographic membrane including a molecular sieve resin can also be used in an MCCS (e.g., the MCCS, MCCS1, and/or MCCS2) to perform the unit operation of filtering a fluid including a recombinant protein.

The unit operations of adjusting the ionic concentration and/or pH of a fluid including the recombinant protein can be performed using a MCCS (e.g., a MCCS, a MCCS1, and/or a MCCS2) that includes and utilizes a buffer adjustment reservoir (e.g., an in-line buffer adjustment reservoir) that adds a new buffer solution into a fluid that includes the recombinant protein (e.g., between columns within the MCCS, MCCS1, and/or MCCS2, or after the last column in a penultimate MCCS (e.g., the MCCS1) and before the fluid including the recombinant protein is fed into the first column of the next MCCS (e.g., the MCCS2)). As can be appreciated in the art, the in-line buffer adjustment reservoir can be any size (e.g., greater than 100 mL) and can include any buffered solution (e.g., a buffered solution that has one or more of: an increased or decreased pH as compared to the fluid including the recombinant protein, an increased or decreased ionic (e.g., salt) concentration compared to the fluid including the recombinant protein, and/or an increased or decreased concentration of an agent that competes with the recombinant protein for binding to resin present in at least one chromatographic column or at least one chromatographic membrane in an MCCS (e.g., the MCCS, MCCS1, and/or MCCS2)).

The MCCS, MCCS1, and/or MCCS2 can perform two or more unit operations. For example, the MCCS, MCCS1, and/or MCCS2 can each perform at least the following unit operations: capturing the recombinant protein and inactivating viruses present in the fluid including the recombinant protein; capturing the recombinant protein, inactivating viruses present in the fluid including the recombinant protein, and adjusting the ionic concentration and/or pH of a liquid including the recombinant protein; purifying the recombinant protein and polishing the recombinant protein; purifying the recombinant protein, polishing the recombinant protein, and filtering a fluid including the recombinant protein or removing precipitates and/or particular matter from a fluid including the recombinant protein; and purifying the recombinant protein, polishing the recombinant protein, filtering a fluid including the recombinant protein or removing precipitates and/or particulate matter from a fluid including the recombinant protein, and adjusting the ionic concentration and/or pH of a liquid including the recombinant protein.

Capturing the Recombinant Protein

The present processes include a step of capturing the recombinant protein using a MCCS or MCCS1. As can be appreciated in the art, the liquid culture medium including the recombinant protein can be continuously fed onto the MCCS or MCCS1 using a variety of different means. For example, the liquid culture medium can be actively pumped into the MCCS or MCCS1, or the liquid culture medium can be fed into the MCCS or MCCS1 using gravitational force. The liquid culture medium can be stored in a reservoir (e.g., a holding tank) before it is fed into the MCCS or MCCS1 or the liquid culture medium can be actively pumped from a bioreactor including a culture of cells (e.g., mammalian cells that secrete the recombinant protein into the culture medium) into the MCCS or MCCS1.

The liquid culture medium can be fed (loaded) into the MCCS or MCCS1 at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The liquid culture medium including the recombinant protein can be derived from any of the exemplary sources described herein or known in the art.

Some examples further include the optional step of filtering the liquid culture medium before it is fed into the MCCS or MCCS1. Any of the exemplary means of filtering a liquid culture medium or a fluid including the recombinant protein described herein, or any filtration means known in the art, can be used to filter the liquid culture medium including the recombinant protein before it is fed into the MCCS or MCCS1.

In the processes described herein, the capturing of the recombinant protein from the liquid culture medium is performed using the MCCS or MCCS1. As can be appreciated in the art, in order to achieve the capture of the recombinant protein, at least one chromatographic column or at least one chromatographic membrane in the MCCS or MCCS1 must include a resin that utilizes a capturing mechanism (e.g., any of the exemplary capturing mechanisms described herein), or includes a resin capable of performing cation exchange, anion exchange, molecular sieve, or hydrophobic interaction chromatography. For example, if the recombinant protein is an antibody or an antibody fragment, the capturing system can be a protein A-binding capturing mechanism or an antigen-binding capturing mechanism (where the capturing antigen is specifically recognized by the recombinant antibody or antibody fragment). If the recombinant protein is an enzyme, the capturing mechanism can use an antibody or antibody fragment that specifically binds to the enzyme to capture the recombinant enzyme, a substrate of the enzyme to capture the recombinant enzyme, a cofactor of the enzyme to capture the recombinant enzyme, or, if the recombinant enzyme includes a tag, a protein, metal chelate, or antibody (or antibody fragment) that specifically binds to the tag present in the recombinant enzyme. Non-limiting resins that can be used to capture a recombinant protein are described herein and additional resins that can be used to capture a recombinant protein are known in the art. One non-limiting example of resin that utilizes a protein A-binding capture mechanism is Mab Select SuRe™ resin (GE Healthcare, Piscataway, N.J.), JSR LifeSciences Amsphere ProA JWT203 (Sunnyvale, Calif.), and Kaneka KanCap A (Osaka, Japan).

Exemplary non-limiting sizes and shapes of the chromatography column(s) or chromatographic membrane(s) present in the MCCS or MCCS1 that can be used to capture the recombinant protein are described herein. The liquid culture medium fed (loaded) into the MCCS or MCCS1 can include, e.g., between about 0.05 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant protein). The mean time required for the recombinant protein to bind to the resin used to perform the unit operation of capturing can be, e.g., between about 5 seconds to about 10 minutes (e.g., between about 10 seconds to about 8 minutes, between about 10 seconds to about 7 minutes, between about 10 seconds to about 6 minutes, between about 10 seconds to about 5 minutes, between about 30 seconds to about 5 minutes, between about 1 minute to about 5 minutes, between about 10 seconds to about 4 minutes, between about 30 seconds to about 4 minutes, or between about 1 minute to about 4 minutes).

As can be appreciated in the art, in order to capture the recombinant protein using the chromatography column(s) or chromatographic membrane(s) present in the MCCS or MCCS1, one must perform the sequential chromatographic steps of loading, washing, eluting, and regenerating the chromatography column(s) or chromatography membrane(s) present in the MCCS or MCCS1. Any of the exemplary flow rates, buffer volumes, and/or lengths of time allotted for each sequential chromatographic step described herein can be used in the one or more of these different sequential chromatographic steps (e.g., one or more of the sequential chromatographic steps of loading, washing, eluting, and regenerating the chromatography column(s) or chromatography membrane(s) present in the MCCS or MCCS1 that are used for capturing the recombinant protein). Non-limiting flow rates, buffer volumes, and/or lengths of time allotted for each sequential chromatographic step that can be used for capturing chromatographic column(s) and/or chromatographic membrane(s) in the MCCS or MCCS1 (e.g., a PCCS or PCCS1) are provided below. In addition, exemplary buffers that can be used in the MCCS and/or MCCS1 are described below.

The MCCS or MCCS1 including at least one chromatographic column and/or chromatographic membrane including a resin that can perform the unit operation of capturing (e.g., any of exemplary resins that can be used for capturing described herein) can be loaded with the liquid culture medium including a recombinant protein using any of loading flow rates (fed rates) described above. In some examples, a single chromatographic column or single chromatographic membrane including a resin that is capable of performing the unit operation of capturing is loaded in, e.g., between about 10 minutes to about 90 minutes (e.g., between about 15 minutes and about 90 minutes, between about 20 minutes and 80 minutes, between about 30 minutes and 80 minutes, between about 40 minutes and about 80 minutes, between about 50 minutes and about 80 minutes, and between about 60 minutes and 80 minutes). In some examples, wherein the MCCS or MCCS1 includes at least two chromatographic columns that include a resin that is capable of performing the unit operation of capturing in series, the time required to load two of the chromatographic columns in series is, e.g., between about 50 minutes to about 180 minutes (e.g., between about 60 minutes and about 180 minutes, between about 70 minutes and about 180 minutes, between about 80 minutes and about 180 minutes, between about 90 minutes and about 180 minutes, between about 100 minutes and about 180 minutes, between about 110 minutes and 150 minutes, and between about 125 minutes and about 145 minutes).

Following the loading of the recombinant protein onto the at least one chromatographic column or chromatographic membrane in the MCCS or MCCS1 that includes a resin that is capable of performing the unit operation of capturing, the at least one chromatographic column or chromatographic membrane is washed with at least one washing buffer. As can be appreciated in the art, the at least one (e.g., two, three, or four) washing buffer is meant to elute all or most of proteins that are not the recombinant protein from the at least one chromatography column or chromatographic membrane, while not disturbing the interaction of the recombinant protein with the resin.

The wash buffer can be passed through the at least one chromatography column or chromatographic membrane at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The volume of wash buffer used (e.g., combined total volume of wash buffer used when more than one wash buffer is used) can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the washing can be, e.g., between about 2 minutes to about 3 hours (e.g., between about 2 minutes to about 2.5 hours, between about 2 minutes to about 2.0 hours, between about 5 minutes to about 1.5 hours, between about 10 minutes to about 1.5 hours, between about 10 minutes to about 1.25 hours, between about 20 minutes to about 1.25 hours, or between about 30 minutes to about 1 hour).

Following the washing of the at least one chromatographic column or chromatographic membrane in the MCCS or MCCS1 that includes a resin that is capable of performing the unit operation of capturing, the recombinant protein is eluted from the at least one chromatographic column or chromatographic membrane by passing an elution buffer through the at least one chromatographic column or chromatographic membrane in the MCCS or MCCS1 that includes a resin that is capable of performing the unit operation of capturing. The elution buffer can be passed through the at least one chromatography column or chromatographic membrane that includes a resin that is capable of performing the unit operation of capturing at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, or between about 1.0 mL/minute and about 15.0 mL/minute). The volume of elution buffer used to elute the recombinant protein from each of the at least one chromatographic column or chromatographic membrane including a resin that is capable of performing the unit operation of purifying can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the eluting can be, e.g., between about 2 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, or between about 20 minutes and about 40 minutes). Non-limiting examples of elution buffers that can be used in these methods will depend on the capture mechanism and/or the recombinant protein. For example, an elution buffer can include a different concentration of salt (e.g., increased salt concentration), a different pH (e.g., an increased or decreased salt concentration), or a molecule that will compete with the recombinant protein for binding to the resin that is capable of performing the unit operation of capturing. Examples of such elution buffers for each exemplary capture mechanism described herein are well known in the art.

Following the elution of the recombinant protein from the at least one chromatographic column or chromatographic membrane in the MCCS or the MCCS1 that includes a resin that is capable of performing the unit operation of capturing, and before the next volume of liquid culture medium can be loaded onto the at least one chromatographic column or chromatographic membrane, the at least one chromatography column or chromatographic membrane must be equilibrated using an regeneration buffer. The regeneration buffer can be passed through the at least one chromatography column or chromatographic membrane that includes a resin that is capable of performing the unit operation of capturing at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, or between about 1.0 mL/minute and about 15.0 mL/minute). The volume of regeneration buffer used to equilibrate the at least one chromatography column or chromatographic membrane that includes a resin that is capable of performing the unit operation of capturing can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 2×CV to about 5×CV, about 4×CV to about 11×CV, about 5×CV to about 11×CV, or about 5×CV to about 10×CV).

In some of the processes described herein, the MCCS or MCCS1 includes a reservoir that holds a fluid including the recombinant protein at low pH (e.g., a pH below 4.6, below 4.4, below 4.2, below 4.0, below 3.8, below 3.6, below 3.4, below 3.2, or below 3.0) for, e.g., about 1 minute to 1.5 hours (e.g., about 1 hour), and inactivates the viruses present in a fluid including the recombinant protein. An example of a reservoir that can be used to perform the unit operation of inactivating viruses is a stir flask (e.g., 500-mL stir flask, e.g., a 500-mL stir flask with a programmed stir plate) that is capable of holding a fluid including a recombinant protein for, e.g., about 1 minute to 1.5 hours, e.g., before the fluid including the recombinant protein is fed into the MCCS2. The reservoir that is used to perform the unit operation of inactivation of viruses can be a 500-mL stir flask with a programmed stir plate (e.g., a stir plate programmed to mix (e.g., periodically mix) the fluid within the reservoir, e.g., every 4 hours). Another example of a reservoir that can be used to perform the unit operation of inactivation of viruses is a plastic bag (e.g., 500-mL plastic bag) that is capable of holding a fluid including a recombinant protein for, e.g., about 1 minute to 1.5 hours, e.g., before the fluid including the recombinant protein is fed into the MCCS2. In some examples, the fluid including the recombinant protein can already have a low pH (e.g., a pH below 4.6, below 4.4, below 4.2, below 4.0, below 3.8, below 3.6, below 3.4, below 3.2, or below 3.0) when it is fed into the reservoir that is used to perform the unit operation of viral inactivation. As can be appreciated by those skilled in the art, a variety of other means can be used to perform the unit operation of inactivating viruses. For example, UV irradiation of a fluid including the recombinant protein can also be used to perform the unit operation of inactivating viruses. Non-limiting examples of reservoirs that can be used to perform the unit operation of inactivation of viruses present in a fluid including the recombinant protein are described herein.

The MCCS or MCCS1 can include a PCCS including four chromatography columns, where at least three of the four chromatography columns perform the unit operation of capturing the recombinant protein from the liquid culture medium (e.g., using an MCCS that includes any of the at least one chromatography columns that include a resin that is capable of performing the unit operation of capturing (e.g., any of those described herein)). In these examples, the fourth-column of the PCC can perform the unit operation of inactivating viruses in a fluid that includes the recombinant protein (e.g., any of the exemplary columns described herein that can be used to achieve viral inactivation of a fluid including the recombinant protein).

In some examples, a fluid including the recombinant protein is continuously eluted from the MCCS1 (e.g., PCCS1), and is continuously fed into the MCCS2 (e.g., PCCS2). The percent of the recombinant protein recovered in the eluate of the MCCS or MCCS1 (e.g., PCCS or PCCS1) can be, e.g., at least 70%, at least 72%, at least 74%, at least 76%, at least 78%, at least 80%, at least 82%, at least 84%, at least 86%, at least 88%, at least 90%, at least 92%, at least 94%, at least 96%, or at least 98%). The eluate from the MCCS1 (e.g., PCCS1) can be fed into the MCCS2 (e.g., PCCS2) using a variety of means known in the art (e.g., tubing). The eluate of the MCCS1 (e.g., PCCS1) can be fed into the MCCS2 (e.g., PCCS2) at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, between about 15 mL/minute to about 25 mL/minute, or between about 1.0 mL/minute and about 15.0 mL/minute).

Some processes described herein can further include a step of adjusting the ionic concentration and/or pH of the eluate from the MCCS1 (e.g., PCCS1) before it is fed into the MCCS2 (e.g., PCCS2). As described herein, the ionic concentration and/or pH of the eluate from the MCCS1 (e.g., PCCS1) can be adjusted (before it is fed into the MCCS2) by adding a buffer to the eluate (e.g., through the use of an in-line buffer adjustment reservoir). The buffer can be added to the eluate from the MCCS1 at a flow rate of, e.g., between about 0.1 mL/minute to about 15 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, or between about 0.5 mL/minute to about 5 mL/minute).

The processes described herein can further include a step of holding or storing (and optionally also refrigerating) the eluate from the MCCS1 prior to feeding the eluate from the MCCS1 into the MCCS2. As described herein, this holding or storing step can be performed using any of the reservoirs (e.g., back-up tanks) described herein.

The processes described herein can also include a step of filtering the eluate from the MCCS1 before the eluate is fed into the MCCS2. Any of the exemplary filters or methods for filtration described herein can be used to filter the eluate from the MCCS1 before the eluate is fed into the MCCS2.

Polishing and Purifying the Recombinant Protein

The MCCS, MCCS1, and/or MCCS2 can be used to perform the unit operation of purifying and polishing the recombinant protein. For example, the MCCS2 can be used to perform the operation of purifying and polishing the recombinant protein and the eluate from the MCCS2 is a protein drug substance. The MCCS, MCCS1, and/or MCCS2 can include at least one (e.g., two, three, or four) chromatography column or chromatographic membrane that can be used to perform the unit operation of purifying a recombinant protein, and at least one (e.g., two, three, or four) chromatography column or chromatographic membrane that can be used to perform the unit operation of polishing the recombinant protein.

The at least one chromatography column or chromatographic membrane that can be used to perform the unit operation of purifying the recombinant protein can include a resin that utilizes a capture mechanism (e.g., any of the capture mechanisms described herein or known in the art), or a resin that can be used to perform anion exchange, cation exchange, molecular sieve, or hydrophobic interaction chromatography. The at least one chromatography column or chromatographic membrane that can be used to perform the unit of operation of polishing the recombinant protein can include a resin that can be used to perform anion exchange, cation exchange, molecular sieve, or hydrophobic interaction chromatography (e.g., any of the exemplary resins for performing anion exchange, cation exchange, molecular sieve, or hydrophobic interaction chromatography described herein or known in the art).

The size, shape, and volume of the at least one chromatography column or chromatography membrane that can be used to perform the unit of operation of purifying the recombinant protein, and/or the size and shape of the at least one chromatographic membrane that can be used to perform the unit of operation of polishing the recombinant protein can any of combination of the exemplary sizes, shapes, and volumes of chromatography columns or chromatographic membranes described herein. As can be appreciated by one skilled in the art, the step of purifying or polishing a recombinant protein can, e.g., include the steps of loading, washing, eluting, and equilibrating the at least one chromatography column or chromatographic membrane used to perform the unit of operation of purifying or polishing the recombinant protein. Typically, the elution buffer coming out of a chromatography column or chromatographic membrane used to perform the unit operation of purifying includes the recombinant protein. Typically, the loading and/or wash buffer coming out of a chromatography column or chromatographic membrane used to perform the unit operation of polishing includes the recombinant protein.

For example, the size of the at least one chromatography column or chromatographic membrane that can be used to perform unit operation of purifying the recombinant protein can have a volume of, e.g., between about 2.0 mL to about 200 mL (e.g., between about 2.0 mL to about 180 mL, between about 2.0 mL to about 160 mL, between about 2.0 mL to about 140 mL, between about 2.0 mL to about 120 mL, between about 2.0 mL to about 100 mL, between about 2.0 mL to about 80 mL, between about 2.0 mL to about 60 mL, between about 2.0 mL to about 40 mL, between about 5.0 mL to about 40 mL, between about 2.0 mL to about 30 mL, between about 5.0 mL to about 30 mL, or between about 2.0 mL to about 25 mL). The flow rate of the fluid including the recombinant protein as it is loaded onto the at least one chromatography column or at least one chromatographic that can be used to perform the unit operation of purifying the recombinant protein can be, e.g., between about 0.1 mL/minute to about 25 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, between about 0.1 mL/minute to about 3 mL/minute, between about 0.1 mL/minute to about 2 mL/minute, or about 0.2 mL/minute to about 4 mL/minute). The concentration of the recombinant protein in the fluid loaded onto the at least one chromatography column or chromatographic membrane that can be used to perform the unit operation of purifying the recombinant protein can be, e.g., between about 0.05 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant protein). The resin in the at least one chromatography column or chromatographic membrane used to perform unit operation of purifying can be a resin that can be used to perform anion exchange or cation exchange chromatography. The resin in the at least one chromatography column or chromatographic membrane that is used to perform the unit operation of purifying can be a cationic exchange resin (e.g., Capto-S resin, GE Healthcare Life Sciences, Piscataway, N.J.).

Following the loading of the recombinant protein onto the at least one chromatographic column or chromatographic membrane that can be used to perform the unit operation of purifying the recombinant protein, the at least one chromatographic column or chromatographic membrane is washed with at least one washing buffer. As can be appreciated in the art, the at least one (e.g., two, three, or four) washing buffer is meant to elute all proteins that are not the recombinant protein from the at least one chromatography column or chromatographic membrane, while not disturbing the interaction of the recombinant protein with the resin or otherwise eluting the recombinant protein.

The wash buffer can be passed through the at least one chromatography column or chromatographic membrane at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, or between about 1.0 mL/minute and about 15.0 mL/minute). The volume of wash buffer used (e.g., combined total volume of wash buffer used when more than one wash buffer is used) can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV). The total time of the washing can be, e.g., between about 2 minutes to about 3 hours (e.g., between about 2 minutes to about 2.5 hours, between about 2 minutes to about 2.0 hours, between about 5 minutes to about 1.5 hours, between about 10 minutes to about 1.5 hours, between about 10 minutes to about 1.25 hours, between about 20 minutes to about 1.25 hours, between about 30 minutes to about 1 hour, between about 2 minutes and 10 minutes, between about 2 minutes and 15 minutes, or between about 2 minutes and 30 minutes).

Following the washing of the at least one chromatographic column or chromatographic membrane used to perform the unit operation of purifying the recombinant protein, the recombinant protein is eluted from the at least one chromatographic column or chromatographic membrane by passing an elution buffer through the at least one chromatographic column or chromatographic membrane used to perform the unit operation of purifying the recombinant protein. The elution buffer can be passed through the at least one chromatography column or chromatographic membrane that can be used to perform the unit operation of purifying the recombinant protein at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, or between about 1.0 mL/minute and about 15.0 mL/minute). The volume of elution buffer used to elute the recombinant protein from each of the at least one chromatographic column or chromatographic membrane that can be used to perform the unit operation of purifying the recombinant protein can be, e.g., between about 1× column volume (CV) to about 25×CV (e.g., between about 1×CV to about 20×CV, between about 15×CV and about 25×CV, between about 1×CV to about 14×CV, about 1×CV to about 13×CV, about 1×CV to about 12×CV, about 1× CV to about 11×CV, about 2×CV to about 11×CV, about 3×CV to about 11×CV, about 4×CV to about 11×CV, about 5×CV to about 11×CV, or about 5×CV to about 10×CV). The total time of the eluting can be, e.g., between about 2 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, between about 20 minutes and about 40 minutes, or between about 30 minutes and 1.0 hour). Non-limiting examples of elution buffers that can be used in these methods will depend on the resin and/or the biophysical properties of the recombinant protein. For example, an elution buffer can include a different concentration of salt (e.g., increased salt concentration), a different pH (e.g., an increased or decreased salt concentration), or a molecule that will compete with the recombinant protein for binding to the resin. Examples of such elution buffers for each of the exemplary capture mechanisms described herein are well known in the art.

Following the elution of the recombinant protein from the at least one chromatographic column or chromatographic membrane used to perform the unit operation of purifying the recombinant protein, and before the next volume of fluid including a recombinant protein can be loaded onto the at least one chromatographic column or chromatographic membrane, the at least one chromatography column or chromatographic membrane must be equilibrated using an regeneration buffer. The regeneration buffer can be passed through the at least one chromatography column or chromatographic membrane used to perform the unit operation of purifying the recombinant protein at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, or between about 1.0 mL/minute and about 15.0 mL/minute). The volume of regeneration buffer used to equilibrate the at least one chromatography column or chromatographic membrane that includes a resin that can be used to perform the unit operation of purifying the recombinant protein can be, e.g., between about 1× column volume (CV) to about 15×CV (e.g., between about 1×CV to about 14×CV, between about 1×CV to about 13×CV, between about 1×CV to about 12×CV, between about 1×CV to about 11×CV, between about 2×CV to about 11×CV, between about 3×CV to about 11×CV, between about 2×CV to about 5×CV, between about 2.5×CV to about 7.5×CV, between about 4×CV to about 11×CV, between about 5×CV to about 11×CV, or between about 5×CV to about 10×CV). The concentration of recombinant protein in the eluate of the at least one chromatography column or chromatographic membrane used to perform the unit operation of purifying the recombinant protein can be, e.g., between about 0.05 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 2.5 mg/mL and about 7.5 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant protein).

The at least one chromatography column or chromatographic membrane that can be used to perform the unit operation of polishing the recombinant protein can include a resin that can be used to perform cation exchange, anion exchange, or molecular sieve chromatography. As can be appreciated in the art, polishing a recombinant protein using the at least one chromatography column or chromatography membrane that can be used to perform the unit operation of polishing the recombinant protein can include, e.g., the steps of loading, chasing, and regenerating the at least one chromatography column or chromatographic membrane that can be used to perform the unit operation of polishing the recombinant protein. For example, when the steps of loading, chasing, and regenerating are used to perform the polishing, the recombinant protein does not bind the resin in the at least one chromatography column or chromatography membrane that is used to perform the unit operation of polishing the recombinant protein, and the recombinant protein is eluted from the at least one chromatography column or chromatographic membrane in the loading and chasing steps, and the regenerating step is used to remove any impurities from the at least one chromatography column or chromatographic membrane before additional fluid including the recombinant protein can be loaded onto the at least one chromatography column or chromatographic membrane. Exemplary flow rates and buffer volumes to be used in each of the loading, chasing, and regenerating steps are described below.

The size, shape, and volume of the at least one chromatography column or chromatography membrane that can be used to perform the unit operation of polishing the recombinant protein, and/or the size and shape of the at least one chromatographic membrane that can be used to perform the unit operation of polishing the recombinant protein can any of combination of the exemplary sizes, shapes, and volumes of chromatography columns or chromatographic membranes described herein. For example, the size of the at least one chromatography column or chromatographic membrane that can be used to perform the unit operation of polishing the recombinant protein can have a volume of, e.g., between about 0.5 mL to about 200 mL (e.g., between about 0.5 mL to about 180 mL, between about 0.5 mL to about 160 mL, between about 0.5 mL to about 140 mL, between about 0.5 mL to about 120 mL, between about 0.5 mL to about 100 mL, between about 0.5 mL to about 80 mL, between about 0.5 mL to about 60 mL, between about 0.5 mL to about 40 mL, between about 5.0 mL to about 40 mL, between about 0.5 mL to about 30 mL, between about 5.0 mL to about 30 mL, between about 0.5 mL to about 25 mL, between about 0.2 mL to about 10 mL, or between about 0.2 mL to about 5 mL). The flow rate of the fluid including the recombinant protein as it is loaded onto the at least one chromatography column or chromatographic membrane that can be used to perform the unit operation of polishing the recombinant protein can be, e.g., between about 0.1 mL/minute to about 25 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, between about 0.1 mL/minute to about 3 mL/minute, between about 2 mL/minute and about 6 mL/minute, between about 0.1 mL/minute to about 2 mL/minute, or about 0.2 mL/minute to about 4 mL/minute). The total volume of fluid including a recombinant protein loaded onto the at least one chromatography column or chromatographic membrane that can be used to perform the unit operation of polishing the recombinant protein can be, e.g., between about 1.0 mL to about 250 mL (e.g., between about 1.0 mL to about 225 mL, between about 1.0 mL to about 200 mL, between about 1.0 mL to about 175 mL, between about 1.0 mL to about 150 mL, between about 100 mL to about 125 mL, between about 100 mL to about 150 mL, between about 1.0 mL to about 150 mL, between about 1.0 mL to about 125 mL, between about 1.0 mL to about 100 mL, between about 1.0 mL to about 75 mL, between about 1.0 mL to about 50 mL, or between about 1.0 mL to about 25 mL). The resin in the at least one chromatography column or chromatographic membrane used to perform the polishing can be an anion exchange or cation exchange resin. The resin in the at least one chromatography column or chromatographic membrane that is used to perform the unit operation of polishing can be a cationic exchange resin (e.g., Sartobind® Q resin, Sartorius, Goettingen, Germany).

Following the loading step, a chasing step is performed (e.g., a chase buffer is passed through the at least one chromatography membrane or chromatographic membrane to collect the recombinant protein which does not substantially bind to the at least one chromatography column or chromatographic membrane). In these examples, the chase buffer can be passed through the at least one chromatography column or chromatographic membrane at a flow rate of between about 0.2 mL/minute to about 50 mL/minute (e.g., between about 1 mL/minute to about 40 mL/minute, between about 1 mL/minute to about 30 mL/minute, between about 5 mL/minute to about 45 mL/minute, between about 10 mL/minute to about 40 mL/minute, between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, or between about 1.0 mL/minute and about 15.0 mL/minute). The volume of chase buffer used can be, e.g., between about 1× column volume (CV) to about 100×CV (e.g., between about 1×CV to about 90×CV, between about 1×CV to about 80×CV, between about 1×CV to about 70×CV, between about 1×CV to about 60×CV, between about 1× to about 50×CV, between about 1×CV to about 40×CV, between about 1×CV to about 30×CV, between about 1×CV to about 20×CV, between about 1×CV to about 15×CV, between about 5×CV to about 20×CV, between about 5×CV to about 30×CV, between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV). The total time of the chasing can be, e.g., between about 1 minute to about 3 hours (e.g., between about 1 minute to about 2.5 hours, between about 1 minute to about 2.0 hours, between about 1 minute to about 1.5 hours, between about 2 minutes to about 1.5 hours, between about 1 minute to about 1.25 hours, between about 2 minutes to about 1.25 hours, between about 1 minute to about 5 minutes, between about 1 minute to about 10 minutes, between about 2 minutes to about 4 minutes, between about 30 minutes to about 1 hour, between about 2 minutes to about 10 minutes, between about 2 minutes to about 15 minutes, or between about 2 minutes to about 30 minutes). The combined concentration of recombinant protein present in the eluate coming through the column in the loading step and the chasing step can be, e.g., between about 0.1 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 2.5 mg/mL and about 7.5 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, between about 0.5 mg/mL to about 10 mg/mL, or between about 1 mg/mL and about 5 mg/mL recombinant protein).

Following the chasing step and before the next volume of fluid including the recombinant protein can be loaded onto the at least one chromatographic column or chromatographic membrane that can be used to perform the unit operation of polishing, the at least one chromatography column or chromatographic membrane must be regenerated using a regeneration buffer. The regeneration buffer can be passed through the at least one chromatography column or chromatographic membrane that can be used to perform the unit operation of polishing the recombinant protein at a flow rate of, e.g., between about 0.2 mL/minute to about 50 mL/minute (e.g., between about 1 mL/minute to about 40 mL/minute, between about 1 mL/minute to about 30 mL/minute, between about 5 mL/minute to about 45 mL/minute, between about 10 mL/minute to about 40 mL/minute, between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, or between about 1.0 mL/minute and about 15.0 mL/minute). The volume of regeneration buffer used to regenerate the at least one chromatography column or chromatographic membrane that can be used to perform the unit operation of polishing can be, e.g., between about 1× column volume (CV) to about 500×CV (e.g., between about 1×CV to about 450×CV, between about 1×CV to about 400×CV, between about 1×CV to about 350×CV, between about 1×CV to about 300×CV, between about 1×CV to about 250×CV, between about 1×CV to about 200×CV, between about 1×CV to about 150×CV, between about 1×CV to about 100×CV, between about 1×CV to about 90×CV, between about 1×CV to about 80×CV, between about 1×CV to about 70×CV, between about 1×CV to about 60×CV, between about 1× to about 50×CV, between about 1×CV to about 40×CV, between about 1×CV to about 30×CV, between about 1×CV to about 20×CV, between about 1×CV to about 15×CV, between about 5×CV to about 20×CV, between about 5×CV to about 30×CV, between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV).

In other examples, the one or more chromatography column(s) and/or chromatographic membranes used to perform the unit operation of polishing include a resin that selectively binds or retains the impurities present in a fluid including the recombinant protein, and instead of regenerating the one or more column(s) and/or membrane(s), the one or more column(s) and/or membrane(s) are replaced (e.g., replaced with a substantially similar column(s) and/or membrane(s)) once the binding capacity of the resin in the one or more column(s) and/or membrane(s) has been reached or is substantially close to being reached.

In some examples of these processes described herein, the MCCS2 includes a PCCS including three chromatography columns and one chromatographic membrane, e.g., where the three chromatography columns in the PCCS perform the unit operation of purifying the recombinant protein (e.g., using at least one chromatography column(s) that can be used to perform the unit of operation of purifying the protein) and the chromatographic membrane in the PCCS performs the unit operation of polishing the recombinant protein. In these examples, the chromatographic membrane in the PCCS that can be used to perform the unit operation of polishing the therapeutic protein can be any of the exemplary chromatographic membranes described herein that can be used to perform the unit operation of polishing the recombinant protein. Any of the column switching methods described herein can be used to determine when the first three chromatography columns and the chromatographic membrane in the PCCS in this example can be switched.

Some embodiments of this example can further include a step of adjusting the ionic concentration and/or pH of the eluate from the three chromatographic columns in the PCCS before the eluate is fed into the chromatographic membrane in the PCCS. As described herein, the ionic concentration and/or pH of the eluate from the three chromatography columns in PCCS can be adjusted (before it is fed into the chromatographic membrane in the PCCS in this example)) by adding a buffer to the eluate of the three chromatography columns in the PCCS (e.g., through the use of an in-line buffer adjustment reservoir). The buffer can be added to the eluate at a flow rate of, e.g., between about 0.1 mL/minute to about 15 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, or between about 0.5 mL/minute to about 5 mL/minute).

These examples can further include a step of holding or storing the eluate from the three chromatography columns in the PCCS in this example prior to feeding the eluate into the chromatographic membrane (chromatographic membrane that can be used to perform the unit operation of polishing the recombinant protein). As described herein, this holding or storing step can be performed using any of the reservoirs (e.g., back-up tanks) described herein.

These examples can also include a step of filtering the eluate from the chromatographic membrane in the exemplary PCCS system (eluate of the chromatographic membrane that can be used to perform the unit operation of polishing the recombinant protein). Any of the exemplary filters or methods for filtration described herein can be used to filter the eluate from the chromatographic membrane in this exemplary PCCS (eluate of the chromatographic membrane that can be used to perform the unit operation of polishing the recombinant protein).

As can be appreciated by those in the art, the purified recombinant protein can be periodically eluted from the MCCS or MCCS2 using any of the processes described herein. For example, any of the processes described herein can elute the purified recombinant protein for a duration of, e.g., between about 30 seconds and about 5 hours (e.g., between about 1 minute and about 4 hours, between about 1 minute and about 3 hours, between about 1 minute and about 2 hours, between about 1 minute or about 1.5 hours, between about 1 minute and about 1 hour, or between about 1 minute and about 30 minutes) at a frequency of, e.g., between about 1 minute and about 6 hours (e.g., between about 1 minute and about 5 hours, between about 1 minute and about 4 hours, between about 1 minute and about 3 hours, between about 1 minute and 2 hours, between about 1 minute and 1 hour, or between about 1 minute and 30 minutes), depending on, e.g., the chromatography column(s) and/or chromatographic membrane(s) used in the MCCS or the MCCS1 and MCCS2.

Culturing Methods

Some of the processes described herein further include a step of culturing cells (e.g., recombinant mammalian cells) that secrete a recombinant protein in a bioreactor (e.g., a perfusion or fed-batch bioreactor) that includes a liquid culture medium, wherein a volume of the liquid culture medium that is substantially free of cells (e.g., mammalian cells) is continuously or periodically removed from the bioreactor (e.g., perfusion bioreactor) and fed into the MCCS or MCCS1. The bioreactor can have a volume of, e.g., between about 1 L to about 10,000 L (e.g., between about 1 L to about 50 L, between about 50 L to about 500 L, between about 500 L to about 1000 L, between 500 L to about 5000 L, between about 500 L to about 10,000 L, between about 5000 L to about 10,000 L, between about 1 L and about 10,000 L, between about 1 L and about 8,000 L, between about 1 L and about 6,000 L, between about 1 L and about 5,000 L, between about 100 L and about 5,000 L, between about 10 L and about 100 L, between about 10 L and about 4,000 L, between about 10 L and about 3,000 L, between about 10 L and about 2,000 L, or between about 10 L and about 1,000 L). The amount of liquid culture medium present in a bioreactor can be, e.g., between about between about 0.5 L to about 5,000 L (e.g., between about 0.5 L to about 25 L, between about 25 L to about 250 L, between about 250 L to about 500 L, between 250 L to about 2500 L, between about 250 L to about 5,000 L, between about 2500 L to about 5,000 L, between about 0.5 L and about 5,000 L, between about 0.5 L and about 4,000 L, between about 0.5 L and about 3,000 L, between about 0.5 L and about 2,500 L, between about 50 L and about 2,500 L, between about 5 L and about 50 L, between about 5 L and about 2,000 L, between about 5 L and about 1,500 L, between about 5 L and about 1,000 L, or between about 5 L and about 500 L). Culturing cells can be performed, e.g., using a fed-batch bioreactor or a perfusion bioreactor. Non-limiting examples and different aspects of culturing cells (e.g., culturing mammalian cells) are described below and can be used in any combination.

Cells

The cells that are cultured in some of the processes described herein can be bacteria (e.g., gram negative bacteria), yeast (e.g., *Saccharomyces cerevisiae, Pichia pastoris, Hansenula polymorpha, Kluyveromyces lactis, Schizosaccharomyces pombe, Yarrowia lipolytica,* or *Arxula adeninivorans*), or mammalian cells. The mammalian cell can be a cell that grows in suspension or an adherent cell. Non-limiting examples of mammalian cells that can be cultured in any of the processes described herein include: Chinese hamster ovary (CHO) cells (e.g., CHO DG44 cells or CHO-K1s cells), Sp2.0, myeloma cells (e.g., NS/0), B-cells, hybridoma cells, T-cells, human embryonic kidney (HEK) cells (e.g., HEK 293E and HEK 293F), African green monkey kidney epithelial cells (Vero) cells, and Madin-Darby Canine (Cocker Spaniel) kidney epithelial cells (MDCK) cells. In some examples where an adherent cell is cultured, the culture can also include a plurality of microcarriers (e.g., microcarriers that include one or more pores). Additional mammalian cells that can be cultured in any of the processes described herein are known in the art.

The mammalian cell can include a recombinant nucleic acid (e.g., a nucleic acid stably integrated in the mammalian cell's genome) that encodes a recombinant protein (e.g., a recombinant protein). Non-limiting examples of recombinant nucleic acids that encode exemplary recombinant proteins are described below, as are recombinant proteins that can be produced using the methods described herein. In some instances, the mammalian cell that is cultured in a bioreactor (e.g., any of the bioreactors described herein) was derived from a larger culture.

A nucleic acid encoding a recombinant protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the mammalian cell (transient transfection), while in others the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a (β-actin promoter and CMV promoter, or an inducible promoter). A vector including the nucleic acid can, if desired, also include a selectable marker (e.g., a gene that confers hygromycin, puromycin, or neomycin resistance to the mammalian cell).

In some instances, the recombinant protein is a secreted protein and is released by the mammalian cell into the extracellular medium (e.g., the first and/or second liquid culture medium). For example, a nucleic acid sequence encoding a soluble recombinant protein can include a sequence that encodes a secretion signal peptide at the N- or C-terminus of the recombinant protein, which is cleaved by an enzyme present in the mammalian cell, and subsequently released into the extracellular medium (e.g., the first and/or second liquid culture medium).

Culture Media

Liquid culture media are known in the art. The liquid culture media (e.g., a first and/or second tissue culture medium) can be supplemented with a mammalian serum (e.g., fetal calf serum and bovine serum), and/or a growth hormone or growth factor (e.g., insulin, transferrin, and epidermal growth factor). Alternatively or in addition, the liquid culture media (e.g., a first and/or second liquid culture medium) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically includes an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid culture medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells (e.g., mammalian cells) in any of the methods described herein are known in the art. Medium components that also may be useful in the present processes include, but are not limited to, chemically-defined (CD) hydrolysates, e.g., CD peptone, CD polypeptides (two or more amino acids), and CD growth factors. Additional examples of liquid tissue culture medium and medium components are known in the art.

Skilled practitioners will appreciate that the first liquid culture medium and the second liquid culture medium described herein can be the same type of media or different media.

Additional Features of Exemplary Bioreactors

The interior surface of any of the bioreactors described herein may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an ATF system or the cell filtering system described in U.S. Provisional Patent Application Ser. No. 61/878,502).

Temperature

The step of culturing of mammalian cells can be performed at a temperature of about 31° C. to about 40° C. Skilled practitioners will appreciate that the temperature can be changed at specific time point(s) in during the culturing step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the bioreactor with the cell (e.g., mammalian cell). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

$CO_2$

The culturing step described herein can further include exposing the liquid culture medium in the bioreactor to an atmosphere including at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$).

Perfusion Bioreactor

The culturing step described herein can be performed using a perfusion bioreactor. Culturing a cell (e.g., a mammalian cell) in a perfusion bioreactor includes the removal from the bioreactor of a first volume of a first liquid culture medium (e.g., including any concentration of mammalian cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, or between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, or between 4% and 30%) of the volume of the bioreactor or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume.

Skilled practitioners will appreciate that the first liquid culture medium and the second liquid culture medium can be the same type of media. In other instances, the first liquid culture medium and the second liquid culture medium can be different.

The first volume of the first liquid culture medium can be removed, e.g., by a mechanical system that can remove the first volume of the first liquid culture medium from the bioreactor (e.g., the first volume of the first liquid culture medium that is substantially free of cells from the bioreactor). Alternatively or in addition, the first volume of the first liquid culture medium can be removed by seeping or gravity flow of the first volume of the first liquid culture medium through a sterile membrane with a molecular weight cut-off that excludes the cell (e.g., mammalian cell).

The second volume of the second liquid culture medium can be added to the first liquid culture medium in an automated fashion, e.g., by perfusion pump.

In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell.

Fed-Batch Bioreactor

The culturing step described herein can be performed using a fed-batch bioreactor. Culturing a cell in a fed-batch bioreactor includes, over the majority of the culturing period, the addition (e.g., periodic or continuous addition) to the first liquid culture medium of a second volume of a second liquid culture medium. The adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, or between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, or between 4% and 30%) of the volume of the bioreactor or the first liquid culture medium volume. The second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the second volume of the second liquid culture medium is added (volume/unit of time) can be varied over the entire or part of the culturing period. For example, the volume of the second liquid culture medium added can change (e.g., gradually increase) over each 24-hour period (or alternatively, an incremental time period of between 1 hour and about 24 hours or an incremental time period of greater than 24 hours) during the culturing period. For example the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume. The rate at which the second volume of the second liquid culture medium is added (volume/unit of time) can be about the same over the entire or part of the culturing period.

Skilled practitioners will appreciate that the first liquid culture medium and the second liquid culture medium can be the same type of media. In other instances, the first liquid culture medium and the second liquid culture medium can be different. The volume of the second liquid culture medium can be added to the first liquid culture medium in an automated fashion, e.g., by perfusion pump.

In some instances, adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell. The cell culture medium in fed-batch cultures is typically harvested at the end of culture period and used in any of the processes described herein, however, the cell culture medium in fed-batch cultures can also be harvested at one or more time points during the culturing period and used in any of the processes described herein.

Skilled practitioners will appreciate that any of the various culture parameters (e.g., containers, volumes, rates or frequencies of replacing culture volumes, agitation frequencies, temperatures, media, and $CO_2$ concentrations) can be used in any combination in to perform these methods. Further, any of the mammalian cells described herein or known in the art can be used to produce a recombinant protein.

Exemplary Biological Manufacturing Systems

Examples of biological manufacturing systems useful for performing the processes described herein and that include a MCCS or a MCCS1 and MCCS2 are described in U.S. Provisional Patent Application Ser. Nos. 61/775,060 and 61/856,390 (incorporated by reference). In these exemplary systems, at least one (e.g., at least two, three, four, five, or six) at least one reduced bioburden packed chromatography column provided herein is present in the MCCS or in the MCCS1 and/or MCCS2. For example, the entire system can include a total of two, three, four, five, six, seven, eight, nine, ten, eleven, twelve, thirteen, fourteen, fifteen, sixteen, seventeen, eighteen, nineteen, or twenty of the reduced bioburden packed chromatography columns provided herein. For example, the MCCS, MCCS1, and/or MCCS2 can include (or can each include) one, two, three, four, five, six, seven, eight, nine, or ten of the reduced bioburden packed chromatography columns provided herein.

For example, useful systems can include a MCCS1 that includes an inlet and a MCCS2 that includes an outlet, or an MCCS that includes an inlet and an outlet. In some embodiments, the MCCS1 and MCCS2 are in fluid communication with each other. These systems can also be configured such that fluid can be passed into the inlet, through the MCCS1 and MCCS2, and exit the manufacturing system through the outlet. These systems provide for the continuous and time-efficient production of a therapeutic drug substance from a liquid culture medium. For example, the elapsed time between feeding a fluid (e.g., a liquid culture medium) including a therapeutic protein into the MCCS1 and eluting purified recombinant protein (e.g., therapeutic protein drug substance) from the outlet of the MCCS2 can be, e.g., between about 4 hours and about 48 hours, inclusive.

Some exemplary systems do not include a break tank. In others, the system can include a maximum of 1, 2, 3, 4, or 5 break tank(s) in the entire system (e.g., where each break tank only holds a therapeutic protein for a total time period of, e.g., between about 5 minutes and about 6 hours, inclusive). The break tank(s) can have a capacity that is between 1 mL and about 300 mL, inclusive. Any break tank(s) disposed in the system such that fluid enters the break tank(s) prior to entering MCCS1 or MCCS can have a capacity that is between 1 mL and about 100%, inclusive, of the loading volume of the first column of the MCCS1 or MCCS, respectively. Any break tanks(s) disposed in the system such that fluid enters the break tank(s) prior to entering the MCCS2 (and after exiting the MCCS1) can have a capacity that is, e.g., between 1 mL and about 100%, inclusive, of the loading volume of the first column of the MCCS2.

Additional Exemplary System Structures and Features

The MCCS or MCCS1 can include an inlet through which fluid (e.g., a liquid culture medium that is substantially free of cells) can be passed into the MCCS or MCCS1, respectively. The inlet can be any structure known in the art for such purposes. It can include, e.g., a threading, ribbing, or a seal that allows for a fluid conduit to be inserted, such that after insertion of the fluid conduit into the inlet, fluid will enter the MCCS or MCCS1 through the inlet without significant seepage of fluid out of the inlet. Non-limiting inlets that can be used in the present systems are known and would be understood by those in the art.

The MCCS or MCCS1 can include at least two chromatography columns, at least two chromatographic membranes, or at least one chromatography column and at least one chromatographic membrane, and an inlet. The MCCS or MCCS1 can be any of the exemplary MCCSs described herein, or have one or more of any of the exemplary features of an MCCS (in any combination) described herein. The chromatography column(s) and/or the chromatographic membrane(s) present in the MCCS or MCCS1 can have one or more of any of the exemplary shapes, sizes, volumes (bed volumes), and/or unit operation(s) described herein.

The chromatography column(s) and/or the chromatographic membrane(s) present in the MCCS or MCCS1 can include one or more of any of the exemplary resins described herein or known in the art. For example, the resin included in one or more of the chromatography column(s) and/or chromatographic membrane(s) present in the MCCS or MCCS1 can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, an aptamer-binding capture mechanism, and/or a tag-binding capture mechanism). The resin included in one or more of the chromatography column(s) and/or chromatographic membrane(s) of the MCCS or MCCS1 can be a cation exchange resin, an anion exchange resin, a molecular sieve resin, or a hydrophobic interaction resin, or any combination thereof. Additional examples of resins that can be used to purify a recombinant protein are known in the art, and can be included in one or more of the chromatography column(s) and/or chromatographic membrane(s) present in the MCCS or MCCS1. The chromatography column(s) and/or chromatography membranes present in the MCCS or MCCS1 can include the same and/or different resins (e.g., any of the resins described herein or known in the art for use in recombinant protein purification).

The two or more chromatography column(s) and/or chromatographic resin(s) present in the MCCS or MCCS1 can perform one or more unit operations (e.g., capturing a recombinant protein, purifying a recombinant protein, polishing a recombinant protein, inactivating viruses, adjusting the ionic concentration and/or pH of a fluid including the recombinant protein, or filtering a fluid including a recombinant protein). In non-limiting examples, the MCCS or MCCS1 can perform the unit operations of capturing a recombinant protein from a fluid (e.g., a liquid culture medium) and inactivating viruses present in the fluid including the recombinant protein. The MCCS or MCCS1 can perform any combinations of two of more unit operations described herein or known in the art.

The chromatography column(s) and/or chromatographic membrane(s) present in the MCCS or MCCS1 can be connected or moved with respect to each other by a switching mechanism (e.g., a column-switching mechanism). The MCCS or MCCS1 can also include one or more (e.g., two, three, four, or five) pumps (e.g., automated, e.g., automated peristaltic pumps). The column-switching events can be triggered by the detection of a level of recombinant protein detected by UV absorbance corresponding to a certain level of recombinant protein in the fluid passing through the MCCS or MCCS1 (e.g., the input into and/or eluate from one or more of the chromatography column(s) and/or chromatographic membranes in the MCCS or MCCS1), a specific volume of liquid (e.g., buffer), or specific time elapsed. Column switching generally means a mechanism by which at least two different chromatography columns and/or chromatographic membranes in an MCCS or MCCS1 (e.g., two or more different chromatography columns and/or chromatographic membranes present in the MCCS1 or MCCS2) are allowed to pass through a different step (e.g., equilibration, loading, eluting, or washing) at substantially the same time during at least part of the process.

The MCCS or MCCS1 can be a Periodic Counter-Current Chromatography system (PCCS). For example, the PCCS that is the MCCS or MCCS1 (i.e., PCCS or PCCS1, respectively) can include four chromatography columns, where the first three columns perform the unit operation of capturing a recombinant protein from a fluid (e.g., a liquid culture medium), and the fourth column of the PCCS performs the unit operation of inactivating viruses in the fluid including the recombinant protein. A PCCS that is the MCCS or MCCS1 can utilize a column-switching mechanism. The PCC system can utilize a modified ÄKTA system (GE Healthcare, Piscataway, N.J.) capable of running up to, e.g., four, five, six, seven, or eight columns, or more.

The MCCS or MCCS1 can be equipped with: one or more (e.g., two, three, four, five, six, seven, eight, nine, or ten) UV monitors, one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The MCCS or MCCS1 can also be equipped with an operating system that utilizes software (e.g., Unicorn-based software, GE Healthcare, Piscataway, N.J.) for sensing when a column-switching should occur (e.g., based upon UV absorbance, volume of liquid, or time elapsed) and affecting (triggering) the column-switching events.

The MCCS or MCCS1 can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the MCCS or MCCS1 can include one or more (e.g., two, three, four, five, or six) break tanks that can hold fluid that cannot readily pass into one or more of the chromatography columns and/or chromatographic membranes in the MCCS or MCCS1. The systems described herein can include one or more break tanks (e.g., a break tank described herein) in the MCCS, MCCS1, and/or MCCS2. Other examples of the systems described herein do not include a break tank in the MCCS, MCCS1, or MCCS2, or do not include a break tank in the entire system. Other examples of the systems described herein include a maximum of one, two, three, four, or five break tank(s) (e.g., any break tank(s) described herein) in the entire system.

Second MCCS

The second MCCS (MCCS2) in the exemplary systems includes at least two chromatography columns, at least two chromatographic membranes, or at least one chromatography column(s) and at least one chromatographic membrane(s), and an outlet. The MCCS2 can any of the exemplary MCCSs described herein, or can have one or more of any of the exemplary features of an MCCS (in any combination) described herein. The chromatography column(s) and/or the chromatographic membrane(s) present in the MCCS2 can have one or more of: any of the shapes, sizes, volumes (bed volumes), and/or unit operations described herein. The chromatography column(s) and/or the chromatographic membrane(s) can include any of the exemplary resins described herein or known in the art. For example, the resin included in one or more of the chromatography column(s) and/or chromatographic membrane(s) present in the MCCS2 can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, tag-binding capture mechanism, and/or aptamer-binding capture mechanism). Useful resins include, e.g., a cation exchange resin, an anion exchange resin, a molecular sieve resin, and a hydrophobic interaction resin. Additional examples of resins are known in the art. The chromatography column(s) and/or chromatography membranes present in the MCCS2 can include the same and/or different resins (e.g., any of the resins described herein or known in the art for use in recombinant protein purification).

The chromatography column(s) and/or chromatographic membrane(s) present in the MCCS2 can perform one or more unit operations (e.g., any of the unit operations described herein or any combination of the unit operations described herein). In non-limiting examples, the MCCS2 can perform the unit operations of purifying a recombinant protein from a fluid and polishing the recombinant protein present in the fluid including the recombinant protein. In other non-limiting examples, the MCCS2 can perform the unit operations of purifying a recombinant protein present in a fluid, polishing a recombinant protein present in a fluid, and filtering a fluid including a recombinant protein. In another example, the MCCS2 can perform the unit operations of purifying a recombinant protein present in a fluid, polishing a recombinant protein present in a fluid, filtering a fluid including a recombinant protein, and adjusting the ionic concentration and/or pH of a fluid including a recombinant protein. The MCCS2 can perform any combination of two of more unit operations described herein or known in the art.

The chromatography column(s) and/or chromatographic membrane(s) present in the MCCS2 can be connected or moved with respect to each other by a switching mechanism (e.g., a column-switching mechanism). The MCCS2 can also include one or more (e.g., two, three, four, or five) pumps (e.g., automated, e.g., automated peristaltic pumps). The column-switching events can be triggered by the detection of a level of recombinant protein detected by UV absorbance corresponding to a certain level of recombinant protein in the fluid passing through the MCCS2 (e.g., the input into and/or eluate from one or more of the chromatography column(s) and/or chromatographic membranes in the MCCS2), a specific volume of liquid (e.g., buffer), or specific time elapsed.

The MCCS2 can be a Periodic Counter-Current Chromatography system (i.e., PCCS2). For example, the PCCS2 can include three columns that perform the unit operation of purifying a recombinant protein from a fluid, and a chromatographic membrane that performs the unit operation of polishing a recombinant protein present in a fluid. For example, the three columns that perform the unit operation of purifying a recombinant protein from a fluid can include, e.g., a cationic exchange resin, and the chromatographic membrane that performs the unit operation of polishing can include a cationic exchange resin. A PCCS2 can utilize a column-switching mechanism. The PCCS2 can utilize a modified ÄKTA system (GE Healthcare, Piscataway, N.J.) capable of running up to, e.g., four, five, six, seven, or eight columns, or more.

The MCCS2 can be equipped with: one or more (e.g., two, three, four, five, six, seven, eight, nine, or ten) UV monitors, one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The MCCS2 can also be equipped with an operating system that utilizes software (e.g., Unicorn-based software, GE Healthcare, Piscataway, N.J.) for sensing when a column-switching event should occur (e.g., based upon UV absorbance, volume of liquid, or time elapsed) and affecting the column-switching events.

The MCCS2 can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the MCCS2 can include one or more (e.g., two, three, four, five, or six) break tanks (e.g., any of the break tanks described herein) that can hold fluid that cannot readily pass into one or more of the chromatography columns and/or chromatographic membranes in the MCCS2.

The MCCS2 includes an outlet through which the therapeutic protein drug substance can exit the system. The outlet can include, e.g., a threading, ribbing, or a seal that allows for a fluid conduit to be inserted or a vial designed to hold or store the purified recombinant protein (e.g., therapeutic protein drug substance). An outlet can include a surface that can be used to seal a reduced bioburden vial or other such storage container onto the outlet in order to allow the purified recombinant protein (e.g., therapeutic protein drug substance) to flow directly into the reduced bioburden vial or storage container. Non-limiting outlets that can be used in the present systems are known and would be understood by those in the art.

The systems described herein can also include a fluid conduit that is disposed between the MCCS1 and the MCCS2. Any of the fluid conduits described herein can be, e.g., a tube that is made of, e.g., polyethylene, polycarbonate, or plastic. The fluid conduit disposed between the MCCS1 and the MCCS2 can further include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; a break tank (e.g., any of the break tank(s) described herein) that is in fluid communication with the fluid conduit and is positioned such that it can hold any excess fluid present in the fluid conduit that is unable to readily feed into the MCCS2; and one or more filters that are disposed in the fluid conduit such that they are capable of filtering (e.g., removing bacteria) the fluid present in the fluid conduit. Any of the in-line buffer adjustment reservoirs can include, e.g., a volume of between about 0.5 L to 50 L of buffer (e.g., at a temperature at or below 25° C., 15° C., or 10° C.).

The systems described herein can optionally include a fluid conduit disposed between the final chromatography column or chromatographic membrane in the MCCS2 and the outlet. The systems described herein can further include one or more filters in fluid connection with the fluid conduit disposed between the final chromatography column or chromatographic membrane in the MCCS2 and the outlet, such that the filter can remove, e.g., precipitated material, particulate matter, or bacteria from the fluid present in the fluid conduit disposed between the final chromatography column or chromatographic membrane in the MCCS2 and the outlet.

Some examples of the systems provided herein also include a bioreactor that is in fluid connectivity with the inlet of the MCCS or MCCS1. Any of the exemplary bioreactors described herein or known in the art can be used in the present systems.

Some examples of the systems provided herein also include a pump system. A pump system can include one or more the following: one or more (e.g., two, three, four, five, six, seven, eight, nine, or ten) pumps (e.g., any of the pumps described herein or known in the art), one or more (e.g., two, three, four, or five) filters (e.g., any of the filters described herein or known in the art), one or more (e.g., two, three, four, five, six, seven, eight, nine, or ten) UV detectors, and one or more (e.g., two, three, four, or five) break tanks (e.g., any of the break tanks described herein). Some examples of the systems provided herein further include a fluid conduit disposed between the pump and the inlet of the MCCS or MCCS1 (e.g., any of the exemplary fluid conduits described herein or known in the art). In some examples, this particular fluid conduit can include one or more (e.g., two, three, or four) pumps (e.g., any of the pumps described herein or known in the art) and/or one or more (e.g., two, three, or four) break tanks (e.g., any of the exemplary break tanks described herein), where these pump(s) and/or break tank(s) are in fluid connection with the fluid present in the fluid conduit.

Some examples of the systems described herein further include a further fluid conduit connected to the fluid conduit between the pump and the inlet, where one end of the further fluid conduit is fluidly connected to a bioreactor and the other end is fluidly connected to the fluid conduit between the pump and the inlet. This further fluid conduit can include a filter that is capable of removing cells from the liquid culture medium removed from the bioreactor (e.g., ATF cell retention system).

The systems provided herein allow for the continuous production of a purified recombinant protein (e.g., therapeutic protein drug substance). As is known in the art, the systems can provide for the periodic elution of a purified recombinant protein (e.g., therapeutic protein drug substance). The systems described herein can also result in a net yield of purified recombinant protein (e.g., therapeutic protein drug substance) of at least about 5 g/day, at least about 10 g/day, at least about 15 g/day, at least about 20 g/day, at least about 30 g/day, or at least about 40 g/day over a continuous period of at least about 5 days, at least about 10 days, at least about 15 days, at least about 20 days, at least about 25 days, at least about 30 days, at least about 40 days, at least about 50 days, at least about 60 days, at least about 70 days, at least about 80 days, at least about 90 days, or least about 100 days.

Methods of Reducing Bioburden of a Chromatography Resin that Include the Use of a Substantially Dry Chromatography Resin Also provided herein are methods of reducing bioburden of a chromatography resin that include (a) exposing a container comprising a substantially dry chromatography resin to a dose of gamma-irradiation sufficient to reduce the bioburden of the container and the chromatography resin. Some embodiments of these methods further include prior to step (a) drying a chromatography resin to remove liquid from the chromatography resin. Drying of a chromatography resin can be performed using heat treatment (e.g., an oven) or a dessicator. Additional methods for drying a chromatography resin are known in the art.

Any of the conditions and doses for gamma-irradiation described herein can be used in these methods. For example, the dose of gamma-irradiation can be between about 15 kGy to about 45 kGy (e.g., between about 20 kGy to about 30 kGy). Any of the containers and chromatography resins described herein can be used in these methods. For example, the container can be a storage vessel or a chromatography column. The chromatography resin in these methods can include a protein ligand (e.g., protein A or protein G). In some examples, the chromatography resin can include an anionic exchange chromatography resin (e.g., a chromatography resin including N-benzyl-N-methyl-ethanolamine groups). In some examples, the chromatography resin is covalently attached to a surface of an article (e.g., a chip, membrane, or cassette). In some embodiments, the substantially dry chromatography resin does not contain a significant amount of an antioxidant agent or a significant amount of a chelator. Also provided are reduced bioburden chromatography resins produced by any of the methods described herein.

In some examples, the reduced bioburden chromatography resin produced has a sterility assurance level (SAL) of between about $1 \times 10^{-8}$ to about $1 \times 10^{-5}$ (e.g., a SAL of between about $1 \times 10^{-7}$ to about $1 \times 10^{-6}$). The reduced chromatography resin produced can include at least one resin selected from the group consisting of: anionic exchange chromatography resin, cationic exchange chromatography resin, affinity chromatography resin, hydrophobic interaction chromatography resin, and size exclusion chromatography resin. In some examples, the reduced chromatography resin produced includes an affinity chromatography resin comprising a protein ligand (e.g., protein A). In some examples, the reduced chromatography resin produced includes an anionic exchange chromatography resin (e.g., an anionic exchange chromatography resin including N-benzyl-N-methyl-ethanolamine groups). Also provided are methods of making a reduced bioburden packed chromatography column that include providing the reduced bioburden chromatography resin produced by any of the methods described herein; and packing the chromatography resin into a reduced bioburden column in an aseptic environment. Also provided are reduced bioburden packed chromatography columns produced by any of the methods described herein.

Also provided are integrated, closed, and continuous processes for reduced bioburden manufacturing of a purified recombinant protein that include: (a) providing a liquid culture medium including a recombinant protein that is substantially free of cells; and (b) continuously feeding the liquid culture medium into a multi-column chromatography system (MCCS) comprising at least one reduced bioburden packed chromatography column produced by any of the methods provided herein; where the process utilizes reduced bioburden buffer, is integrated, and runs continuously from the liquid culture medium to an eluate from the MCCS that is the purified recombinant protein. Also provided are integrated, closed, and continuous processes for reduced bioburden manufacturing of a purified recombinant protein that include: (a) providing a liquid culture medium including a recombinant protein that is substantially free of cells; (b) continuously feeding the liquid culture medium into a first multi-column chromatography system (MCCS1); (c) capturing the recombinant protein in the liquid culture medium using the MCCS1; (d) producing an eluate from the MCCS1 that includes the recombinant protein and continuously feeding the eluate into a second multi-column chromatography system (MCCS2); (e) continuously feeding the recombinant protein from the eluate into the MCCS2 and subsequently eluting the recombinant protein to thereby produce the purified recombinant protein, where: the process utilizes reduced bioburden buffer, is integrated, and runs continuously from the liquid culture medium to the purified recombinant protein, and at least one column in the MCCS1 and/or MCCS2 contains a reduced bioburden packed chromatography column produced by any of the methods provided herein. Any of the exemplary aspects of integrated, closed, and continuous processes for reduced bioburden manufacturing of a purified recombinant protein described herein can be used in these processes.

Methods of Producing Reduced Bioburden Membranes, Resins, Coated Materials, Chips, and Cassettes Also provided herein are methods for producing a reduced bioburden membrane, resin, coated material, chip, or cassette that include: exposing a container including a composition including a membrane, resin, coated material, chip, or cassette (e.g., a cellulose-, agarose-, or a sugar-based membrane, resin, coated material, chip, or cassette); and at least one antioxidant agent and/or chelator to a dose of gamma-irradiation sufficient to reduce the bioburden of the container and the membrane, resin, coated material, chip, or cassette, where the at least one antioxidant agent and/or chelator is present in an amount sufficient to ameliorate the damage to the membrane, resin, coated material, chip, and cassette after exposure to the dose of gamma-irradiation. In some examples, the cassette is a resin-containing cassette (e.g., any of the exemplary resins described herein or known in the art). In some embodiments, the membrane, resin, coated material, chip, or cassette includes a protein A or protein G ligand covalently attached to at least one or part of its surface. In some embodiments, the composition includes a membrane, resin, coated material, chip, or cassette and a liquid including the at least one antioxidant agent and/or the at least one chelator. Any of the exemplary combinations and concentrations of antioxidant agent(s) and/or chelator(s) described herein can be used in any of these methods. Any of the exemplary liquids described herein can be used in any of these methods. In some embodiments, the composition is a dry material. Also provided herein is a reduced bioburden membrane, resin, coated material, chip, or cassette produced using any of the methods described herein. In some examples the container is a sealed storage container or vessel.

Also provided herein are methods for producing a reduced bioburden membrane, resin, coated material, chip, and cassette that include: exposing a container including a substantially dry membrane, resin, coated material, chip, or cassette (e.g., a cellulose-, agarose-, or a sugar-based membrane, resin, coated material, chip, or cassette) to a dose of gamma-irradiation sufficient to reduce the bioburden of the container and the membrane, resin, coated material, chip, or cassette. Some examples further include a step of drying the membrane, resin, coated materials, chip, or cassette prior to the exposing step. In some embodiments, the membrane, resin, coated material, chip, or cassette includes a protein A or protein G ligand covalently attached to its surface. In some examples, the cassette is a resin-containing cassette (e.g., any of the exemplary resins described herein or known in the art). Also provided herein is a reduced bioburden membrane, resin, coated material, chip, or cassette produced using any of the methods described herein.

The invention is further described in the following examples, which do not limit the scope of the invention described in the claims.

EXAMPLES

Example 1

Effect of Gamma-Irradiation on Static Binding Capacity of Different Chromatography Resins A set of experiments was performed to test the effect of gamma-irradiation on the static binding capacity of three different protein A affinity chromatography resins: GE Mab Select SuRe™ (a highly cross-linked agarose resin having a particle size of 85 μm, and epoxy functional groups connecting protein A to the agarose), JSR LifeSciences Amsphere ProA JWT203 (a porous poly-methacrylate resin having a particle size of ~50 μm, and epoxy functional groups connecting protein A to the poly-methacrylate), and Kaneka KanCap A (a highly cross-linked cellulose having a particle size of 65-85 μm, with protein A linked to the cellulose through reductive amination). Each of the three resins was treated with 15 kGy of gamma-irradiation, with the exception of Mab Select SuRe™ which was treated with the radiation dose of 25kGy, and a control sample of GE Mab Select SuRe™ resin was left untreated, loaded with anti-TGFβ antibody (IgG4), and the level of the anti-TGFβ antibody in the eluate was determined. Gamma-irradiation of each of the resins in this example was performed in 50 mM phosphate, pH 7.0. The static binding curves of each of the gamma-irradiated resins and the untreated control resin are shown in FIG. 1. These data show that gamma-irradiation reduces the binding capacity of each of the three tested protein A chromatography resins, with the JSR LifeSciences Amsphere ProA JWT203 resin showing the smallest decrease in binding capacity in response to 15 kGy gamma-irradiation.

A next experiment was performed to determine whether gamma-irradiation of the JSR LifeSciences Amsphere ProA JWT203 resin or the GE Mab Select SuRe™ resin results in a cleavage (and release) of protein A from the chromatography resin. In these experiments, JSR LifeSciences Amsphere ProA JWT203 resin or the GE Mab Select SuRe™ resin were treated with 30 kGy of gamma-irradiation, and then the level of protein A in the supernatant was determined by measuring the absorbance at 280 nm. The data from this experiment show that little protein A is released from either of these two tested resins following treatment with gamma-irradiation (FIG. 2).

These data show that gamma-irradiation results in an immediate decrease in the binding capacity of affinity chromatography resin, and that such loss in binding capacity is not due to cleavage of the protein ligand from the resin.

Example 2

Multiple of Gamma-Irradiation on Binding Capacity of Resin Over Multiple Cycles of Chromatography A next set of experiments was performed to test the effect of gamma-irradiation on the binding capacity of chromatography resin over multiple cycles of chromatography. These experiments were performed using JSR LifeSciences Amsphere ProA JWT203 resin as this resin showed the least amount of loss of binding capacity in response to gamma-irradiation in Example 1. Gamma-irradiation of each of the resins in this example was performed in 50 mM phosphate, pH 7.0.

Figure 3:
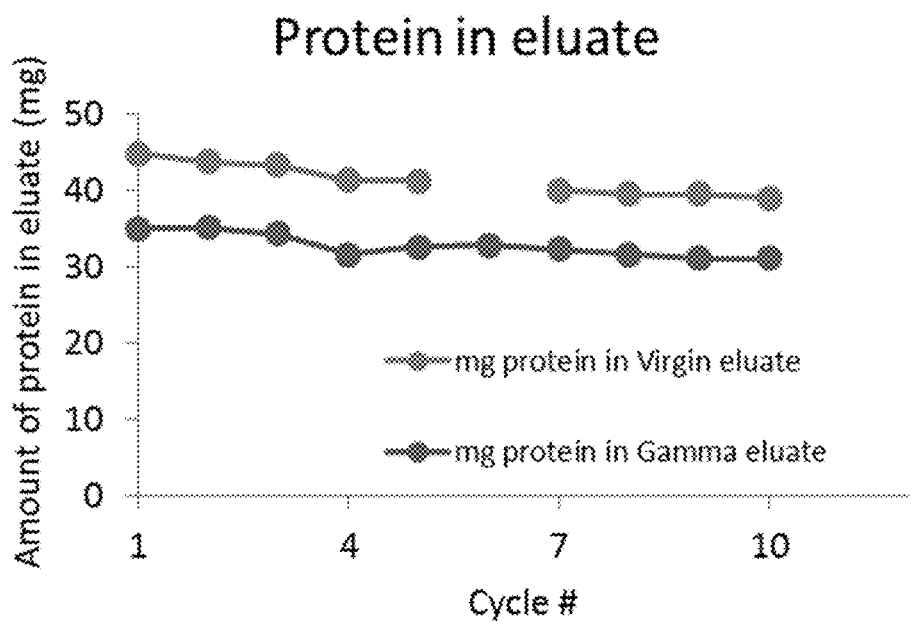
FIG. 3 is a graph showing the amount of protein in eluate over multiple cycles of chromatography performed using untreated JSR LifeSciences Amsphere ProA JWT203 resin (virgin eluate) or 15 kGy gamma-irradiated JSR LifeSciences Amsphere ProA JWT203 resin (gamma eluate).
Figure 6:
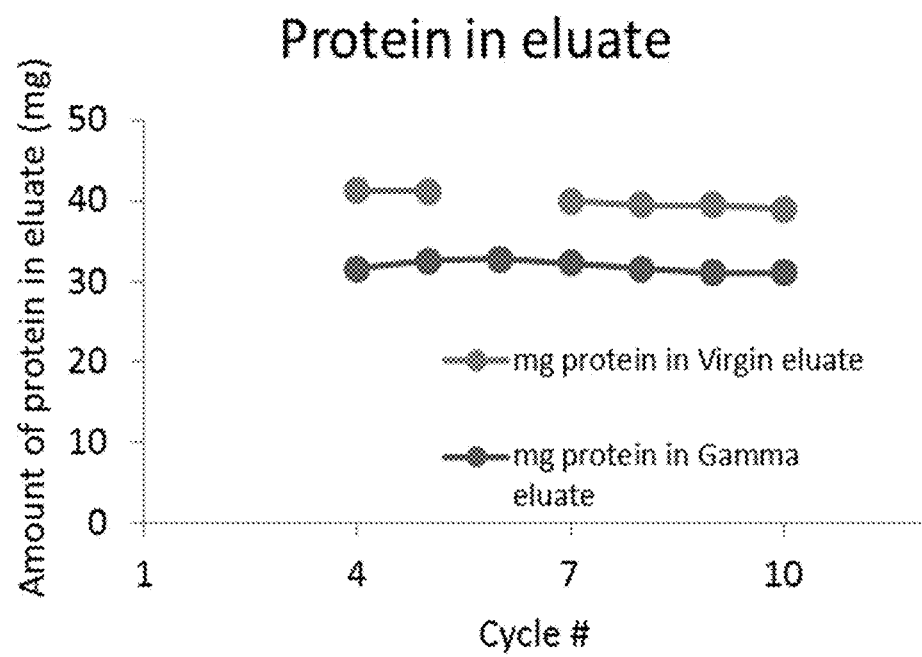
FIG. 6 is a graph showing the amount of protein in the eluate over multiple cycles of continuous chromatography performed using untreated during continuous chromatography performed using untreated JSR LifeSciences Amsphere ProA JWT203 resin (virgin) or 15 kGy gamma-irradiated JSR LifeSciences Amsphere ProA JWT203 resin (Gamma).
Figure 7:
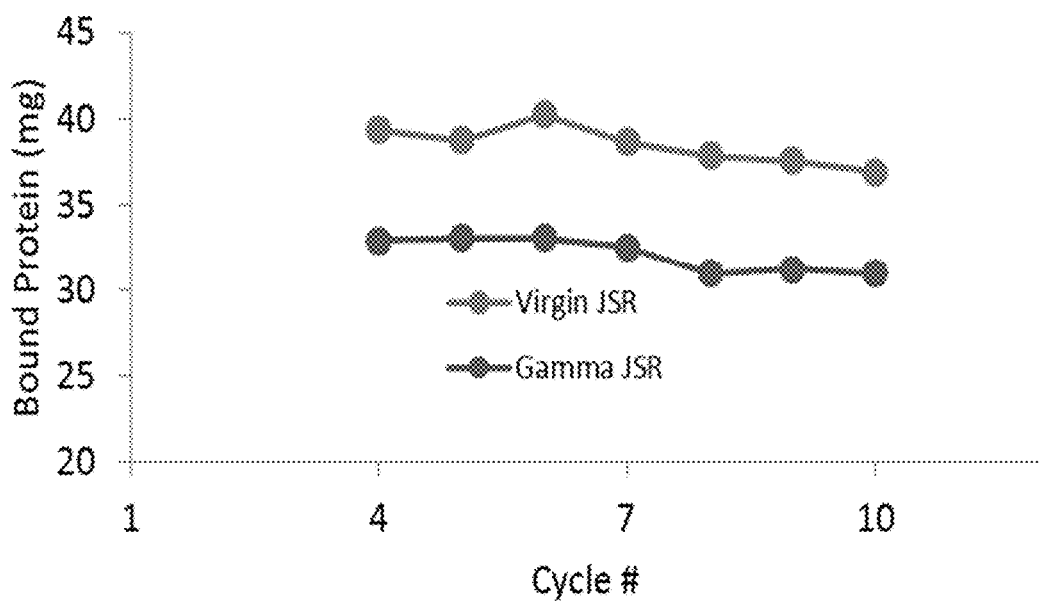
FIG. 7 is a graph of the protein bound over multiple cycles of chromatography performed using untreated JSR LifeSciences Amsphere ProA JWT203 resin (virgin) or 15 kGy gamma-irradiated JSR LifeSciences Amsphere ProA JWT203 resin (gamma).

A first experiment was performed to test the effect of 15 kGy gamma-irradiation on the ability of JSR LifeSciences Amsphere ProA JWT203 resin to bind to the anti-TGFβ antibody (IgG4) over multiple cycles of chromatography. An untreated JSR LifeSciences Amsphere ProA JWT203 resin was also used to perform multiple cycles of chromatography, as a positive control. At the end of each cycle, the resins were washed with 0.1 N NaOH. The amount of the anti-TGFβ antibody in eluate from each cycle was determined. The data show that 15 kGy gamma-irradiation results in an immediate, about 20% to 25%, decrease in binding capacity of the JSR LifeSciences Amsphere ProA JWT203 resin (i.e., in the first cycle), but the binding capacity only decreases at a very slow rate over the multiple additional cycles of chromatography (i.e., at a rate comparable to the rate of decrease of binding capacity of the untreated resin) (FIGS. 3, 6, and 7).

Figure 4:
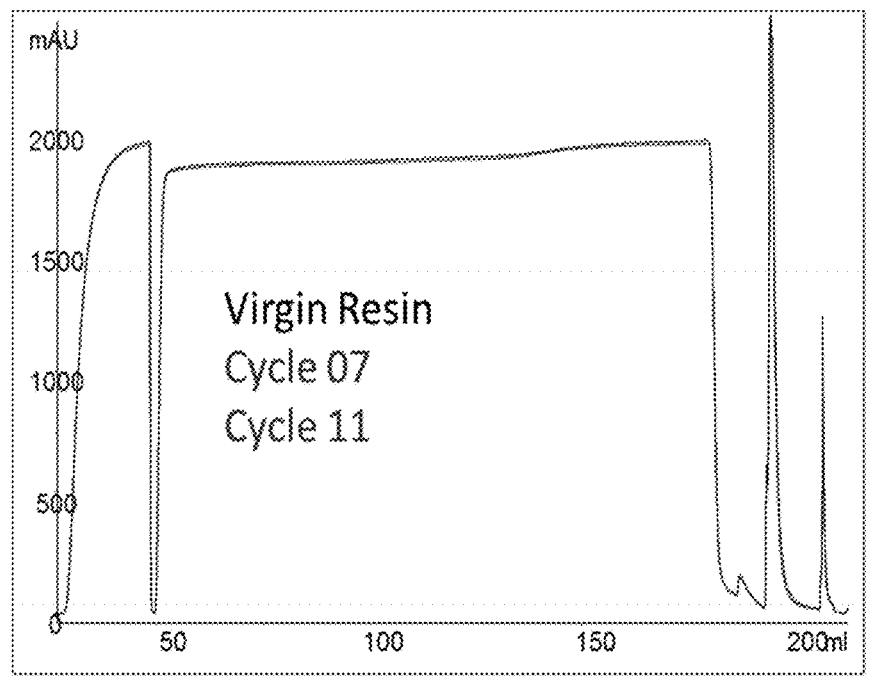
FIG. 4 is a chromatograph showing the elution profile of cycle 7 and cycle 11 during continuous chromatography performed using untreated JSR LifeSciences Amsphere ProA JWT203 resin.
Figure 5:
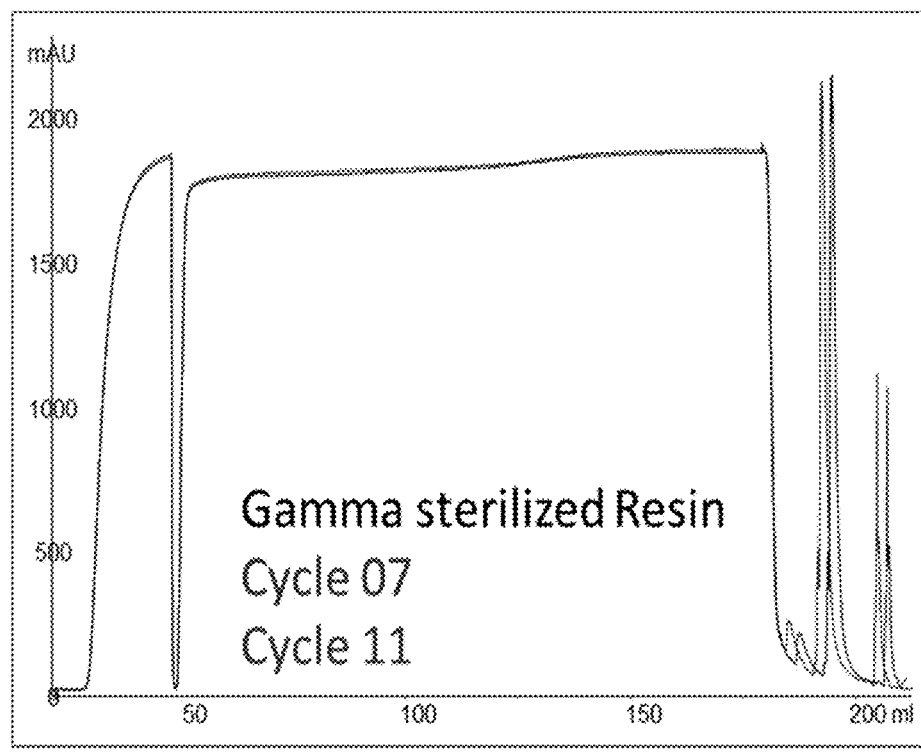
FIG. 5 is a chromatograph showing the elution profile of cycle 7 and cycle 11 during continuous chromatography performed using 15 kGy gamma-irradiated JSR LifeSciences Amsphere ProA JWT203 resin.

The minimal decrease in binding capacity of the 15 kGy gamma-irradiated JSR LifeSciences Amsphere ProA JWT203 resin after the initial cycle of chromatography is also apparent from a comparison of the chromatographs at cycle 7 and cycle 11 in these experiments (FIGS. 4 and 5). These figures show that for both the untreated and the 15 kGy gamma-irradiated JSR LifeSciences Amsphere ProA JWT203 resin there is only a modest, if any, observable change in the binding capacity of these resins over multiple cycles of chromatography.

Figure 8:
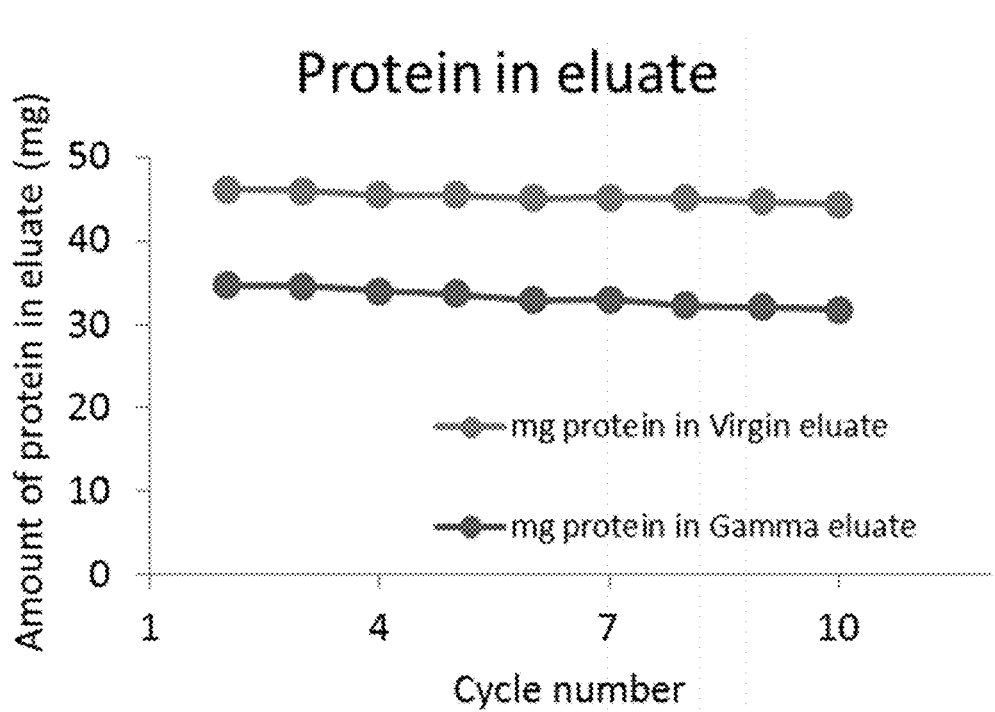
FIG. 8 is a graph showing the amount of protein in eluate over multiple cycles of chromatography performed using untreated JSR LifeSciences Amsphere ProA JWT203 resin (virgin) or 29 kGy gamma-irradiated JSR LifeSciences Amsphere ProA JWT203 resin (Gamma).

Additional experiments were performed to test the change in binding capacity of JSR LifeSciences Amsphere ProA JWT203 resin left untreated or treated with 29 kGy gamma-irradiation over multiple cycles of chromatography. In these experiments, the resins were washed with 0.1 N NaOH at the end of each cycle, and the resins were loaded with anti-αβTCR monoclonal antibody (IgG1) at the start of each cycle. The resulting data again show an about 20% to 25% initial drop in binding capacity of the 29 kGy gamma-irradiated resin as compared to the untreated resin (FIG. 8). The binding capacity of the untreated and 29 kGy gamma-irradiated resin only modestly decreased over multiple additional cycles of chromatography (at about the same rate for the untreated and 29 kGy gamma-irradiated resin) (FIG. 8).

Figure 9:
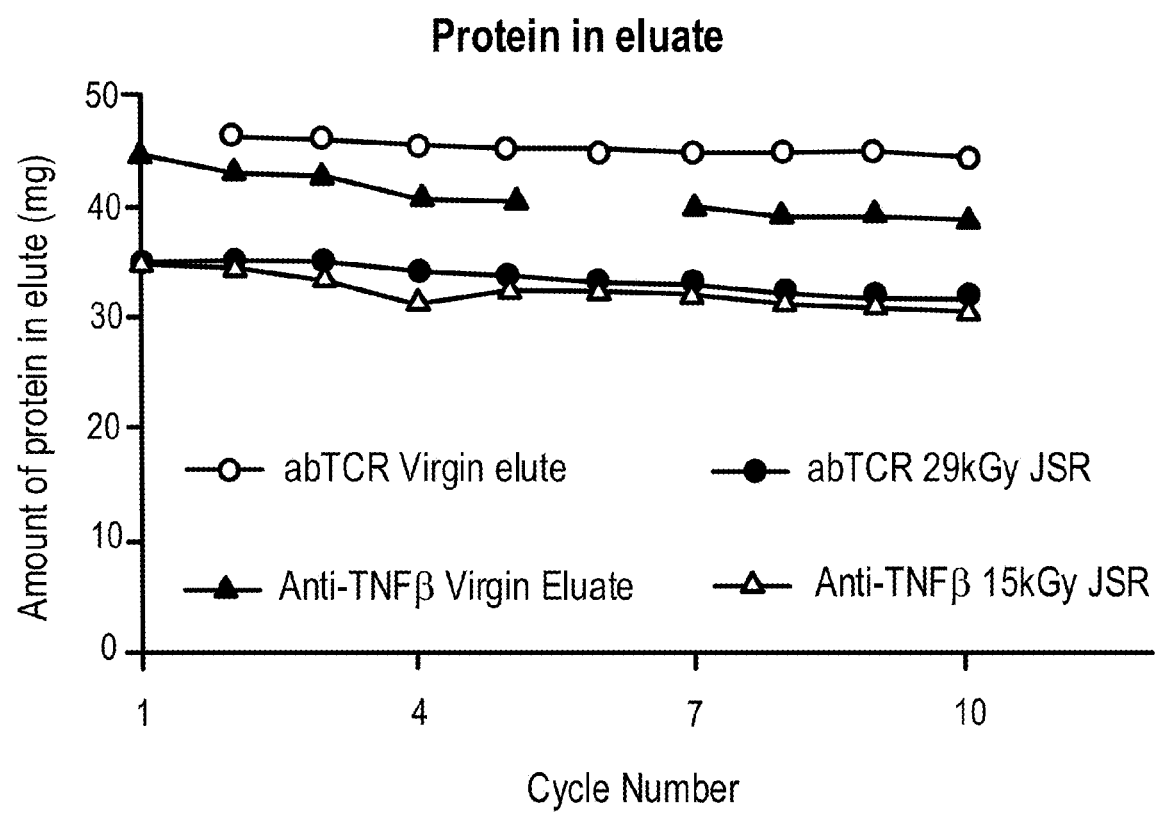
FIG. 9 is a graph showing the amount of protein (anti-αβTCR (IgG1) or anti-TGFβ (IgG4)) in eluate over multiple cycles of chromatography performed using untreated JSR LifeSciences Amsphere ProA JWT203 resin (virgin), 15 kGy gamma-irradiated JSR LifeSciences Amsphere ProA JWT203 resin (15 kGy), or 29 kGy gamma-irradiated JSR LifeSciences Amsphere ProA JWT203 resin (29 kGy).

A final set of experiments was performed to test the binding capacity of untreated, 15 kGy gamma-irradiated, and 29 kGy gamma-irradiated JSR LifeSciences Amsphere ProA JWT203 resin over multiple cycles of chromatography. At the end of each cycle, the resins were washed with 0.1 N NaOH, and the resin was loaded with either monoclonal anti-TGFβ (IgG4) antibody or monoclonal anti-αβTCR (IgG1) antibody (abTCR). The data show that irradiation with 15 kGy and 29 kGy of gamma-irradiation results in substantially the same level of decrease in binding capacity of the JSR LifeSciences Amsphere ProA JWT203 resin, and that the level of binding capacity of the 15 kGy and 29 kGy gamma-irradiated JSR LifeSciences Amsphere ProA JWT203 resin modestly decreases over multiple cycles of chromatography at the same rate as the untreated resin (FIG. 9).

These data show that gamma-irradiation of a chromatography resin with a protein ligand results in an immediate decrease in binding capacity, and that the loss in binding capacity remains relatively stable over multiple rounds of chromatography. These data suggest that gamma-irradiation results in oxidative damage to chromatography resin (e.g., chromatography resin containing a protein or peptide ligand, such as affinity chromatography resin) during gamma-irradiation, and that loss in binding capacity of chromatography resin (e.g., chromatography resin containing a protein or peptide ligand, such as affinity chromatography resin) during gamma-irradiation can be prevented, ameliorated, or reduced by gamma-irradiating the chromatography resin in the presence of at least one chelator and/or antioxidant agent.

Example 3

Effect of Gamma-Irradiation on Binding Capacity on GE Mab Select SuRe™ Resin

Figure 11:
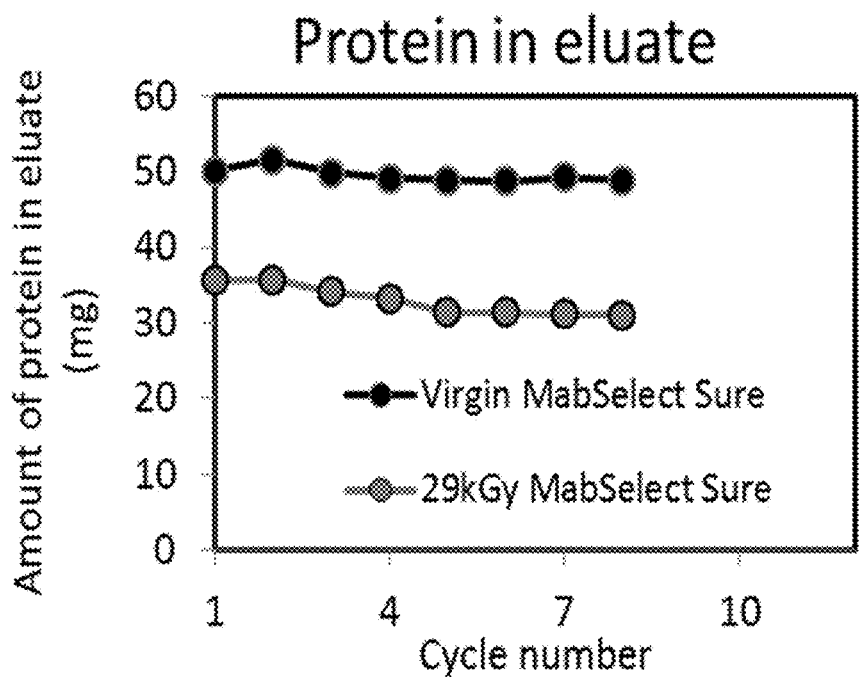
FIG. 11 is a graph of the protein in the eluate of untreated (virgin) and 29-kGy gamma-irradiated GE Mab Select SuRe™ resin over multiple chromatography cycles when a culture medium containing monoclonal IgG1 was used to load each resin.
Figure 12:
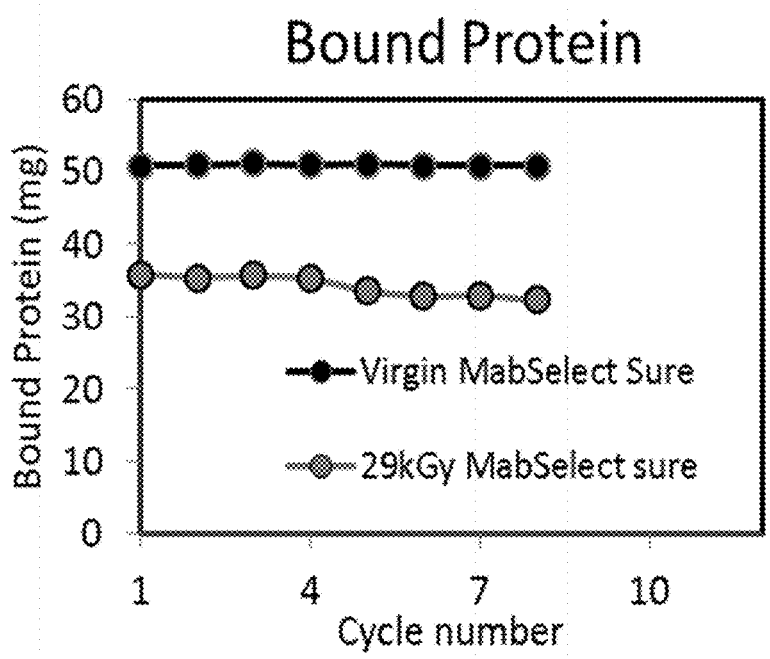
FIG. 12 is a graph of amount of protein bound to untreated (virgin) and 29-kGy gamma-irradiated GE Mab Select SuRe™ resin over multiple chromatography cycles when a culture medium containing monoclonal IgG1 was used to load each resin.

A set of experiments was performed to determine the effect of gamma-irradiation on the binding capacity of another protein ligand chromatography resin (GE Mab Select SuRe™ resin) over multiple cycles of chromatography. The resin was exchanged into 50 mM sodium phosphate, pH 7.0, and then treated with 29 kGy gamma-irradiation in a 30-mL Nalgene bottle. The resin was then packed into a 0.66-cm diameter column with a bed height of 3 cm (1 mL column). This column was then used to capture a monoclonal IgG1 antibody in a cell culture medium over multiple cycles of chromatography. An untreated GE Mab Select SuRe™ resin was also used to perform multiple cycles of chromatography as a positive control. At the end of each cycle, the resins were washed with 0.1 N NaOH. The amount of IgG1 in eluate from each cycle was determined. The data show that 29 kGy gamma-irradiation results in an immediate, about 25% to about 30%, decrease in the binding capacity of the GE Mab Select SuRe™ resin (i.e., in the first cycle) (FIGS. 11 and 12). After the first cycle of chromatography, the 29 kGy gamma-irradiated GE Mab Select SuRe™ resin only showed a very slow rate of decrease in binding capacity over multiple additional cycles of chromatography (i.e., at a rate comparable to the rate of decrease of binding capacity of the untreated resin over multiple chromatography cycles) (FIGS. 11 and 12). These data are similar to the data obtained for the JSR Protein A resin described in Example 2 and the mechanism for loss of resin binding capacity due to gamma-irradiation appears to be similar.

Example 4

Figure 13:
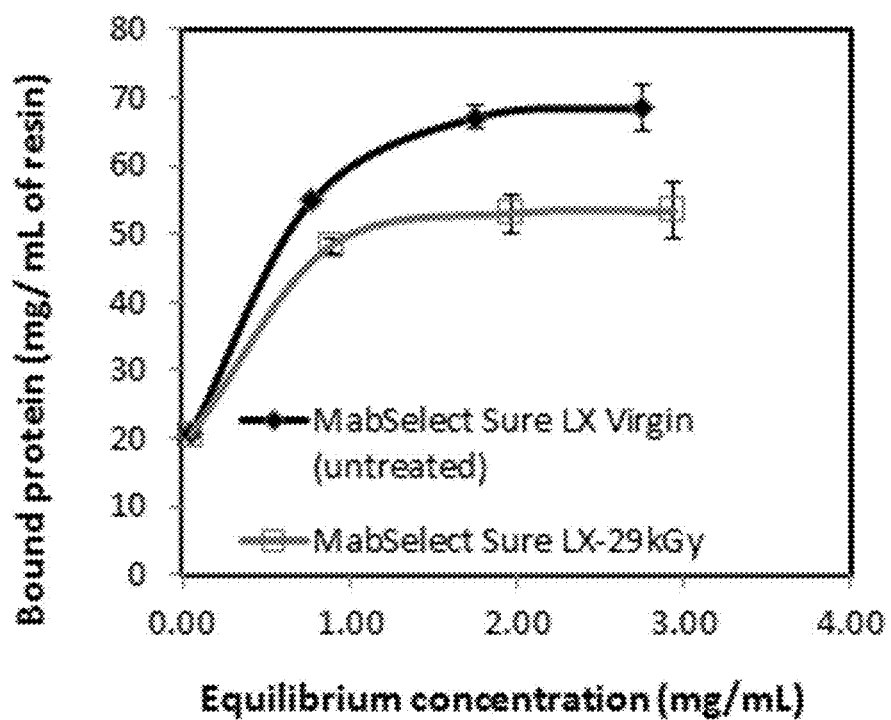
FIG. 13 is a graph of the amount of protein bound (mg bound protein/mL of resin) to untreated (virgin) and 29-kGy gamma-irradiated GE Mab Select SuRe™ LX resin following loading with different equilibrium concentrations of a monoclonal IgG4 antibody.

Effect of Gamma-Irradiation on Static Binding Capacity of MAb Select SuRe™ LX Resin The data described in Example 1 show that gamma-irradiation reduces the static binding capacity of three different Protein A chromatography resins (GE Mab Select SuRe™, JSR LifeSciences Amsphere™ ProA JWT203, and Kaneka KanCapA™). Gamma-irradiation was tested with another protein A chromatography resin: GE Mab Select SuRe™ LX. GE Mab Select SuRe™ LX resin has an agarose backbone and a similar protein A ligand as Mab Select SuRe™ resin, but has a higher ligand density as compared to Mab Select SuRe™ resin. The resin buffer was exchanged from 20% ethanol to 50 mM sodium phosphate, pH 6.0, and was then subjected to 29-kGy gamma-irradiation. The static binding of the resin was determined as described in Example 1 (with static binding capacity of the resin determined before and after gamma-irradiation). The data indicate a similar drop in static binding capacity of the resin after gamma-irradiation (FIG. 13). This gamma-irradiation-induced decrease in static binding capacity of the GE Mab Select SuRe™ LX resin is similar to the drop in static binding capacity observed for the three protein A chromatography resins tested in Example 1 following gamma-irradiation (FIG. 1). The data in FIG. 13 show that gamma-irradiation of Mab Select SuRe™ LX results in an immediate decrease in the static binding capacity of the resin.

Example 5

Reduction of the Gamma-Irradiation-Induced Decrease in Binding Capacity of a Chromatography Resin The data in the previous examples show that gamma-irradiation of chromatography resin in a dose that reduces the bioburden of the resin, also results in a drop in the binding capacity of the resin: a decrease in the resin binding capacity of about 20% to about 40% as compared to the binding capacity of a control untreated resin. The extent of the decrease in binding capacity caused by gamma-irradiation does not appear to depend on the protein A ligand attached to the resin and/or the bead chemistry of the resin. This additional set of experiments was performed to identify buffered solutions that would prevent the loss in binding capacity of a chromatography resin that occurs during gamma-irradiation. GE Mab Select SuRe™ LX was used as the chromatography resin in these experiments. GE Mab Select SuRe™ LX has protein A covalently immobilized onto the porous matrix of each bead. The resin was first buffer exchanged from 20% ethanol to a different buffer including one or more antioxidant agents or a control buffer not including any antioxidant agents. The tested buffered solutions are shown in Table 1 below. In a control experiment, the resin was gamma-irradiated as a dry composition in the absence of antioxidant agents. These resin samples were dried in an oven at 23° C. for 2 days such that water content was minimized during gamma-irradiation. Each resin sample shown in Table 1 was gamma-irradiated at a dose of 29 kGy in a 30-mL Nalgene bottle. The static binding capacity was determined for the gamma-irradiated resin samples and for the untreated (non-irradiated) resin samples using the methods described in Example 1.

TABLE 1

Tested GE Mab Select SuRe ™ LX Resin Samples and Buffered Solutions

| Resin | Base buffer | Quenchers |
|---|---|---|
| Virgin MabSelect SuRe LX | 50 mM Sodium phosphate, pH 6.0 | None |
| 29 kGy MabSelect SuRe LX | 50 mM Sodium phosphate, pH 6.0 | None |
| 29 kGy MabSelect SuRe LX | 50 mM Sodium phosphate, pH 6.0 | 100 mM Mannitol |
| 29 kGy MabSelect SuRe LX | 50 mM Sodium phosphate, pH 6.0 | 100 mM Methionine |
| 29 kGy MabSelect SuRe LX | 50 mM Sodium phosphate, pH 6.0 | 100 mM sodium ascorbate |
| 29 kGy MabSelect SuRe LX | 50 mM Sodium phosphate, pH 6.0 | 100 mM Histidine |
| 29 kGy MabSelect SuRe LX | 50 mM Sodium phosphate, pH 6.0 | 50 mM Methionine + 50 mM Histidine |
| 29 kGy MabSelect SuRe LX | 50 mM Sodium phosphate, pH 6.0 | 33 mM Methionine + 33 mM Histidine + 33 mM sodium ascorbate |
| 29 kGy MabSelect SuRe LX | 50 mM Sodium phosphate, pH 6.0 | 25 mM sodium ascorbate + 25 mM Methionine + 25 mM Mannitol + 25 mM Histidine |
| Dried Virgin MabSelect SuRe LX | None | None |
| Dried 29 kGy MabSelect SuRe LX | None | None |

Figure 14:
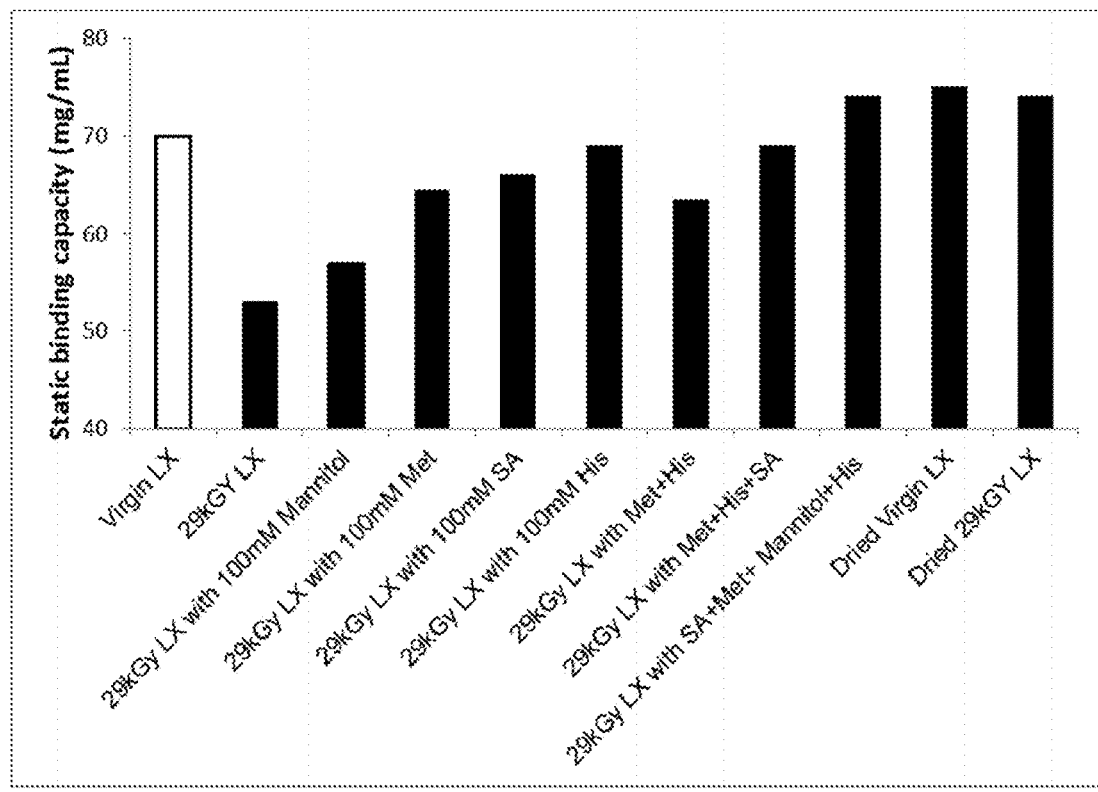
FIG. 14 is a graph of the static binding capacity (mg protein/mL of resin) at an equilibrium IgG4 antibody concentration of 2 mg/mL of untreated GE Mab Select SuRe™ LX resin (virgin LX), 29-kGy gamma-irradiated GE Mab Select SuRe™ LX resin (29kGY LX), dry untreated GE Mab Select SuRe™ LX resin, and dry 29-kGy gamma-irradiated GE Mab Select SuRe™ LX resin, and GE Mab Select SuRe™ LX resin gamma-irradiated at a dose of 29 kGy in the presence of one of seven different tested buffers containing at least one antioxidant agent.

The data show that gamma-irradiation of the chromatography resin in the presence of one or more antioxidant agents decreased the loss in binding capacity caused by gamma-irradiation (FIG. 14 and Table 2). The buffer of 25 mM sodium ascorbate, 25 mM methionine, 25 mM mannitol, 25 mM histidine, 50 mM sodium phosphate, pH 6.0 (referred to hereafter as "SMMH" buffer) completely mitigated the gamma-irradiation-induced loss in binding capacity of the resin (i.e., there was no loss in binding capacity observed between the untreated control resin and the resin gamma-irradiated with a dose of 29 kGy in the presence of SMMH buffer) (FIG. 14 and Table 2). The 29-kGy gamma-irradiated dried resin sample had the same binding capacity as the untreated resin sample. These data indicate that gamma-irradiating a dry chromatography resin is another way to decrease the extent of gamma-irradiation-induced loss in resin binding capacity.

TABLE 2

Specific Binding Capacity for Tested GE Mab Select SuRe ™ LX Resin Samples

| Resin | Base buffer | Quenchers | SBC (mg/mL) |
|---|---|---|---|
| Virgin MabSelect SuRe | 50 mM Sodium phosphate, pH 7.0 | None | 50 |
| 29 kGy MabSelect SuRe | 50 mM Sodium phosphate, pH 7.0 | None | 32.8 |

TABLE 2-continued

Specific Binding Capacity for Tested GE Mab Select SuRe ™ LX Resin Samples

| Resin | Base buffer | Quenchers | SBC (mg/mL) |
|---|---|---|---|
| Virgin MabSelect SuRe LX | 50 mM Sodium phosphate, pH 6.0 | None | 70 |
| 29 kGy MabSelect SuRe LX | 50 mM Sodium phosphate, pH 6.0 | None | 53 |
| 29 kGy MabSelect SuRe LX | 50 mM Sodium phosphate, pH 6.0 | 100 mM Mannitol | 57 |
| 29 kGy MabSelect SuRe LX | 50 mM Sodium phosphate, pH 6.0 | 100 mM Methionine | 64.5 |
| 29 kGy MabSelect SuRe LX | 50 mM Sodium phosphate, pH 6.0 | 100 mM sodium ascorbate | 66 |
| 29 kGy MabSelect SuRe LX | 50 mM Sodium phosphate, pH 6.0 | 100 mM Histidine | 69 |
| 29 kGy MabSelect SuRe LX | 50 mM Sodium phosphate, pH 6.0 | 50 mM Methionine + 50 mM Histidine | 63.5 |
| 29 kGy MabSelect SuRe LX | 50 mM Sodium phosphate, pH 6.0 | 33 mM Methionine + 33 mM Histidine + 33 mM sodium ascorbate | 69 |
| 29 kGy MabSelect SuRe LX | 50 mM Sodium phosphate, pH 6.0 | 25 mM sodium ascorbate + 25 mM Methionine + 25 mM Mannitol + 25 mM Histidine | 74 |
| Dried Virgin MabSelect SuRe LX | None | None | 75 |
| Dried 29 kGy MabSelect SuRe LX | None | None | 74 |

Figure 15:
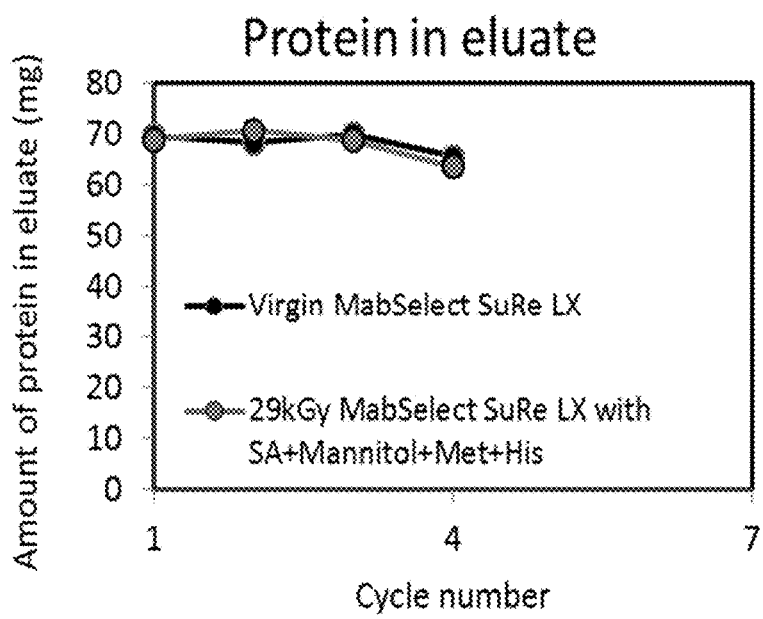
FIG. 15 is a graph of the amount of protein in the eluate over multiple chromatography cycles performed using untreated GE Mab Select SuRe™ LX resin (virgin) or GE Mab Select SuRe™ LX resin gamma-irradiated with a dose of 29 kGy in the presence of 25 mM mannitol, 25 mM histidine, 25 mM sodium ascorbate, 25 mM methionine, 50 mM sodium phosphate, pH 6.0.
Figure 16:
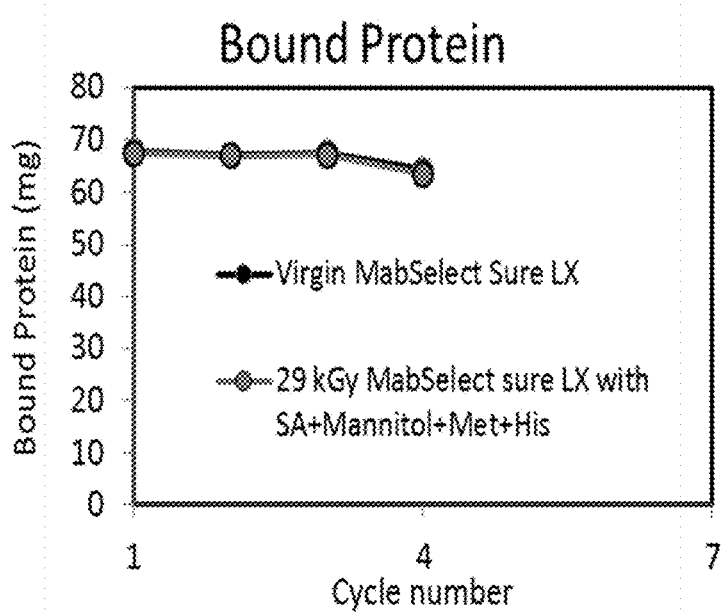
FIG. 16 is a graph of the amount of protein bound over multiple chromatography cycles performed using untreated GE Mab Select SuRe™ LX resin (virgin) or GE Mab Select SuRe™ LX resin gamma-irradiated with a dose of 29 kGy in the presence of 25 mM mannitol, 25 mM histidine, 25 mM sodium ascorbate, 25 mM methionine, 50 mM sodium phosphate, pH 6.0.
Figure 17:
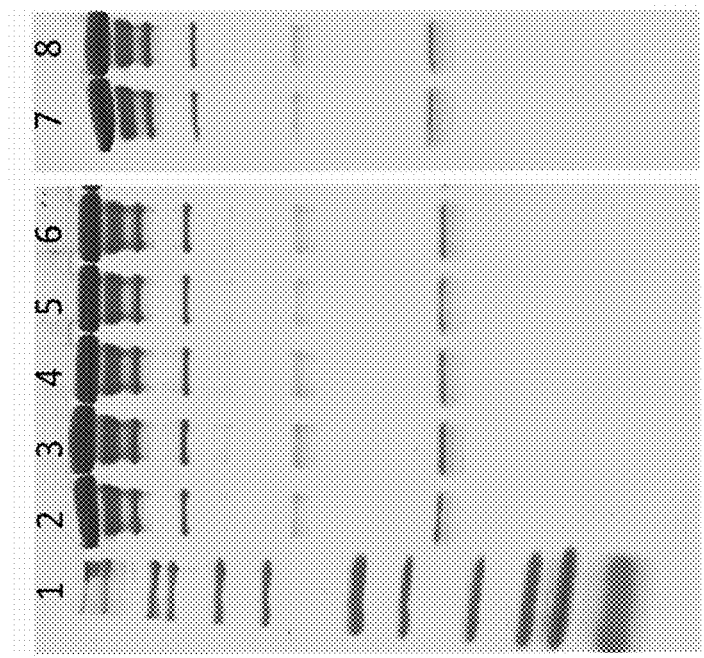
FIG. 17 is a non-reduced sodium-dodecyl sulfate polyacrylamide gel showing the IgG1 antibody eluate over multiple chromatography cycles using untreated GE Mab Select SuRe™ LX resin (virgin LX) and GE Mab Select SuRe™ LX resin gamma-irradiated with a dose of 29 kGy in the presence of 25 mM mannitol, 25 mM histidine, 25 mM sodium ascorbate, 25 mM methionine, 50 mM sodium phosphate, pH 6.0.

A further experiment was performed to test the performance of resin gamma-irradiated with a dose of 29 kGy in the presence of the SMMH buffer and untreated resin over multiple chromatography cycles. Each tested resin was packed into a 0.66-cm diameter and 3-cm height column. The columns were loaded with cell culture medium containing a monoclonal IgG1 antibody. As observed in the static binding capacity experiments (FIG. 14), the dynamic binding capacity was comparable between the untreated resin and the resin gamma-irradiated with a dose of 29 kGy in the presence of the SMMH buffer for all cycles (FIGS. 15 and 16). In addition, other critical quality and process performance indicators were also comparable: the percentage of high molecular weight species measured by size exclusion chromatography-high performance liquid chromatography (SEC-HPLC) and the concentration of host cell protein (HCP) in the eluate (Table 3). FIG. 17 is a non-denaturing sodium dodecyl sulfate polyacrylamide gel depicting the comparable purity of the eluate over multiple cycles from the untreated resin and the resin gamma-irradiated at a dose of 29 kGy in the presence of the SMMH buffer.

TABLE 3

Percentage of High Molecular Weight Species and Host Cell Protein in Eluate of Untreated GE Mab Select SuRe ™ LX Resin and GE Mab Select SuRe ™ LX Resin Gamma-Irradiated in the Presence of SMMH Buffer

| Protein A eluate | % HMWS | HCP (ng/mg) | Protein A eluate | % HMWS | HCP (ng/mg) |
|---|---|---|---|---|---|
| Virgin eluate cycle 1 | 1.55 | 173 | SMMH eluate cycle 1 | 1.82 | 107.6 |
| Virgin eluate cycle 3 | 1.73 | 247.2 | SMMH eluate cycle 2 | 1.75 | N/A |
| Virgin eluate cycle 5 | 1.89 | 289.5 | SMMH eluate cycle 3 | 1.59 | 146.2 |

The percentage high molecular weight species was measured by size exclusion chromatography high performance liquid chromatography (SEC-HPLC) using a Tosoh G3000 SWxl column and the host cell protein concentration was measured using an ELISA assay.

Additional buffered solutions were tested for their ability to reduce gamma-irradiation-induced loss in binding capacity of chromatography resin. In these experiments, a single chromatography cycle was performed to determine binding capacity in dynamic mode. For each tested buffer, a column similar to the one described above (0.66-cm diameter×3-cm height) was packed and loaded with cell culture medium containing a monoclonal IgG1. As observed in the static binding capacity experiments (FIG. 14), each buffer containing at least one antioxidant agent reduced the loss in resin binding capacity caused by gamma-irradiation (Table 4). These data show that the presence of at least one antioxidant agent can reduce the loss in resin binding capacity caused by gamma-irradiation. In addition, these data also suggest that chelators (which bind and prevent redox active metals from generating reactive oxygen and nitrogen species) would also be able to decrease the loss in resin binding capacity caused by gamma-irradiation.

TABLE 4

Data from Single Chromatography Cycle on GE MabSelect SuRe LX Resin (Untreated and 29 kGy-Irradiated in the Presence or Absence of Quenchers) with Cell Culture Harvest Containing IgG1

| Resin condition | Protein in Eluate (mg) | Bound protein (mg) |
|---|---|---|
| Virgin MabSelect SuRe LX | 70 | 68 |
| 29 kGy MabSelect SuRe LX with SMMH | 69 | 67 |
| 29 kGy MabSelect SuRe LX with 100 mM Histidine | 68 | 67 |
| 29 kGy MabSelect SuRe LX with 100 mM Methionine | 64 | 63 |
| 29 kGy MabSelect SuRe LX with 100 mM SA | 62 | 61 |
| 29 kGy MabSelect SuRe LX | 51 | 51 |

Overall, these data suggest that gamma-irradiation of chromatography resin in the presence of at least one antioxidant agent and/or at least one chelator can decrease the loss in resin binding capacity caused by gamma-irradiation. The data also suggest that the presence of at least one antioxidant agent and/or at least one chelator protect the immobilized protein A ligand, as well as the resin base matrix, from damage caused by free radicals formed during gamma-irradiation. The presence of at least one antioxidant agent and/or at least one chelator can also be used in other bioprocessing applications that include the gamma-irradiation of a material at a dosage that may cause damage to a matrix and/or functional groups. For example, compositions containing at least one antioxidant agent and/or at least one chelator agent can be used to prevent gamma-irradiation induced damage to cellulose membranes and other cellulose-, agarose-, or sugar-based resins, membranes, or materials.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing bioburden of a chromatography resin comprising:
 exposing a container comprising a composition comprising (i) a chromatography resin and (ii) a liquid comprising at least one chelator to a dose of gamma-irradiation sufficient to reduce the bioburden of the container and the chromatography resin, wherein the at least one chelator is present in an amount sufficient to ameliorate the loss of binding capacity of the chromatography resin after exposure to the dose of gamma-irradiation.

2. The method of claim 1, wherein the container is a storage vessel.

3. The method of claim 1, wherein the container is a chromatography column.

4. The method of claim 1, wherein the container is a packed chromatography column.

5. The method of claim 1, wherein the composition is a slurry of sedimented chromatography resin in the liquid.

6. The method of claim 5, wherein the liquid is a buffered solution.

7. The method of claim 1, wherein the at least one chelator is selected from the group consisting of: ethylenediaminetetraacetic acid (EDTA), 2,3-dimercapto-1-propanesulfonic acid sodium (DMPS), dimercaptosuccinic acid (DMSA), metallothionin, and desferroxamine.

8. The method of claim 1, wherein the chromatography resin is selected from the group consisting of: an anion exchange chromatography resin, a cation exchange chromatography resin, an affinity chromatography resin, a hydrophobic interaction chromatography resin, and a size exclusion chromatography resin.

9. The method of claim 1, wherein the dose is between about 15 kGy and about 45 kGy.

10. A method of reducing bioburden of a chromatography resin comprising:
 exposing a container comprising a composition comprising a chromatography resin and at least one antioxidant agent to a dose of gamma-irradiation sufficient to reduce the bioburden of the container and the chromatography resin, wherein the at least one antioxidant agent is present in an amount sufficient to ameliorate the loss of binding capacity of the chromatography resin after exposure to the dose of gamma-irradiation.

11. The method of claim 10, wherein the container is a storage vessel.

12. The method of claim 10, wherein the container is a chromatography column.

13. The method of claim 10, wherein the container is a packed chromatography column.

14. The method of claim 10, wherein the composition further comprises at least one chelator.

15. The method of claim 10, wherein the composition is a slurry of sedimented chromatography resin in a liquid comprising the at least one antioxidant agent.

16. The method of claim 10, wherein the composition is a solid mixture.

17. The method of claim 10, wherein the composition comprises at least one antioxidant agent selected from the group consisting of: reduced glutathione, reduced thioredoxin, reduced cysteine, a carotenoid, melatonin, lycopene, tocopherol, reduced ubiquinone, ascorbate, bilirubin, uric acid, lipoic acid, a flavonoid, a phenolpropanoid acid, lidocaine, naringenin, fullerene, glucose, histidine, methionine, mannitol, 4-hydroxy-2,2,6,6-tetramethylpiperidin-1-oxyl, and dimethylmethoxy chromanol.

18. The method of claim 15, wherein the liquid is a buffered solution.

19. The method of claim 10, wherein the chromatography resin is selected from the group consisting of: an anion exchange chromatography resin, a cation exchange chromatography resin, an affinity chromatography resin, a hydrophobic interaction chromatography resin, and a size exclusion chromatography resin.

20. The method of claim 10, wherein the dose is between about 15 kGy and about 45 kGy.

21. A method of reducing bioburden of a chromatography resin comprising:
 exposing a container comprising a composition comprising a chromatography resin and methionine and/or histidine to a dose of gamma-irradiation sufficient to reduce the bioburden of the container and the chromatography resin, wherein the methionine and/or histidine is present in an amount sufficient to ameliorate the loss of binding capacity of the chromatography resin after exposure to the dose of gamma-irradiation.

22. The method of claim 21, wherein the composition comprises a chromatography resin and between 5 mM and about 150 mM methionine.

23. The method of claim 21, wherein the composition comprises a chromatography resin and between about 5 mM and about 150 mM histidine.

24. The method of claim 21, wherein the composition comprises a chromatography resin, between about 5 mM and about 150 mM methionine, and between about 5 mM and about 150 mM histidine.

25. The method of claim 21, wherein the container is a storage vessel or a chromatography column.

26. The method of claim 21, wherein the container is a packed chromatography column.

27. The method of claim 21, wherein the composition is a solid mixture or a slurry of sedimented chromatography resin in a liquid comprising the methionine and/or histidine.

28. The method of claim 27, wherein the liquid is a buffered solution.

29. The method of claim 21, wherein the chromatography resin is selected from the group consisting of: an anion exchange chromatography resin, a cation exchange chromatography resin, an affinity chromatography resin, a hydrophobic interaction chromatography resin, and a size exclusion chromatography resin.

30. The method of claim 21, wherein the dose is between about 15 kGy and about 45 kGy.

* * * * *